US010028723B2

(12) United States Patent
Konofagou et al.

(10) Patent No.: US 10,028,723 B2
(45) Date of Patent: Jul. 24, 2018

(54) SYSTEMS AND METHODS FOR REAL-TIME, TRANSCRANIAL MONITORING OF BLOOD-BRAIN BARRIER OPENING

(71) Applicant: The Trustees of Columbia University in the City of New York, New York, NY (US)

(72) Inventors: Elisa E. Konofagou, New York, NY (US); Tobias Teichert, New York, NY (US); Vincent P. Ferrera, New York, NY (US); Fabrice Marquet, New York, NY (US); Yao-Sheng Teng, New York, NY (US); Shih-Ying Wu, New York, NY (US)

(73) Assignee: THE TRUSTEES OF COLUMBIA UNIVERSITY IN THE CITY OF NEW YORK, New York ( * ) Notice: Subject to any disclaimer, the term of this patent is extended or adjusted under 35 U.S.C. 154(b) by 290 days.

(21) Appl. No.: 14/476,543

(22) Filed: Sep. 3, 2014

(65) Prior Publication Data

US 2015/0065871 A1    Mar. 5, 2015

Related U.S. Application Data

(60) Provisional application No. 61/873,310, filed on Sep. 3, 2013.

(51) Int. Cl.
A61B 8/00    (2006.01)
A61B 8/08    (2006.01)
(Continued)

(52) U.S. Cl.
CPC .......... *A61B 8/0808* (2013.01); *A61B 8/4281* (2013.01); *A61B 8/5223* (2013.01);
(Continued)

(58) Field of Classification Search
CPC ..... A61B 8/0808; A61B 8/4281; A61B 8/481; A61B 8/5223; A61B 2090/378;
(Continued)

(56) References Cited

U.S. PATENT DOCUMENTS 3,598,111 A    8/1971 Kahn
4,463,608 A    8/1984 Takeuchi et al.
(Continued)

FOREIGN PATENT DOCUMENTS

EP    0 221 409    5/1987
EP    0 627 206    12/1994
(Continued)

OTHER PUBLICATIONS

U.S. Appl. No. 11/433,510 (U.S. Pat. No. 8,858,441), filed May 12, 2006 (Oct. 14, 2014).

(Continued)

*Primary Examiner* — Sanjay Cattungal
(74) *Attorney, Agent, or Firm* — Baker Botts L.L.P.

(57) ABSTRACT

Systems and techniques for real-time, transcranial monitoring of safe blood-brain barrier opening include determining an approach angle for targeted blood-brain barrier opening proximate a predetermined region in a brain of a patient, and positioning an ultrasound transducer to generate a focused ultrasound signal at the determined approach angle to the predetermined region in the brain.

20 Claims, 22 Drawing Sheets

(51) Int. Cl.
*A61N 7/02* (2006.01)
*A61N 7/00* (2006.01)
*A61B 90/00* (2016.01)

(52) U.S. Cl.
CPC .............. *A61N 7/02* (2013.01); *A61B 8/481* (2013.01); *A61B 2090/378* (2016.02); *A61N 2007/0039* (2013.01); *A61N 2007/0052* (2013.01); *A61N 2007/0091* (2013.01)

(58) Field of Classification Search
CPC .............. A61N 7/02; A61N 2007/0039; A61N 2007/0052; A61N 2007/0091
USPC .................................................. 600/437–469
See application file for complete search history.

(56) References Cited

U.S. PATENT DOCUMENTS

| | | | |
|---|---|---|---|
| 4,777,599 A | 10/1988 | Dorogi et al. | |
| 4,832,941 A | 5/1989 | Berwing et al. | |
| 4,858,613 A | 8/1989 | Fry et al. | |
| 4,882,679 A | 11/1989 | Tuy et al. | |
| 4,926,675 A | 5/1990 | Schohl et al. | |
| 5,038,787 A | 8/1991 | Antich et al. | |
| 5,107,837 A | 4/1992 | Ophir et al. | |
| 5,178,147 A | 1/1993 | Ophir et al. | |
| 5,309,914 A | 5/1994 | Iinuma | |
| 5,433,708 A | 7/1995 | Nichols et al. | |
| 5,435,310 A | 7/1995 | Sheehan et al. | |
| 5,457,754 A | 10/1995 | Han et al. | |
| 5,601,084 A | 2/1997 | Sheehan et al. | |
| 5,606,971 A | 3/1997 | Sarvazyan | |
| 5,662,113 A | 9/1997 | Liu | |
| 5,722,411 A | 3/1998 | Suzuki et al. | |
| 5,741,522 A | 4/1998 | Violante et al. | |
| 5,752,515 A | 5/1998 | Jolesz et al. | |
| 5,769,790 A | 6/1998 | Watkins et al. | |
| 5,810,731 A | 9/1998 | Sarvazyan et al. | |
| 5,840,028 A | 11/1998 | Chubachi et al. | |
| 5,928,151 A | 7/1999 | Hossack et al. | |
| 6,026,173 A | 2/2000 | Svenson et al. | |
| 6,028,066 A | 2/2000 | Unger | |
| 6,102,864 A | 8/2000 | Hatfield et al. | |
| 6,102,865 A | 8/2000 | Hossack et al. | |
| 6,106,465 A | 8/2000 | Napolitano et al. | |
| 6,123,669 A | 9/2000 | Kanda et al. | |
| 6,152,878 A | 11/2000 | Nachtomy et al. | |
| 6,193,951 B1 | 2/2001 | Ottoboni et al. | |
| 6,200,266 B1 | 3/2001 | Shokrollahi et al. | |
| 6,241,675 B1 | 6/2001 | Smith et al. | |
| 6,246,895 B1 | 6/2001 | Plews | |
| 6,259,943 B1 | 7/2001 | Cosman et al. | |
| 6,270,459 B1 | 8/2001 | Konofagou et al. | |
| 6,309,355 B1 | 10/2001 | Cain et al. | |
| 6,312,382 B1 | 11/2001 | Mucci et al. | |
| 6,352,507 B1 | 3/2002 | Torp et al. | |
| 6,413,216 B1 | 7/2002 | Cain et al. | |
| 6,425,867 B1 | 7/2002 | Vaezy et al. | |
| 6,447,450 B1 | 9/2002 | Oldstad | |
| 6,488,629 B1 | 12/2002 | Saetre et al. | |
| 6,491,636 B2 | 12/2002 | Chenal et al. | |
| 6,508,768 B1 | 1/2003 | Hall et al. | |
| 6,514,221 B2 | 2/2003 | Hynynen et al. | |
| 6,529,770 B1 | 3/2003 | Grimblatov | |
| 6,537,217 B1 | 3/2003 | Bjærum et al. | |
| 6,537,221 B2 | 3/2003 | Criton et al. | |
| 6,671,541 B2 | 12/2003 | Bishop et al. | |
| 6,683,454 B2 | 1/2004 | Rehwald et al. | |
| 6,685,641 B2 | 2/2004 | Liu et al. | |
| 6,689,060 B2 | 2/2004 | Phelps et al. | |
| 6,701,341 B1 | 3/2004 | Wu | |
| 6,770,033 B1 | 8/2004 | Fink et al. | |
| 6,875,176 B2 | 4/2005 | Mourad et al. | |
| 6,936,151 B1 | 8/2005 | Lock et al. | |
| 6,994,673 B2 | 2/2006 | Lysyansky et al. | |
| 7,016,719 B2 | 3/2006 | Rudy et al. | |
| 7,055,378 B2 | 6/2006 | Su et al. | |
| 7,136,518 B2 | 11/2006 | Griffin et al. | |
| 7,257,244 B2 | 8/2007 | Miga | |
| 7,331,926 B2 | 2/2008 | Varghese et al. | |
| 7,344,509 B2 | 3/2008 | Hynynen et al. | |
| 7,421,101 B2 | 9/2008 | Georgescu et al. | |
| 7,429,249 B1 | 9/2008 | Winder et al. | |
| 7,449,306 B2 | 11/2008 | Elson et al. | |
| 7,601,122 B2 | 10/2009 | Zagzebski et al. | |
| 7,753,847 B2 | 7/2010 | Greenleaf et al. | |
| 7,809,426 B2 | 10/2010 | Kim et al. | |
| 7,896,821 B1 | 3/2011 | Magnin et al. | |
| 8,029,444 B2 | 10/2011 | Pedrizzetti et al. | |
| 8,208,709 B2 | 6/2012 | Ding et al. | |
| 8,257,338 B2 | 9/2012 | Keenan et al. | |
| 9,063,220 B2 | 6/2015 | Yoda et al. | |
| 9,358,023 B2 * | 6/2016 | Konofagou .......... | A61B 17/225 |
| 2002/0034757 A1 | 3/2002 | Cubicciotti | |
| 2002/0038086 A1 | 3/2002 | Hynynen et al. | |
| 2002/0039594 A1 | 4/2002 | Unger | |
| 2002/0065461 A1 | 5/2002 | Cosman | |
| 2002/0095081 A1 | 7/2002 | Vilsmeier | |
| 2002/0151792 A1 | 10/2002 | Conston et al. | |
| 2002/0169394 A1 | 11/2002 | Eppstein et al. | |
| 2002/0193784 A1 | 12/2002 | McHale et al. | |
| 2003/0097068 A1 | 5/2003 | Hossack et al. | |
| 2003/0125621 A1 | 7/2003 | Drukker et al. | |
| 2003/0171672 A1 | 9/2003 | Varghese et al. | |
| 2003/0174890 A1 | 9/2003 | Yamauchi | |
| 2003/0220556 A1 | 11/2003 | Porat et al. | |
| 2004/0006266 A1 | 1/2004 | Ustuner et al. | |
| 2004/0049134 A1 | 3/2004 | Tosaya et al. | |
| 2004/0054357 A1 | 3/2004 | O'Donnell | |
| 2004/0059224 A1 | 3/2004 | Varghese et al. | |
| 2004/0092816 A1 | 5/2004 | Ossmann et al. | |
| 2004/0097805 A1 | 5/2004 | Verard et al. | |
| 2004/0172081 A1 | 9/2004 | Wang | |
| 2004/0210134 A1 | 10/2004 | Hynynen et al. | |
| 2004/0210135 A1 | 10/2004 | Hynynen | |
| 2004/0234113 A1 | 11/2004 | Miga | |
| 2004/0236219 A1 | 11/2004 | Liu et al. | |
| 2004/0249580 A1 | 12/2004 | Pourcelot et al. | |
| 2004/0258760 A1 | 12/2004 | Wheatley et al. | |
| 2005/0004466 A1 | 1/2005 | Hynenen et al. | |
| 2005/0026262 A1 | 2/2005 | Yoshitani et al. | |
| 2005/0054930 A1 | 3/2005 | Rickets et al. | |
| 2005/0059876 A1 | 3/2005 | Krishnan | |
| 2005/0080336 A1 | 4/2005 | Byrd et al. | |
| 2005/0080469 A1 | 4/2005 | Larson et al. | |
| 2005/0084538 A1 | 4/2005 | Dayton et al. | |
| 2005/0124892 A1 | 6/2005 | Weitzel et al. | |
| 2005/0175541 A1 | 8/2005 | Lanza et al. | |
| 2005/0201942 A1 | 9/2005 | Dugstad et al. | |
| 2005/0203395 A1 | 9/2005 | Sui et al. | |
| 2005/0203399 A1 | 9/2005 | Vaezy et al. | |
| 2005/0259864 A1 | 11/2005 | Dickinson et al. | |
| 2005/0267695 A1 | 12/2005 | German | |
| 2005/0277824 A1 | 12/2005 | Aubry et al. | |
| 2005/0277835 A1 | 12/2005 | Angelsen et al. | |
| 2006/0034904 A1 | 2/2006 | Weimann | |
| 2006/0058651 A1 | 3/2006 | Chiao et al. | |
| 2006/0058671 A1 | 3/2006 | Vitek et al. | |
| 2006/0058673 A1 | 3/2006 | Aase et al. | |
| 2006/0074315 A1 | 4/2006 | Liang et al. | |
| 2006/0078501 A1 | 4/2006 | Goertz et al. | |
| 2006/0173320 A1 | 8/2006 | Radulescu | |
| 2006/0241529 A1 | 10/2006 | Hynynen et al. | |
| 2007/0049824 A1 | 3/2007 | Konofagou et al. | |
| 2007/0055179 A1 | 3/2007 | Deem et al. | |
| 2007/0059247 A1 | 3/2007 | Lindner et al. | |
| 2007/0071683 A1 | 3/2007 | Dayton et al. | |
| 2007/0129652 A1 * | 6/2007 | Nita ..................... | A61B 5/6864 601/2 |
| 2007/0207194 A1 | 9/2007 | Grayburn et al. | |
| 2007/0219447 A1 | 9/2007 | Kanai et al. | |
| 2007/0232962 A1 | 10/2007 | Zumeris et al. | |
| 2007/0239001 A1 | 10/2007 | Mehi et al. | |
| 2007/0276242 A1 | 11/2007 | Konofagou et al. | |

(56) References Cited

U.S. PATENT DOCUMENTS

| | | | |
|---|---|---|---|
| 2007/0276245 A1 | 11/2007 | Konofagou et al. | |
| 2007/0276254 A1 | 11/2007 | Konofagou | |
| 2008/0089848 A1 | 4/2008 | DiMauro | |
| 2008/0194957 A1 | 8/2008 | Hoctor et al. | |
| 2008/0200417 A1 | 8/2008 | Semple et al. | |
| 2008/0243214 A1 | 10/2008 | Koblish | |
| 2008/0260802 A1 | 10/2008 | Sawhney et al. | |
| 2008/0269606 A1 | 10/2008 | Matsumura | |
| 2008/0269668 A1 | 10/2008 | Keenan et al. | |
| 2008/0285819 A1 | 11/2008 | Konofagou et al. | |
| 2008/0319355 A1* | 12/2008 | Nita | A61N 7/00 601/2 |
| 2008/0319375 A1 | 12/2008 | Hardy | |
| 2009/0005711 A1 | 1/2009 | Konofagou et al. | |
| 2009/0191244 A1 | 7/2009 | Kheir et al. | |
| 2009/0221916 A1 | 9/2009 | Konofagou et al. | |
| 2009/0247911 A1 | 10/2009 | Novak et al. | |
| 2009/0270790 A1 | 10/2009 | Raghavan | |
| 2010/0049036 A1 | 2/2010 | Kimh | |
| 2010/0056924 A1 | 3/2010 | Powers | |
| 2010/0143241 A1* | 6/2010 | Johnson | A61K 41/0028 424/1.11 |
| 2010/0286527 A1 | 11/2010 | Cannon et al. | |
| 2011/0028854 A1 | 2/2011 | Addison et al. | |
| 2011/0098562 A1 | 4/2011 | Salgo et al. | |
| 2011/0177005 A1 | 7/2011 | Rapoport et al. | |
| 2011/0208038 A1 | 8/2011 | Konofagou et al. | |
| 2011/0295105 A1 | 12/2011 | Konofagou et al. | |
| 2011/0313328 A1* | 12/2011 | Nita | A61N 7/022 601/2 |
| 2012/0004693 A1 | 1/2012 | Lo et al. | |
| 2012/0179073 A1* | 7/2012 | Nita | A61N 7/00 601/2 |
| 2013/0038479 A1 | 2/2013 | Eldar et al. | |
| 2013/0046229 A1 | 2/2013 | Konofagou et al. | |
| 2013/0066211 A1 | 3/2013 | Konofagou et al. | |
| 2013/0131495 A1* | 5/2013 | Konofagou | A61B 8/0808 600/411 |
| 2013/0195313 A1 | 8/2013 | Gauthier et al. | |
| 2013/0204166 A1 | 8/2013 | Villanueva et al. | |
| 2013/0289398 A1 | 10/2013 | Borden et al. | |
| 2013/0304407 A1 | 11/2013 | George et al. | |
| 2013/0315491 A1 | 11/2013 | Konofagou et al. | |
| 2014/0114216 A1* | 4/2014 | Konofagou | A61B 8/481 601/2 |
| 2016/0107002 A1* | 4/2016 | Nita | A61N 7/00 601/2 |

FOREIGN PATENT DOCUMENTS

| | | |
|---|---|---|
| WO | WO 1999/037938 | 7/1999 |
| WO | WO 2005/030171 | 4/2005 |
| WO | WO 2007/0148279 | 12/2007 |
| WO | WO 2008/015012 | 2/2008 |
| WO | WO 2008/027520 | 3/2008 |
| WO | WO 2008/062342 | 5/2008 |
| WO | WO 2008/131217 | 10/2008 |
| WO | WO 2008/131302 | 10/2008 |
| WO | WO 2008/157422 | 12/2008 |
| WO | WO 2010/030819 A1 | 3/2010 |
| WO | WO 2010/044385 | 4/2010 |
| WO | WO 2010/063951 | 6/2010 |
| WO | WO 2011/028690 | 3/2011 |
| WO | WO 2011/035312 | 3/2011 |

OTHER PUBLICATIONS

U.S. Appl. No. 11/697,573 (US 2007/0276245), filed Apr. 6, 2007 (Nov. 29, 2007).
U.S. Appl. No. 11/697,579 (US 2007/0276242), filed Apr. 6, 2007 (Nov. 29, 2007).
U.S. Appl. No. 11/899,004 (U.S. Pat. No. 8,150,128), filed Aug. 30, 2007 (Apr. 3, 2012).
U.S. Appl. No. 12/077,612 (US 2009/0005711), filed Mar. 19, 2008 (Jan. 1, 2009).
U.S. Appl. No. 12/096,254 (US 2009/0221916), filed Nov. 26, 2008 (Sep. 3, 2009).
U.S. Appl. No. 13/019,029 (U.S. Pat. No. 8,428,687), filed Feb. 1, 2011 (Apr. 23, 2013).
U.S. Appl. No. 13/045,070 (US 2011/0295105), filed Mar. 10, 2011 (Dec. 1, 2011).
U.S. Appl. No. 13/353,148 (US 2013/0066211), filed Jan. 18, 2012 (Mar. 14, 2013).
U.S. Appl. No. 13/426,400 (US 2013/0046229), filed Mar. 21, 2012 (Feb. 21, 2013).
U.S. Appl. No. 13/529,239 (US 2013/0131495), filed Jun. 21, 2012 (May 23, 2013).
U.S. Appl. No. 13/848,436 (US 2013/0315491), filed Mar. 21, 2013 (Nov. 28, 2013).
U.S. Appl. No. 14/300,106 (US 2015/0010222), filed Jun. 9, 2014 (Jan. 8, 2015).
U.S. Appl. No. 14/091,010 (US 2014/0114216), filed Nov. 26, 2013 (Apr. 24, 2014).
U.S. Appl. No. 14/457,023 (US 2015/0045724), filed Aug. 11, 2014 (Feb. 12, 2015).
U.S. Appl. No. 11/433,510, dated Jul. 23, 2014 Issue Fee Payment.
U.S. Appl. No. 11/433,510, dated Apr. 23, 2014 Notice of Allowance.
U.S. Appl. No. 11/433,510, dated Apr. 7, 2014 Applicant Initiated Interview Summary.
U.S. Appl. No. 11/433,510, dated Apr. 4, 2014 Response to Non-Final Office Action.
U.S. Appl. No. 11/433,510, dated Oct. 4, 2013 Non-Final Office Action.
U.S. Appl. No. 11/433,510, dated Mar. 30, 2012 Request for Continued Examination (RCE).
U.S. Appl. No. 11/433,510, dated Mar. 28, 2012 Advisory Action.
U.S. Appl. No. 11/433,510, dated Dec. 29, 2011 Response to Final Office Action.
U.S. Appl. No. 11/433,510, dated Sep. 30, 2011 Final Office Action.
U.S. Appl. No. 11/433,510, dated May 23, 2011 Response to Non-Final Office Action.
U.S. Appl. No. 11/433,510, dated Jan. 21, 2011 Non-Final Office Action.
U.S. Appl. No. 11/433,510, dated Oct. 28, 2010 Response to Non-Final Office Action.
U.S. Appl. No. 11/433,510, dated Apr. 28, 2010 Non-Final Office Action.
U.S. Appl. No. 11/433,510, dated Apr. 13, 2010 Amendment and Request for Continued Examination (RCE).
U.S. Appl. No. 11/433,510, dated Nov. 12, 2009 Final Office Action.
U.S. Appl. No. 11/433,510, dated Aug. 6, 2009 Response to Non-Final Office Action.
U.S. Appl. No. 11/433,510, dated Mar. 17, 2009 Non-Final Office Action.
U.S. Appl. No. 11/697,573, dated Jan. 12, 2015 Notice of Abandonment.
U.S. Appl. No. 11/697,573, dated Jun. 16, 2014 Non-Final Office Action.
U.S. Appl. No. 11/697,573, dated Oct. 17, 2013 Final Office Action.
U.S. Appl. No. 11/697,573, dated Sep. 4, 2013 Response to Non-Final Office Action.
U.S. Appl. No. 11/697,573, dated May 10, 2013 Non-Final Office Action.
U.S. Appl. No. 11/697,573, dated Jan. 18, 2013 Amendment and Request for Continued Examination (RCE).
U.S. Appl. No. 11/697,573, dated Jul. 18, 2012 Final Office Action.
U.S. Appl. No. 11/697,573, dated Jun. 27, 2012 Response to Non-Final Office Action.
U.S. Appl. No. 11/697,573, dated Jan. 26, 2012 Non-Final Office Action.
U.S. Appl. No. 11/697,573, dated Aug. 18, 2011 Amendment and Request for Continued Examination (RCE).
U.S. Appl. No. 11/697,573, dated Mar. 18, 2011 Final Office Action.
U.S. Appl. No. 11/697,573, dated Dec. 22, 2010 Response to Non-Final Office Action.

(56) References Cited

OTHER PUBLICATIONS

U.S. Appl. No. 11/697,573, dated Jun. 23, 2010 Non-Final Office Action.
U.S. Appl. No. 11/697,579, dated Nov. 28, 2011 Notice of Abandonment.
U.S. Appl. No. 11/697,579, dated Apr. 29, 2011 Final Office Action.
U.S. Appl. No. 11/697,579, dated Feb. 7, 2011 Response to Non-Final Office Action.
U.S. Appl. No. 11/697,579, dated Aug. 6, 2010 Non-Final Office Action.
U.S. Appl. No. 11/697,579, dated May 17, 2010 Response to Non-Final Office Action.
U.S. Appl. No. 11/697,579, dated Nov. 17, 2009 Non-Final Office Action.
U.S. Appl. No. 11/697,579, dated Oct. 15, 2009 Amendment and Request for Continued Examination (RCE).
U.S. Appl. No. 11/697,579, dated Jul. 15, 2009 Response to Final Office Action.
U.S. Appl. No. 11/697,579, dated Apr. 15, 2009 Final Office Action.
U.S. Appl. No. 11/697,579, dated Jan. 16, 2009 Response to Non-Final Office Action.
U.S. Appl. No. 11/697,579, dated Jul. 18, 2008 Non-Final Office Action.
U.S. Appl. No. 11/899,004, dated Jan. 3, 2012 Issue Fee payment.
U.S. Appl. No. 11/899,004, dated Oct. 4, 2012 Amendment after Allowance.
U.S. Appl. No. 11/899,004, dated Oct. 3, 2012 Notice of Allowance.
U.S. Appl. No. 11/899,004, dated Nov. 3, 2011 Decision on Petition.
U.S. Appl. No. 11/899,004, dated Oct. 4, 2011 Petition and Amendment after Notice of Allowance.
U.S. Appl. No. 11/899,004, dated Oct. 3, 2011 Notice of Allowance.
U.S. Appl. No. 11/899,004, dated Sep. 23, 2011 Amendment and Request for Continued Examination (RCE).
U.S. Appl. No. 11/899,004, dated Sep. 19, 2011 Decision on Petition.
U.S. Appl. No. 11/899,004, dated Jul. 18, 2011 Notice of Allowance.
U.S. Appl. No. 11/899,004, dated May 10, 2011 Response to Non-Final Office Action.
U.S. Appl. No. 11/899,004, dated Feb. 8, 2011 Non-Final Office Action.
U.S. Appl. No. 12/077,612, dated Oct. 29, 2015 Notice of Abandonment.
U.S. Appl. No. 12/077,612, dated Apr. 9, 2015 Non-Final Office Action.
U.S. Appl. No. 12/077,612, dated Sep. 22, 2014 Amendment and Request for Continued Examination (RCE).
U.S. Appl. No. 12/077,612, dated Jan. 30, 2014 Response to Non-Final Office Action.
U.S. Appl. No. 12/077,612, dated Jan. 2, 2014 Applicant Initiated Interview Summary.
U.S. Appl. No. 12/077,612, dated Aug. 30, 2013 Non-Final Office Action.
U.S. Appl. No. 12/077,612, dated Oct. 26, 2011 Amendment and Request for Continued Examination (RCE).
U.S. Appl. No. 12/077,612, dated May 26, 2011 Final Office Action.
U.S. Appl. No. 12/077,612, dated Mar. 23, 2011 Response to Non-Final Office Action.
U.S. Appl. No. 12/077,612, dated Nov. 16, 2010 Non-Final Office Action.
U.S. Appl. No. 12/077,612, dated Mar. 21, 2014 Final Office Action.
U.S. Appl. No. 12/096,254, dated Sep. 28, 2015 Notice of Abandonment.
U.S. Appl. No. 12/096,254, dated Feb. 27, 2015 Non-Final Office Action.
U.S. Appl. No. 12/096,254, dated Sep. 22, 2014 Amendment and Request for Continued Examination (RCE).
U.S. Appl. No. 12/096,254, dated Dec. 23, 2013 Response to Non-Final Office Action.
U.S. Appl. No. 12/096,254, dated Dec. 17, 2013 Applicant Initiated Interview Summary.
U.S. Appl. No. 12/096,254, dated Aug. 23, 2013 Non-Final Office Action.
U.S. Appl. No. 12/096,254, dated Nov. 30, 2012 Amendment and Request for Continued Examination (RCE).
U.S. Appl. No. 12/096,254, dated May 31, 2012 Final Office Action.
U.S. Appl. No. 12/096,254, dated Apr. 4, 2012 Response to Non-Final Office Action.
U.S. Appl. No. 12/096,254, dated Oct. 5, 2011 Non-Final Office Action.
U.S. Appl. No. 12/096,254, dated Mar. 21, 2014 Final Office Action.
U.S. Appl. No. 13/019,029, dated Mar. 21, 2013 Issue Fee payment.
U.S. Appl. No. 13/019,029, dated Dec. 26, 2012 Notice of Allowance.
U.S. Appl. No. 13/045,070, dated Nov. 17, 2015 Response after Final Action.
U.S. Appl. No. 13/045,070, dated Jul. 7, 2015 Final Office Action.
U.S. Appl. No. 13/045,070, dated May 18, 2015 Applicant Initiated Interview Summary.
U.S. Appl. No. 13/045,070, dated May 15, 2015 Response to Non-Final Office Action.
U.S. Appl. No. 13/045,070, dated Jan. 16, 2015 Non-Final Office Action.
U.S. Appl. No. 13/045,070, dated Nov. 7, 2013 Amendment and Request for Continued Examination (RCE).
U.S. Appl. No. 13/045,070, dated May 9, 2013 Final Office Action.
U.S. Appl. No. 13/045,070, dated Dec. 21, 2012 Response to Non-Final Office Action.
U.S. Appl. No. 13/045,070, dated Jun. 22, 2012 Non-Final Office Action.
U.S. Appl. No. 13/353,148, dated Aug. 12, 2015 Non-Final Office Action.
U.S. Appl. No. 13/353,148, dated Jul. 6, 2015 Amendment and Request for Continued Examination (RCE).
U.S. Appl. No. 13/353,148, dated Mar. 3, 2015 Final Office Action.
U.S. Appl. No. 13/353,148, dated Oct. 24, 2014 Response to Non-Final Office Action.
U.S. Appl. No. 13/353,148, dated Oct. 14, 2014 Applicant Initiated Interview Summary.
U.S. Appl. No. 13/353,148, dated Apr. 24, 2014 Non-Final Office Action.
U.S. Appl. No. 13/353,148, dated Apr. 17, 2014 Amendment and Request for Continued Examination (RCE).
U.S. Appl. No. 13/353,148, dated Feb. 25, 2014 Applicant Initiated Interview Summary.
U.S. Appl. No. 13/353,148, dated Oct. 17, 2013 Final Office Action.
U.S. Appl. No. 13/353,148, dated Sep. 11, 2013 Response to Non-Final Office Action.
U.S. Appl. No. 13/353,148, dated Jun. 20, 2013 Non-Final Office Action.
U.S. Appl. No. 13/426,400, dated Dec. 4, 2015 Applicant Initiated Interview Summary.
U.S. Appl. No. 13/426,400, dated Dec. 4, 2015 Response to Non-Final Office Action.
U.S. Appl. No. 13/426,400, dated Jul. 2, 2015 Non-Final Office Action.
U.S. Appl. No. 13/426,400, dated Mar. 23, 2015 Amendment and Request for Continued Examination (RCE).
U.S. Appl. No. 13/426,400, dated Dec. 23, 2014 Final Office Action.
U.S. Appl. No. 13/426,400, dated Oct. 2, 2014 Response to Non-Final Office Action.
U.S. Appl. No. 13/426,400, dated May 5, 2014 Non-Final Office Action.
U.S. Appl. No. 13/529,239, dated Jun. 4, 2015 Final Office Action.
U.S. Appl. No. 13/529,239, dated Mar. 5, 2015 Applicant Initiated Interview Summary.
U.S. Appl. No. 13/529,239, dated Mar. 3, 2015 Response to Non-Final Office Action.
U.S. Appl. No. 13/529,239, dated Sep. 3, 2014 Non-Final Office Action.
U.S. Appl. No. 13/529,239, dated Jun. 30, 2014 Amendment and Request for Continued Examination (RCE).

(56) References Cited

OTHER PUBLICATIONS

U.S. Appl. No. 13/529,239, dated May 1, 2014 Applicant Initiated Interview Summary.
U.S. Appl. No. 13/529,239, dated Dec. 31, 2013 Final Office Action.
U.S. Appl. No. 13/529,239, dated Dec. 3, 2013 Response to Non-Final Office Action.
U.S. Appl. No. 13/529,239, dated Nov. 18, 2013 Applicant Initiated Interview Summary.
U.S. Appl. No. 13/529,239, dated Jul. 5, 2013 Non-Final Office Action.
"Vial", Retrieved from http://en.wikipedia.org/w/index.php?title=Vial&oldid=603936258 [Downloaded on May 20, 2014].
Abbott, et al., "Astrocyte-Endothelial Interactions at the Blood-Brain Barrier", *Nat. Rev. Neurosci.*, 7(1):41-53 (2006).
Ammi, et al., "Ultrasonic contrast agent shell rupture detected by inertial cavitation and rebound signals", *IEEE Transactions*, 53(1):126-136 (2006).
Ashikaga, et al., "Transmural Dispersion of Myofiber Mechanics: Implications for Electrical Heterogeneity In Vivo", *Journal of the American College of Cardiology*, 49(8):909-916 (2007).
Aubry, et al., "Experimental Demonstration of Noninvasive Transskull Adaptive Focusing Based on Prior Computed Tomography Scans", *The Journal of the Acoustical Society of America*, 113:84 (2003).
Avolio, et al., "Effects of aging on changing arterial compliance and left ventricular load in a northern Chinese urban community", *Circulation*, 68(1):50-58 (1983).
Azuma, et al., "Bubble Generation by Standing Wave in Water Surrounded by Cranium With Transcranial Ultrasonic Beam", *Japanese Journal of Applied Physics*, 44:4625-4630 (2005).
Badke, et al., "Effects of Ventricular Pacing on Regional Left Ventricular Performance in the Dog", *Am J Physiol Heart Circ Physiol.*, 238:H858-867 (1980).
Baron, et al., "Simulation of Intracranial Acoustic Fields in Clinical Trials of Sonothrombolysis", *Ultrasound Med. Biol.*, 35(7): 1148-1158 (2009).
Baseri, et al., "Multi-Modality Safety Assessment of Blood-Brain Barrier Opening Using Focused Ultrasound and Definity Microbubbles: A Short-Term Study", *Ultrasound Med. Biol.*, 6(9):1445-1459 (2010).
Behrens, et al., "Low-Frequency, Low-Intensity Ultrasound Accelerates Thrombolysis Through the Skull", *Ultrasound in Medicine & Biology*, 25:269-273 (1999).
Bercoff, et al., "Supersonic Shear Imaging: A New Technique for Soft Tissue Elasticity Mapping", *IEEE Transactions on Ultrasonics Ferroelectrics and Frequency Control*, 51:396-409 (2004).
Berger, et al., "Single-Beat Noninvasive Imaging of Cardiac Electrophysiology of Ventricular Pre-Excitation", *Journal of the American College of Cardiology*, 48:2045-2052 (2006).
Bers, "Cardiac Excitation-Contraction Coupling", *Nature*, 415:198-205 (2002).
Bonnefous, et al, "Time Domain Formulation of Pulse-Doppler Ultrasound and Blood Velocity Estimation by Cross Correlation", *Ultrason Imaging*, 8(2):73-85 (1986).
Borden et al., "Ultrasound Radiation Force Modulates Ligand Availability on Target Contrast Agents", Mol. Imaging, 5:139-147 (2006).
Brekke, et al., "Tissue Doppler Gated (TDOG) Dynamic Three-Dimensional Ultrasound Imaging of the Fetal Heart", *Ultrasound Obstet Gynecol.*, 24(2):192-198 (2004).
Brooks, et al., "Electrical Imaging of the Heart", *IEEE Signal Processing Magazine*, 14:24-42 (1997).
Brundin, et al., "Restorative Therapies in Parkinson's Disease", *Springer Verlag* (2006).
Campbell, et al., "Mechanisms of Transmurally Varying Myocyte Electromechanics in an Integrated Computational Model", *Philos Transact A Math Phys Eng Sci.*, 366:3361-3380 (2008).
Carman, et al., "Adenosine receptor signaling modulates permeability of the blood-brain barrier", The Journal of Neuroscience, 31(37):13272-13280 (2011).
Caskey, et al., "Direct Observations of Ultrasound Microbubble Contrast Agent Interaction With the Microvessel Wall", *J. Acoust. Soc. Amer.*, 122(2):1191-1200 (2007).
Caskey, et al., "Microbubble Oscillation in Tubes With Diameters of 12, 25, and 195 Microns", *Appl. Phys. Lett.*, 88(3):033902-1-033902-3 (2006).
Cavaglia, et al., "Regional Variation in Brain Capillary Density and Vascular Response to Ischemia", *Brain Res.*, 910(1-2):81-93 (2001).
Chan, "Transgenic Nonhuman Primates for Neurodegenerative Diseases", *Reproductive Biology and Endocrinology*, 2:39 (2004).
Chang, et al., "3-D US Frame Positioning Using Speckle Decorrelation and Image Registration", *Ultrasound in Medicine and Biology*, pp. 801-812 (2003).
Chen, et al., "The size of blood-brain barrier opening induced by focused ultrasound is dictated by the acoustic pressure", J. Cereb. Blood Flow Metab., 34:1197-1204 (2014).
Chen, et al., "Architectural Acoustics and Noise: Advancements and Best Practices in Instrumentation for Architectural Acoustics and Noise", *J. Acoust. Soc. Am.; 164th Meeting: Acoustical Society of America*, 132(3, Pt. 2):1977-2018 (Sep. 2012).
Chen, et al., "Engineering Acoustics and ASA Committee on Standards: Sound Intensity Measurements", *J. Acoust. Soc. Am.; 164th Meeting: Acoustical Society of America*, 132(3, Pt. 2):1984 (Sep. 2012).
Chen, et al., "Estimation of Displacement Vectors and Strain Tensors in Elastography Using Angular Insonifications", *IEEE Transactions on Medical Imaging*, 23(12):1479-1489 (2004).
Chen, et al., "Optimization of Ultrasound Parameters for Cardiac Gene Delivery of Adenoviral or Plasmid Deoxyribonucleic Acid by Ultrasound-Targeted Microbubble Destruction", *J. Amer. Coll. Cardiol.*, 42(2):301-308 (2003).
Choi, et al., "Feasibility of Transcranial, Localized Drug-Delivery in the Brain of Alzheimer's-Model Mice Using Focused Ultrasound", *2005 IEEE Ultrasonics Symposium*, pp. 988-991 (Sep. 18-21, 2005).
Choi, et al., "Microbubble-size dependence of focused ultrasound-induced blood-brain barrier opening in mice in vivo", *IEEE transactions on Biomedical Engineering*, 57(1):145-154 (2010).
Choi, et al., "Molecules of Various Pharmacologically-Relevant Sizes Can Cross the Ultrasound-Induced Blood-Brain Barrier Opening In Vivo", *Ultrasound in Medicine & Biology*, 36(1):58-67 (2009).
Choi, et al., "Noninvasive, Transcranial and Localized Opening of the Blood-Brain Barrier Using Focused Ultrasound in Mice", *Ultrasound in Medicine & Biology*, 33(1):95-104 (2007).
Choi, et al., "Spatio-Temporal Analysis of Molecular Delivery Through the Blood-Brain Barrier Using Focused Ultrasound", *Physics in Medicine and Biology*, 52:5509-5530, (2007).
Choi, et al., "Delivery of pharmacologically-relevant sized molecules through the ultrasound-induced blood-brain barrier opening in vivo", *Neuroscience, Chicago, IL, USA*, Oct. 17-21. 2009.
Choi, et al., "Focused Ultrasound-Induced Molecular Delivery Through the Blood-Brain Barrier", *Presented at the IEEE Symp. Ultrason. Ferroelect. Freq. Control, New York, NY*, pp. 1192-1195 (2007).
Choi, et al., "Noninvasive and Transient Blood-Brain Barrier Opening in the Hippocampus of Alzheimer's Double Transgenic Mice Using Pulsed Focused Ultrasound", *Ultrasonic Imaging*, pp. 189-200 (2008).
Choi, et al., "Optimization of Blood-Brain Barrier Opening in Mice using Focused Ultrasound", *2006 IEEE Ultrasounics Symposium* [online], Jun. 2007.
Chomas, et al., "Threshold of Fragmentation for Ultrasonic Contrast Agents", *J. Biomed. Opt.*, 6(2):141-150 (2001).
Clement, et al., "A Hemisphere Array for Non-Invasive Ultrasound Brain Therapy and Surgery", *Phys Med Biol.*, 45:3707-3719 (2000).
Cobbold, R.S.C., "Foundations of biomedical ultrasound", Biomedical engineering series, Oxford University Press, pp. 422-423(2006).
Connor, "Simulation Methods and Tissue Property Models for Non-Invasive Transcranial Focused Ultrasound Surgery", *Ph.D. Thesis* (2005).

(56) References Cited

OTHER PUBLICATIONS

Connor, et al., "A Unified Model for the Speed of Sound in Cranial Bone Based on Genetic Algorithm Optimization", *Physics in Medicine and Biology*, 47:3925-3944 (2002).
Cordeiro, et al., "Transmural Heterogeneity of Calcium Activity and Mechanical Function in the Canine Left Ventricle", *Am J Physiol. Heart Circ. Physiol.*, 286:H1471-1479 (2004).
Coyle, "Arterial Patterns of the Rat Rhinencephalon and Related Structures", *Exp. Neurol.*, 49(3): 671-690 (1975).
Coyle, "Spatial Features of the Rat Hippocampal Vascular System", *Exp. Neurol.*, 58(3): 549-561 (1978).
Coyle, "Vascular Patterns of the Rat Hippocampal Formation", *Exp. Neurol.*, 52(3): 447-458 (1976).
Crum, et al., "Bjerknes Forces on Bubbles in a Stationary Sound Field", *The Journal of the Acoustical Society of America*, 57(6): 1363-1370 (1975).
Cutnell, et al., (1998). Physics, Fourth Edition. New York. Table of Contents.
Daffertshofer, et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial", *Stroke*, 36:1441-146 (2005).
Damianou, et al., "Dependence of ultrasonic attenuation and absorption in dog soft tissues on temperature and thermal dose", *J Acoust Soc Am*, 102(1):628-634 (1997).
Datta, et al., "Correlation of Cavitation With Ultrasound Enhancement of Thrombolysis", *Ultrasound in Medicine & Biology*, 32(8): 1257-1267 (2006).
De Craene, et al., "Temporal diffeomorphic free-form deformation: Application to motion and strain estimation from 3D echocardiography", *Medical Image Analysis*, 16(2):427-450 (2012).
Declerck, et al., "Left ventricular motion reconstruction from planar tagged MR images: a comparison", *Phys Med Biol.*, 45(6): 1611-1632 (2000).
Deffieux, et al., "Transcranial Focused Ultrasound for Blood-Brain Barrier Opening—Numerical Simulations With In Vitro Validation in Human and Monkey Skulls", *Title page and Table of Contents for the AIUM Annual Convention*, San Diego, CA, (2010).
Definition of "spatial filter" retrieved from http://ww.onelook.com/ on May 26, 2015.
DeLong, "Primate Models of Movement Disorders of Basal Ganglia Origin", *Trends Neurosci.*, 13(7): 281-285 (1990).
DuBose, et al., "Confusion and Direction in Diagnostic Doppler Sonography", *Journal of Diagnostic Medical Sonography*, 25(3):173-177 (2009).
Duck, "Physical Properties of Tissue: A Comprehensive Reference Book", *Academic Press, London, UK*, 1990.
Duerinckx, et al., "In vivo acoustic attenuation in liver: correlations with blood tests and histology", *Ultrasound Imaging*, 14(5):405-413 (1988).
Durrer, et al., "Total Excitation of the Isolated Human Heart", *Circulation*, 41:899-912 (1970).
Edwards, et al., "Effects of Ischemia on Left-Ventricular Regional Function in the Conscious Dog", *American Journal of Physiology*, 240, H413-H420 (1981).
EPO Search Report and Opinion and Office Action for EP06840170.2 dated Dec. 7, 2009 and Mar. 8, 2010.
Epstein-Barasg, et al., A microcomposite hydrogel for repeated on-demand ultrasound-triggered drug delivery, Biomaterials, 31(19):5208-5217 (2010).
Erpelding, et al., "Bubble-Based Acoustic Radiation Force Using Chirp Insonation to Reduce Standing Wave Effects", *Ultrasound in Medicine & Biology*, 33(2):263-269 (2007).
European Search Report for EP Application No. 10838238, dated May 6, 2014.
Everbach, et al., "Cavitational Mechanisms in Ultrasound-Accelerated Thrombolysis at 1 Mhz", *Ultrasound in Medicine & Biology*, 26(7): 1153-1160 (2000).

Faris, et al., "Novel Technique for Cardiac Electromechanical Mapping With Magnetic Resonance Imaging Tagging and an Epicardial Electrode Sock", *Ann Biomed Eng.*, 31:430-440 (2003).
Farook, et al., "Preparation of Microbubble Suspensions by Co-Axial Electrohydrodynamic Atomization", *Med. Eng. Phys.*, 29(7): 749-754 (2007).
Fenster, et al., "Three-dimensional ultrasound imaging", *Phys Med Biol*, 46(5):R67-R99 (2001).
Feshitan et al., "Microbubble Size Isolation by Differential Centrifugation", *Journal of Colloid and Interface Science*, 329: 316-324 (2009).
Fiske, et al., "Special Focus Section: Gene Therapy for Parkinson's Disease", *Experimental Neurology*, 209:28-29 (2008).
Fry, "Transkull Transmission of an Intense Focused Ultrasonic Beam", *Ultrasound in Medicine & Biology*, 3, p. 179 (1977).
Fry, et al., "A Focused Ultrasound System for Tissue Volume Ablation in Deep Seated Brain Sites", *IEEE 1986 Ultrasonics Symposium*, pp. 1001-1004 (1986).
Fujii, et al., "A new method for attenuation coefficient measurement in the liver", *Journal of Ultrasound Medicine*, 21(7):783-788 (2002).
Fung, (1993). Biomechanics—Mechanical Properties of Living Tissues. New York. Table of Contents.
Ganan-Calvo, et al., "Perfectly Monodisperse Microbubbling by Capillary Flow Focusing", *Phys. Rev. Lett.*, 87(27) Pt 1: 274501-1-274501-4 (2001).
Gaud et al., "Acoustic Characterization of Single Ultrasound Contrast Agent Microbubbles", *The Journal of the Acoustic Society of America*, 124(6): 4091 (2008).
Ghosh, et al., "Cardiac Memory in Patients With Wolff-Parkinson-White Syndrome: Noninvasive Imaging of Activation and Repolarization Before and After Catheter Ablation", *Circulation*, 118:907-915 (2008).
Giacobini, "Alzheimer Disease, From Molecular Biology to Therapy", *Advances in Experimental Medicine and Biology*, 429:235-245 (1997).
Ginat, et al., "High-resolution ultrasound elastography of articular cartilage in vitro", Proceedings of the 28th IEEE EMBS Annual International Conference, New York City, USApp. 6644-6647 (Aug. 30-Sep. 3, 2006).
Greenstein, et al., "Mechanisms of Excitation-Contraction Coupling in an Integrative Model of the Cardiac Ventricular Myocyte", *Biophysical Journal*, 90:77-91 (2006).
Greenwald, "Pulse Pressure and Arterial Elasticity", *Qjm-an International Journal of Medicine*, 95(2): 107-112 (2002).
Gupta, et al., "Changes in Passive Mechanical Stiffness of Myocardial Tissue with Aneurysm Formation", *Circulation*, 89:2315-2326 (1994).
Gurev, et al., "Distribution of Electromechanical Delay in the Heart: Insights From a Three-Dimensional Electromechanical Model", *Biophysical Journal*, 99:745-754 (2010).
Gurev, et al., "In Silico Characterization of Ventricular Activation Pattern by Electromechanical Wave Imaging", *Supplement to Heart Rhythm.*, 6:S357 (2009).
Heimdal, et al., "Real-time Strain Rate Imaging of the Left Ventricle by Ultrasound", *J Am Soc EchocardioG.*, 11(11): 1013-1019 (1998).
Henderson, et al., "Series Elasticity of Heart Muscle During Hypoxia", *Cardiovascular Research*, 5:10-14 (1971).
Housden, et al., "Ultrasonic imaging of 3D displacement vectors using a simulated 2D array and beamsteering", *Ultrasonics*, 53(2):615-621 (2013).
Hsu, et al., "Noninvasive and targeted gene delivery into the brain using microbubble-facilitated focused ultrasound", *PLoS One* 8(2): e57682 (Feb. 2013).
Huang, et al. "Watershed Segmentation for Breast Tumor in 2-D Sonography", *Ultrasound in Medicine and Biology*, pp. 625-632 (2004).
Hynynen, et al., "Demonstration of Potential Noninvasive Ultrasound Brain Therapy Through an Intact Skull", *Ultrasound in Medicine & Biology*, 24(2): 275-283 (1998).
Hynynen, et al., "Noninvasive MR Imaging—Guided Focal Opening of the Blood-Brain Barrier in Rabbits", *Radiology*, 220(3): 640-646 (2001).

(56) References Cited

OTHER PUBLICATIONS

Hynynen, et al., "Trans-Skull Ultrasound Therapy: The Feasibility of Using Image-Derived Skull Thickness Information to Correct the Phase Distortion", *IEEE Transactions on Ultrasonics, Ferroelectrics and Frequency Control*, 46(3): 752-755, (1999).
Hynynen, et al., "Focal Disruption of the Blood-Brain Barrier Due to 260-Khz Ultrasound Bursts: A Method for Molecular Imaging and Targeted Drug Delivery", *J. Neurosurg.*, 105(3): 445-454 (2006).
International Preliminary Report on Patentability, dated Apr. 17, 2007 and Written Opinion for PCT/US2005/037669, dated Jun. 13, 2006.
International Preliminary Report on Patentability, dated Apr. 17, 2007 and Written Opinion for PCT/US2005/037670, dated Nov. 22, 2006.
International Preliminary Report on Patentability, dated Jun. 11, 2008 and Written Opinion for PCT/US2006/061809, dated Oct. 4, 2007.
International Preliminary Report on Patentability, dated Nov. 14, 2007 and Written Opinion for PCT/US2006/018454, dated Aug. 9, 2007.
International Search Report and Written Opinion for PCT/US2006/036460, dated Sep. 5, 2007; International Preliminary Report dated Mar. 26, 2008.
International Search Report and Written Opinion for PCT/US2009/056513, dated Oct. 30, 2009.
International Search Report and Written Opinion for PCT/US2009/052563 dated Oct. 8, 2009.
International Search Report and Written Opinion for PCT/US2009/056565 dated Nov. 2, 2009.
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2011/034704, dated Aug. 18, 2011.
International Search Report for PCT/US2007/019149 dated Feb. 29, 2008.
Jagannathan, et al., "High-Intensity Focused Ultrasound Surgery of the Brain: Part 1-A Historical Perspective With Modern Applications", *Neurosurgery*, 64(2): 201-211 (2009).
Jasaityte, et al., "Current state of three-dimensional myocardial strain estimation using echocardiography", *J Am Soc Echocardiogr.*, 26(1):15-28 (2013).
Jensen, et al., "Calculation of Pressure Fields From Arbitrarily Shaped, Apodized, and Excited Ultrasound Transducers", *IEEE Transactions on Ultrasonics, Ferroelectrics and Frequency Control*, 39(2): 262-267 (1992).
Kallel, et al., "A Least-Squares Strain Estimator for Elastography", *Ultrasonic Imaging*, 19:195-208 (1997).
Kanai, et al. "Propagation of Spontaneously Actuated Pulsive Vibration in Human Heart Wall and In Vivo Viscoelasticity Estimation", *IEEE Transactions on Ultrasonics, Ferroelectrics, and Frequency Control*, 52(11): 1931-1942 (2005).
Kanai, et al., "A New Method for Measuring Small Local Vibrations in the Heart Using Ultrasound", *IEEE Transactions on Biomedical Engineering*, 40(12): 1233-1242 (1993).
Kanai, et al., "Myocardial Rapid Velocity Distribution", *Ultrasound Med Biol.*, 27(4): 481-498 (2001).
Kanai, et al., "Transcutaneous Measurement of Frequency Dispersion in the Regional Pulse Wave Velocity", *2000 IEEE Ultrasonics Symposium*, pp. 1-4 (2000).
Kaufman, et al., "Ultrasound Simulation in Bone," *IEEE Transactions on Ultrasonics Ferroelectrics and Frequency Control*, 55(6): 1205-1218 (2008).
Kawabata, et al., "Chemo-thermal approach for efficient ultrasonic tumor treatment with phase change nano droplet", *IEEE Int. Ultrasonics Symp.*, Oct. 18-21, 2011 Orlando, Florida, pp. 9-12.

Kimber, et al., "A Comparison of Unipolar and Bipolar Electrodes During Cardiac Mapping Studies", *Pacing Clin Electro.*, 19:1196-1204 (1996).
Kinoshita, et al., "Noninvasive Localized Delivery of Herceptin to the Mouse Brain by MRI-Guided Focused Ultrasound-Induced Blood-Brain Barrier Disruption", *Proceedings of the National Academy of Sciences*, 103(31): 11719-11723 (2006).
Kinoshita, et al., "Targeted Delivery of Antibodies Through the Blood—Brain Barrier by MRI-Guided Focused Ultrasound", *Biochemical and Biophysical Research Communications*, 340: 1085-1090 (2006).
Kim, et al., "Multifunctional microbubbles and nanobubbles for photoacoustic and ulstrasound imaging", *J Biomed Opt.*, 15(1): 010510-1-010510-3 (Jan./Feb. 2010).
Klein, et al., "Interdependency of Local Capillary Density, Blood Flow, and Metabolism in Rat Brains", *Amer. J. Physiol.*, 251(6) Pt 2: H1333-H1340 (1986).
Klempner, et al., "Neutrophil Plasma Membranes I. High-Yield Purification of Human Neutrophil Plasma Membrane Vesicles by Nitrogen Cavitation and Differential Centrifugation", *Journal of Cell Biology*, 86:21-28 (1980).
Konofagou et al., "Electromechanical Wave Imaging for Noninvasive Mapping of the 3D Electrical Activation Sequence in Canines and Humans In Vivo", Journal of Biomechanics, 45(5):856-864 (2012).
Konofagou, et al. "Elastographic Imaging of the Strain Distribution at the Anterior Cruciate Ligament and ACL-Bone Insertions", *Proceedings of the 2005 IEEE 27th Annual International Conference of the Engineering in Medicine and Biology Society*, pp. 972-975 (Shanghai, China Sep. 1-4, 2005).
Konofagou, et al., "Ultrasound-Induced Blood-Brain Barrier Opening", Current Pharmaceutical Biotechnology, 13(7):1332-1345 (2012).
Konofagou, et al., "A New Elastographic Method for Estimation and Imaging of Lateral Strains, Corrected Axial Strains and Poison's Ratios in Tissues", *Ultrasound in Medicine and Biology*, 24(8):1183-1199 (1998).
Konofagou, et al., "Mechanism and Safety at the Threshold of the Blood-Brain Barrier Opening In Vivo", *International Society on Therapeutic Ultrasound (ISTU), Aix-en-Provence, France*, Sep. 21-24, 2009.
Konofagou, et al., "Myocardial Elastography—Feasibility Study In Vivo", *Ultrasound Med & Biol.*, 28(4):475-482 (2002).
Konofagou, et al., "Noninvasive electromechanical wave imaging and conduction-relevant velocity estimation in vivo", *Ultrasonics*, 50(2):208-215 (2010).
Konofagou, et al., "Noninvasive Electromechanical Wave Imaging and Conduction Velocity Estimation In Vivo", *2007 IEEE Ultrasonics Symposium*, pp. 969-972 (2007).
Konofagou, et al., "Three-Dimensional Motion Estimation in Elastography", *IEEE Proceedings of the Symposium of Ultrasonics, Ferroelectrics and Frequency Control in Sendai, Japan*, pp. 1745-1748 (1998).
Korecka, et al., "Cell-Replacement and Gene-Therapy Strategies for Parkinson's and Alzheimers Disease", *Regen. Med.*, 2(4): 425-446 (2007).
Kremkau, et al., "Ultrasonic Attenuation and Propagation Speed in Normal Human Brain", *The Journal of the Acoustical Society of America*, 70:29 (1981).
Kunz, et al., "The Finite Difference Time Domain Method for Electromagnetics," *CRC Press, Boca Raton, USA* (1993).
Kvale, et al., "Size Fractionation of Gas-Filled Microspheres by Flotation", *Separations Technol.*, 6(4): 219-226 (1996).
Lai, et al., "Introduction to Continuum Mechanics" (Pergamon Pr). 3rd Ed. (1993).
Lee, et al., "Improving Stereotactic Surgery Using 3-D Reconstruction", *IEEE Engineering in Medicine and Biology Magazine*, 21:109-116 (2002).
Lee, et al., "Theoretical Quality Assessment of Myocardial Elastography With In Vivo Validation", *IEEE Transactions, Ultrasonics, Ferroelectrics and Frequency Control*, 54:2233-2245 (2007).

(56) References Cited

OTHER PUBLICATIONS

Liu, et al., "Hemorrhage Detection During Focused-Ultrasound Induced Blood-Brain-Barrier Opening by Using Susceptibility-Weighted Magnetic Resonance Imaging", *Ultrasound in Med. & Biol.*, 34(4): 598-606 (2008).

Liu, et al., "Magnetic Resonance Imaging Enhanced by Superparamagnetic Iron Oxide Particles: Usefulness for Distinguishing Between Focused Ultrasound-Induced Blood-Brain Barrier Disruption and Brain Hemorrhage", *J. of Magnetic Resonance Imaging*, 29:31-38 (2009).

Lu, et al., "Design and Experiment of 256-Element Ultrasound Phased Array for Noninvasive Focused Ultrasound Surgery", *Ultrasonics*, 44:e325-e330 (2006).

Luo, et al., "A Fast Normalized Cross-Correlation Method for Motion Estimation", *IEEE Transactions, Ultrasonics, Ferroelectrics and Frequency Control*, 57(6): 1347-1357 (2010).

Luo, et al., "High-Frame Rate, Full-View Myocardial Elastography With Automated Contour Tracking in Murine Left Ventricles In Vivo", *IEEE Transactions, Ultrasonics, Ferroelectrics and Frequency Control*, 55(1): 240-248 (2008).

Luo, et al., "Myocardial Elastography At Both High Temporal and Spatial Resolution for the Detection of Infarcts", *Ultrasound Med. Biol.*, 33(8): 1206-1223 (2007).

Luo, et al., "Pulse Wave Imaging of Normal and Aneurysmal Abdominal Aortas In Vivo", *IEEE Trans. Med. Imaging*, 28(4): 477-486 (2009).

Maleke, et al., "In Vivo Feasibility of Real-Time Monitoring of Focused Ultrasound Surgery (FUS) Using Harmonic Motion Imaging (HMI)", *IEEE Trans. Biomed. Eng.*, 57(1): 7-11 (2010).

Maleke, et al., "Single-Element Ultrasound Focused Transducer Method for Harmonic Motion Imaging", *Ultrasonic Imaging*, 28(3): 144-158 (2006).

Marquet, et al., "Non-Invasive Transcranial Ultrasound Therapy Based on a 3D CT Scan: Protocol Validation and In Vitro Results", *Phys. Med. Biol.*, 54:2597-2613 (2009).

Mazziotta, et al., "A Probabilistic Atlas of the Human Brain: Theory and Rationale for Its Development the International Consortium for Brain Mapping (ICBM)", *Neuroimage*, 2:89-101 (1995).

McDannold, et al., "Targeted Disruption of the Blood-Brain Barrier With Focused Ultrasound: Association With Cavitations Activity", *Physics in Medicine and Biology*, 51:793-808 (2006).

McDannold, et al., "Use of Ultrasound Pulses Combined With Definity for Targeted Blood-Brain Barrier Disruption: A Feasibility Study", *Ultrasound in Medicine & Biology*, 33(4): 584-590 (2007).

McDannold, et al., "Blood-Brain Barrier Disruption Induced by Focused Ultrasound and Circulating Preformed Microbubbles Appears to be Characterized by the Mechanical Index", *Ultrasound Med Biol.*, 34(5):834-840 (2008).

McDannold, et al., "MRI-Guided Targeted Blood-Brain Barrier Disruption With Focused Ultrasound: Histological Findings in Rabbits", *Ultrasound Med. Biol.*, 31(11): 1527-1537 (2005).

McLaughlin, et al., "Piezoelectric Sensor Determination of Arterial Pulse Wave Velocity", *Physiol Meas.*, 24(3): 693-702 (2003).

McNally, et al., "Computer Vision Elastography: Speckle Adaptive Motion Estimation for Elastography Using Ultrasound Sequences", *IEEE Transactions on Medical Imaging*, 24(6):755-766 (2005).

Melodelima, et al., "Thermal Ablation by High-Intensity-Focused Ultrasound Using a Toroid Transducer Increases the Coagulated Volume. Results of Animal Experiments", *Ultrasound in Medicine & Biology*, 35(3): 425-435 (2009).

Mitri, et al., "Chirp Imaging Vibro-Acoustography for Removing the Ultrasound Standing Wave Artifact", *IEEE Transactions on Medical Imaging*, 24(10): 1249-1255 (2005).

Mychaskiw, et al., "Optison (FS069) Disrupts the Blood-Brain Barrier in Rats", *Anesthesia & Analgesia*, 91:798 (2000).

Nichols, et al., "Vascular Impedance. In McDonald's: Blood Flow in Arteries: Theoretical, Experimental and Clinical Principles", *E. Arnold. London, Oxford University Press*, Table of Contents (1998).

Ophir, et al., "Elastography: A Quantitative Method for Imaging the Elasticity of Biological Tissues", *Ultrasonic Imaging*, 3(2): 111-134 (1991).

Otani, et al., "Transmural Ultrasound-Based Visualization of Patterns of Action Potential Wave Propagation in Cardiac Tissue", *Annals Biomedical Engineering*, 38(10):3112-3123 (2010).

Otani, "Use of ultrasound imaging to map propagating action potential waves in the heart", *Computers in Cardiology*, 36:617-620 (2009).

Palmeri, et al., "Characterizing acoustic attenuation of homogeneous media using focused impulsive acoustic radiation force", *Ultrason Imaging*, 28(2):114-128 (2006).

Papadakis, Emmauel P., "Ultrasonic Instruments & Devices", Academic Press, 8 pages (1999).

Pardridge, "Drug Targeting to the Brain", *Pharmaceutical Research*, 24:1733-1744 (2007).

Pardridge, "The Blood-Brain Barrier: Bottleneck in Brain Drug Development", *NeuroRx*, 2:3-14 (2005).

Patel, et al., "GDNF Delivery for Parkinson's Disease", *ACTA Neurochirurgica-Supplementum*, 97(2): 135-154 (2007).

Pernot, et al., "ECG-Gated, Mechanical and Electromechanical Wave Imaging of Cardiovascular Tissues In Vivo", *Ultrasound in Medicine & Biology*, 33(7):1075-1085 (2007).

Pernot, et al., "Electromechanical Imaging of the Myocardium at Normal and Pathological States", *2005 IEEE Ultrasonics Symposium*, pp. 1091-1094 (2005).

Philippens, "Non-Human Primate Models for Parkinson's Disease", *Drug Discovery Today: Disease Models*, 5:105-111 (2008).

Pichardo, et al., "Multi Frequency Characterization of Speed of Sound for Longitudinal Transmission on Freshly Excised Human Skulls" *9th International Society on Therapeutic Ultrasound*, p. 136 (2009.).

Prinzen, et al., "The Time Sequence of Electrical and Mechanical Activation During Spontaneous Beating and Ectopic Stimulation", *Eur. Heart J.*, 13:535-543 (1992).

Provost, et al., "Electromechanical Wave Imaging of Normal and Ischemic Hearts In Vivo", *IEEE Trans. Med. Imaging*, 29:625-635 (2010).

Provost, et al., "Imaging the electromechanical activity of the heart in vivo", *PNAS*, 108(21):8565-8570 (2011).

Provost, et al., "Mapping of cardiac electrical activation with electromechanical wave imaging: An in silico-in vivo reciprocity study", *Heart Rhythm.*, 8(5):752-759 (2011).

Qin, et al., "Acoustic Response of Compliable Microvessels Containing Ultrasound Contrast Agents", *Phys. Med. Biol.*, 51:5065-5088 (2006).

Qin, et al., "The Natural Frequency of Nonlinear Oscillation of Ultrasound Contrast Agents in Microvessels", *Ultrasound in Med. & Biol.*, 33(7):1140-1148 (2007).

Ramanathan, et al., "Activation and Repolarization of the Normal Human Heart Under Complete Physiological Conditions", *Proceedings of the National Academy of Sciences*, 103:6309-6314 (2006).

Ramanathan, et al., "Noninvasive Electrocardiographic Imaging for Cardiac Electrophysiology and Arrhythmia", *Nat Med.*, 10:422-428 (2004).

Raymond, et al., "Ultrasound Enhanced Delivery of Molecular Imaging and Therapeutic Agents in Alzheimer's Disease Mouse Models", *PLoS One*, 3(5):e2175 (2008).

Rice, et al., "Approximate Model of Cooperative Activation and Crossbridge Cycling in Cardiac Muscle Using Ordinary Differential Equations", *Biophys. J.*, 95:2368-2390 (2008).

Rockenstein, et al., "Transgenic Animal Models of Neurodegenerative Diseases and Their Application to Treatment Development", *Adv. Drug Del. Rev.*, 59(11):1093-1102 (2007).

Rogers, et al., "Age-Associated Changes in Regional Aortic Pulse Wave Velocity", *J Am Coll Cardiol.*, 38(4):1123-1129 (2001).

Roth, "Influence of a Perfusing Bath on the Foot of the Cardiac Action Potential", *Circulation Research*, 86:E19-E22 (2000).

Sabraoui, et al., "Feedback Loop Process to Control Acoustic Cavitation", *Ultrasonics Sonochemistry*, 18(2):589-594 (2011).

Samuel, et al., "An Ex Vivo Study of the Correlation Between Acoustic Emission and Microvascular Damage", *Ultrasound Med. Biol.*, 35(9):1574-1586 (2009).

(56) References Cited

OTHER PUBLICATIONS

Sanberg, et al., "Brief Communication: Neural Transplants Disrupt the Blood-Brain Barrier and Allow Peripherally Acting Drugs to Exert a Centrally Mediated Behavioral Effect", *Experimental Neurology*, 102:149-152 (1988).
Sandrin, et al., "Time-Resolved Pulsed Elastography with Ultrafast Ultrasonic Imaging", *Ultrason. Imaging*, 21(4): 259-72 (1999).
Sarvazyan, et al., "Shear Wave Elasticity Imaging: A New Ultrasonic Technology of Medical Diagnostics", *Ultrasound Med Biol.*, 24(9): 1419-1435 (1998).
Sassaroli, et al., "Cavitation Threshold of Microbubbles in Gel Tunnels by Focused Ultrasound", *Ultrasound in Med. & Biol.*, 33(10):1651-1660 (2007).
Sassaroli, et al., "Forced Linear Oscillations of Microbubbles in Blood Capillaries", *J. Acoust. Soc. Am.*, 115(6):3235-3243 (2004).
Sassaroli, et al., "Resonance Frequency of Microbubbles in Small Blood Vessels: a Numerical Study", *Phys. Med. Biol.*, 50:5293-5305 (2005).
Schenk, et al., "Immunization With Amyloid-Beta Attenuates Alzheimer-Disease-Like Pathology in the PDAPP Mouse", *Nature*, 400:173-177 (1999).
Scher, et al., "The Pathway of Ventricular Depolarization in the Dog", *Circ Res.*, 4:461-469 (1956).
Schilling, et al., "Simultaneous Endocardial Mapping in the Human Left Ventricle Using a Noncontact Catheter: Comparison of Contact and Reconstructed Electrograms During Sinus Rhythm", *Circulation*, 98:887-98 (1998).
Sengupta, et al., "Electromechanical Activation Sequence in Normal Heart", *Heart Fail Clin.*, 4:303-314 (2008).
Shehata, et al., "Myocardial Tissue Tagging With Cardiovascular Magnetic Resonance", *Journal of Cardiovascular Magnetic Resonance*, 11:55 (2009).
Sheikov, et al., "Brain Arterioles Show More Active Vesicular Transport of Blood-Borne Tracer Molecules Than Capillaries and Venules After Focused Ultrasound-Evoked Opening of the Blood-Brain Barrier", *Ultrasound Med. Biol.*, 32(9): 1399-1409 (2006).
Sheikov, et al., "Cellular Mechanisms of the Blood-Brain Barrier Opening Induced by Ultrasound in Presence of Microbubbles", *Ultrasound Med. Biol.*, 30(7): 979-989 (2004).
Sheikov, et al., "Effect of Focused Ultrasound Applied With an Ultrasound Contrast Agent on the Tight Junctional Integrity of the Brain Microvascular Endothelium", *Ultrasound Med. Biol.*, 34(7): 1093-1104 (2008).
Shiinna, et al., "Realtime tissue elasticity imaging using the combined autocorrelation method", *J. Med. Ultrasonics*, 29(autumn):119-128 (2002).
Siegel, et al., "Neurotrophic Factors in Alzheimer's and Parkinson's Disease Brain", *Brain Research Reviews*, 33:199-227 (2000).
Silva, "Nanotechnology Approaches to Crossing the Blood-Brain Barrier and Drug Delivery to the CNS", *BMC Neruosci.*, 9(Suppl 3): S4 (2008).
Sinkus, et al., "High-Resolution Tensor MR Elastography for Breast Tumour Detection", *Phys Med Biol.*, 45(6): 1649-1664 (2000).
Sirsi, et al., "Effect of Microbubble Size on Fundamental Mode High Frequency Ultrasound Imaging in Mice", *Ultrasound in Med. & Bio.*, 36(6): 935-948 (2010).
Spach, et al., "Extracellular Discontinuities in Cardiac Muscle—Evidence for Capillary Effects on the Action Potential Foot", *Circulation Research*, 83:1144-1164 (1998).
Stewart, et al., "Blood-Eye Barriers in the Rat: Correlation of Ultrastructure With Function", *J. Comp. Neurol.*, 340(4): 566—576 (1994).
Stieger, et al., "Enhancement of Vascular Permeability With Low-Frequency Contrast-Enhanced Ultrasound in the Chorioallantoic Membrane Model", *Radiology*, 243(1): 112-121 (2007).
Styner, et al., "Automatic Brain Segmentation in Rhesus Monkeys" *2007 Medical Imaging, Proc. of SPIE*, 6512:65122L-1-65122L-8 (2007).
Sutherland, "Color Doppler Myocardial Imaging—Potential Applications in Acquired and Congenital Heart-Disease", *Acta Paediatr.*, 84:40-48 (1995).
Sykova, et al., "Diffusion in Brain Extracellular Space", *Physiol. Rev.*, 88(4): 1277-1340 (2008).
Talu, et al., "Tailoring the Size Distribution of Ultrasound Contrast Agents: Possible Method for Improving Sensitivity in Molecular Imaging" *Mol. Imag.*, 6(6): 384-392 (2007).
Tang, et al., "Standing-Wave Suppression for Transcranial Ultrasound by Random Modulation", *IEEE transactions on Biomedical Engineering*, 57(1):203-205 (2010).
Tanter, et al., "Focusing and Steering Through Absorbing and Aberrating Layers: Application to Ultrasonic Propagation Through the Skull", *The Journal of the Acoustical Society of America*, 103:2403-2410 (1998).
Tanter, et al., "Ultrafast Compound Imaging for 2-D Motion Vector Estimation: Application to Transient Elastography", *IEEE Trans Ultrason Ferroelectr Freq Control*, 49(10): 1363-74 (2002).
Tavarozzi, et al., "Magnetocardiography: Current Status and Perspectives Part II: Clinical Applications", *Ital Heart J.*, 3:151-165 (2002).
Techavipoo, et al., "Temperature dependence of ultrasonic propagation speed and attenuation in excised canine liver tissue measured using transmitted and reflected pulses", *The Journal of Acoustical Society of America*, 115(6):2859-2865 (2004).
Treat, et al., "Targeted Delivery of Doxorubicin to the Rat Brain at Therapeutic Levels Using MRI-Guided Focused Ultrasound", *Int. J. Cancer*, 121(4): 901-907 (2007).
Tung, et al., "Feasibility of Noninvasive Cavitation-Guided Blood-Brain Barrier Opening Using Focused Ultrasound and Microbubbles in Nonhuman Primates", *Applied Physics Letters*, 98(16):163704 (2001).
Tung, et al., "Identifying the Inertial Cavitation Threshold and Skull Effects in a Vessel Phantom Using Focused Ultrasound and Microbubbles", *Ultrasound in Medicine & Biology*, 36(5): 840-852 (2010).
Tung, et al., "Identifying the Inertial Cavitation Threshold in a Vessel Phantom Using Focused Ultrasound and Microbubbles", *The Journal of the Acoustical Society of America*, 124:2486 (2008).
Tung, et al., "Noninvasive In Vivo Cavitation Threshold Detection During Blood-Brain Barrier Opening Using Focused Ultrasound and the Contrast Agent and Definity", *Joint 159th Meeting of the Acoustic Society of America*, (Apr. 19, 2010).
Tuszynski, et al., "A Phase 1 Clinical Trial of Nerve Growth Factor Gene Therapy for Alzheimer Disease", *Nature Medicine*, 11:551-555 (2005).
Tuszynski, et al., "Nerve Growth Factor Gene Therapy in Alzheimer Disease" *Alzheimer Disease & Associated Disorders*, 21:179-189 (2007).
Unger, E.C. et al., "Therapeutic Applications of Lipid-Coated Microbubbles", *Advanced Drug Delivery Reviews*, 56(9):1291-1314 (2004).
Vappou, et al., "Quantitative Viscoelastic Parameters Measured by Harmonic Motion Imaging", *Phys. Med. Biol.*, 54:3579-3595 (2009).
Walker, et al., "A Fundamental Limit on Delay Estimation Using Partially Correlated Speckle Signals", *IEEE Transactions, Ultrasonics, Ferroelectrics and Frequency Control*, 42(2): 301-308 (1995).
Walker, et al., "A Fundamental Limit on the Performance of Correlation Based Phase Correction and Flow Estimation Techniques", *IEEE Transactions, Ultrasonics, Ferroelectrics and Frequency Control*, 41(5): 644-654 (1994).
Wang et al., "Qualitative and Quantitative Analysis of the Molecular Delivery Through the Ultrasound-Enhanced Blood-Brain Barrier Opening in the Murine Brain," presented at the *IEEE Symp. Ultrason. Ferroelectr. Freq. Control*, Beijing, China, 2008.
Wang, et al., "A Composite Imaging Technique for High Frame-Rate and Full-View Cardiovascular Ultrasound and Elasticity Imaging", *IEEE Transactions, Ultrasonics, Ferroelectrics and Frequency Control*, 55(10): 2221-2233 (2008).

(56) References Cited

OTHER PUBLICATIONS

Wang, et al., "A Composite Imaging Technique for High Frame-Rate and Full-View Cardiovascular Ultrasound and Elasticity Imaging", *IEEE International Ultrasonics Symposium, New York, NY*, Oct. 28-31, 2007.
Wang, et al., "Increased Aortic Stiffness Assessed by Pulse Wave Velocity in Apolipoprotein E-Deficient Mice", *Am J Physiol Heart Circ Physiol.*, 278(2): H428-34 (2000).
Wenk, "A Primate Model of Alzheimer's Disease", *Behavioural Brain Research*, 57:117-122 (1993).
White, et al., "Longitudinal and Shear Mode Ultrasound Propagation in Human Skull Bone", *Ultrasound In Medicine& Biology*, 32:1085-1096 (2006).
Wyman, et al., "Mapping Propagation of Mechanical Activation in the Paced Heart With MRI Tagging", *Am J Physiol Heart Circ Physiol*, 32:1085-1096 (2006).
Xu, et al., "Controllable Gas-Liquid Phase Flow Patterns and Monodisperse Microbubbles in a Microfluidic T-Junction Device", *Appl. Phys. Lett.*, 88(13): 133506-1-133506-3 (2006).
Yin, et al., "A Numerical Study of Transcranial Focused Ultrasound Beam Propagation at Low Frequency", *Physics in Medicine and Biology*, 50:1821-1836 (2005).
Yuh, et. al. "Delivery of Systemic Chemotherapeutic Agent to Tumors by Using Focused Ultrasound: Study in a Murine Model", *Radiology*, 234(2): 431-437 (2005).
Zerhouni, et al., "Human Heart: Tagging with MR Imaging—A Method for Noninvasive Assessment of Myocardial Motion", *Radiology*, 169(1): 59-63 (1988).
Zhang, et al., "Noninvasive Three-Dimensional Electrocardiographic Imaging of Ventricular Activation Sequence", *Am J Physiol Heart Circ Physiol.*, 289:H2724-32 (2005).
Zheng, et al. "High Resolution Ultrasound Elastomicroscopy Imaging of Soft Tissues: System Development and Feasibility; Ultrasound Elastomicroscopy", *Physics in Medicine and Biology*, 49(17):3925-3938 (2004).
Zheng, et al., "Ultrasonic measurement of depth-dependent transient behaviors of articular cartilage under compression", Journal of Biomechanics, 38:1830-1837 (2005).
Zheng, et al., "Ultrasound-Driven Microbubble Oscillation and Translation Within Small Phantom Vessels", *Ultrasound Med. Biol.*, 33(12): 1978-1987 (2007).
Zlokovic, "The Blood-Brain Barrier in Health and Chronic Neurodegenerative Disorders", *Neuron*, 57(2): 178-201 (2008).
Zwanenburg, et al., "Timing of Cardiac Contraction in Humans Mapped by High-Temporal-Resolution MRI Tagging: Early Onset and Late Peak of Shortening in Lateral Wall", *Am J Physiol Heart Circ Physiol.*, 286:H1872-1880 (2004).
U.S. Appl. No. 11/433,510(U.S. Pat. No. 8,858,441), filed May 12, 2006 (Oct. 14, 2014).
U.S. Appl. No. 21/096,254, dated Mar. 21, 2014 Final Office Action.
U.S. Appl. No. 13529,239, dated May 1, 2014 Applicant Initiated Interview Summary.
U.S. Appl. No. 14/949,000 (US 2016/0074678), filed Nov. 23, 2015 (Mar. 17, 2016).
U.S. Appl. No. 14/457,023, dated Mar. 2, 2016 Non-Final Office Action.
U.S. Appl. No. 15/165,942, filed May 26, 2016.
U.S. Appl. No. 13/426,400, dated May 5, 2016 Issue Fee Payment.
U.S. Appl. No. 13/426,400, dated May 13, 2016 Notice of Allowance.
U.S. Appl. No. 13/848,436, dated Nov. 1, 2016 Issue Fee Payment.
U.S. Appl. No. 13/848,436, dated Aug. 2, 2016 Notice of Allowance.
U.S. Appl. No. 13/848,436, dated Jun. 21, 2016 Response to Non-Final Office Action.
U.S. Appl. No. 14/091,010, dated Sep. 12, 2016 Non-Final Office Action.
U.S. Appl. No. 14/457,023, dated Jun. 30, 2016 Response to Non-Final Office Action.
U.S. Appl. No. 14/457,023, dated Sep. 9, 2016 Final Office Action.
Extended European Search Report dated Jan. 23, 2017 in EP Application No. 10818027.
U.S. Appl. No. 14/949,000 (US 2016/0074678), filed Nov. 23, 2015( Mar. 17, 2016).
U.S. Appl. No. 13/045,070, dated Feb. 24, 2016 Issue Fee Payment.
U.S. Appl. No. 13/045,070, dated Jan. 15, 2016 Notice of Allowance.
U.S. Appl. No. 13/045,070, dated Jan. 15, 2016 Applicant Initiated Interview Summary.
U.S. Appl. No. 13/045,070, dated Jan. 7, 2016 Notice of Appeal Filed.
U.S. Appl. No. 13/353,148, dated Feb. 26, 2016 Notice of Abandonment.
U.S. Appl. No. 13/426,400, dated Feb. 5, 2016 Notice of Allowance.
U.S. Appl. No. 13/529,239, dated Jan. 8, 2016 Notice of Abandonment.
U.S. Appl. No. 13/848,436, dated Jan. 21, 2016 Non-Final Office Action.
U.S. Appl. No. 13/848,436, dated Dec. 21, 2015 Response to Restriction Requirement.
U.S. Appl. No. 13/848,436, dated Jul. 22, 2015 Restriction Requirement Filed.
U.S. Appl. No. 14/300,106, dated Dec. 22, 2015 Issue Fee Payment.
U.S. Appl. No. 14/300,106, dated Sep. 24, 2015 Notice of Allowance.
Alam et al., "An Adaptive Strain Estimator for Elastography," IEEE Transactions on Ultrasonics, Ferroelectrics, and Frequency Control, vol. 45, No. 2, Mar. 1998, pp. 461-472.
Amin et al., "Therapy planning and monitoring of tissue ablation by high intensity focused ultrasound (HIFU) using imaging and simulation", Conf Proc IEEE Eng Med Biol Soc. 2008, 4471.
International Search Report and Written Opinion dated Jul. 17, 2012 in International Application No. PCT/US12/35685.
International Search Report and Written Opinion dated Oct. 18, 2012 in International Application No. PCT/US12/35685.
Liu et al., "Opening of the Blood-Brain Barrier by Low-Frequency (28-kHz) Ultrasound: A Novel Pinhole-Assisted Mechanical Scanning Device", Ultrasound in Med & Biol., vol. 36, Issue 2, Feb. 2010, pp. 325-335.
Long et al., "An integrated system for therapy planning of high intensity focused ultrasound", Electro/Information Technology, 2008. EIT 2008. IEEE International Conference on May 18-20, 2008, pp. 461-464.
Spalazzi et al., "Elastographic Imaging of Strain Distribution within the Anterior Cruciate Ligament and at the AGL-Bone Insertions," IEEE Ultrasonics Symposium, Sep. 2005, pp. 1755-1758.
Vaezy et al., "Real-time visualization of high-intensity focused ultrasound treatment using ultrasound imaging", Ultrasound Med Biol., Jan. 2001, 27(1), pp. 33-42.
Zheng et al., "A Targeting Method Based on Acoustic Backscatter for Treatment Planning In Tissue Ablation Using Focused Ultrasound", IEEE Trans on Biomed Eng. vol. 57, No. 1, Jan. 2010, pp. 71-79.
Ziadloo et al., "Real-time 3D image-guided HIFU therapy", Conf Proc IEEE Eng Med Biol Soc. 2008, 4459-62 .
Hynynen et al., "Local and reversible blood-brain barrier disruption by noninvasive focused ultrasound at frequencies suitable for transskull sonications" *NeuroImage* 24 (2005) 12-20.

\* cited by examiner

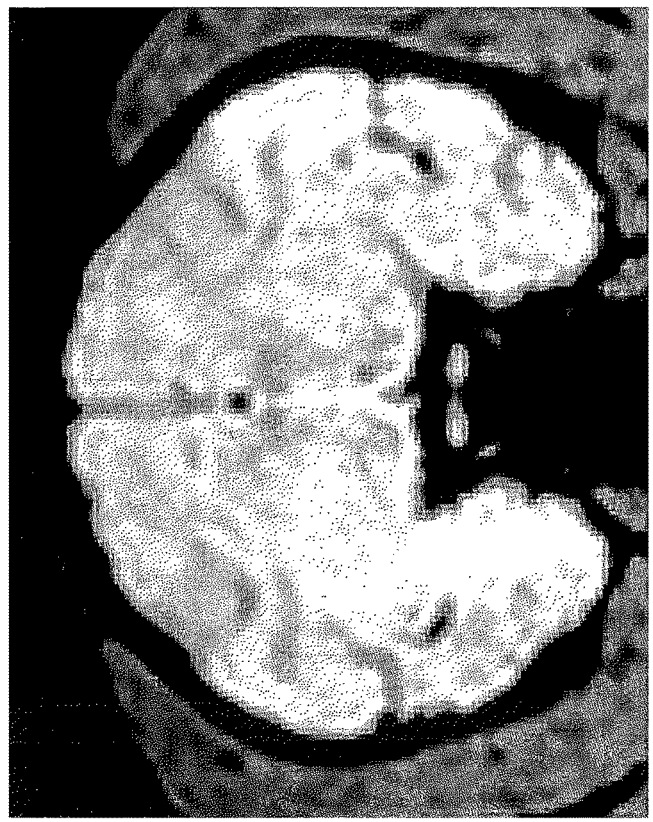
FIG. 9

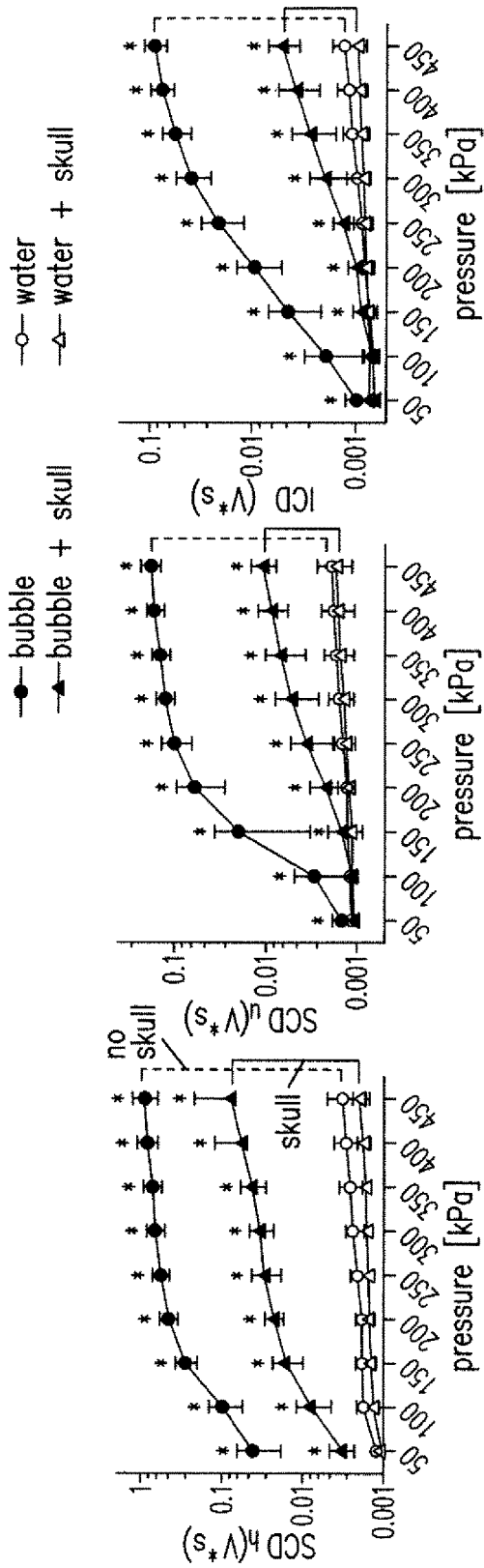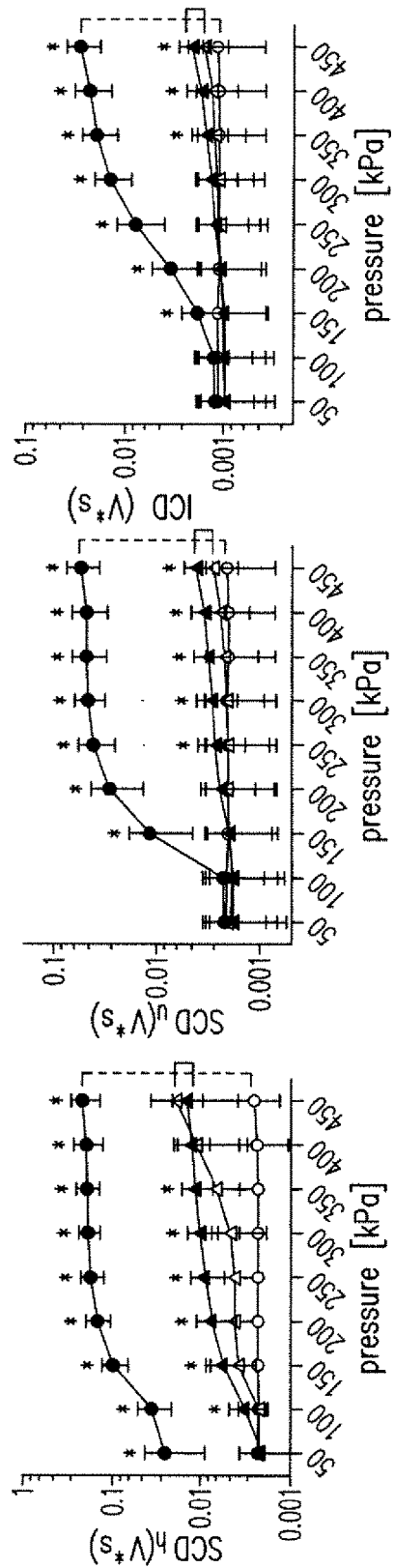

(a) (b) (c) (d)

SYSTEMS AND METHODS FOR REAL-TIME, TRANSCRANIAL MONITORING OF BLOOD-BRAIN BARRIER OPENING

CROSS-REFERENCE TO RELATED APPLICATIONS

This application claims the benefit of U.S. Provisional Patent Application No. 61/873,310, filed Sep. 3, 2013, which is incorporated by reference herein in its entirety.

STATEMENT REGARDING FEDERALLY-SPONSORED RESEARCH

This invention was made with government support from the National Institutes of Health under Grant Nos. R01AG038961 and R01EB009041. The government has certain rights in the invention.

BACKGROUND

In certain techniques for targeted blood-brain barrier opening, including using focused ultrasound (FUS), it can be desirable to increase targeting accuracy while decreasing the time and effort necessary for accurate targeting. Systems and techniques for blood-brain barrier opening using FUS are described in U.S. Patent Application Publication No. 2009/0005711, which is incorporated by reference herein in its entirety.

Targeting accuracy can be reduced by aberrations of the ultrasound beam caused by the skull. The discrepancy between the high speed of sound through the skull and the low speed through the underlying brain tissue, alone or along with attenuation of ultrasound waves through the skull bone, can distort the beam shape, including at higher frequencies. Moreover, the trabecular layer of the skull can induce heterogeneities in both speed of sound and density, which can lead to phase aberrations of the acoustic beam. At higher frequencies, the defocusing effect of the skull can be increased as the wavelength can reach the size of local skull bone heterogeneities (for example, the trabeculae can be around 1 mm). The phase aberrations can be reduced by reducing the ultrasound frequency. However, the size of the focal region can likewise increase, which can increase the likelihood of undesirable inertial cavitation.

In therapeutic ultrasound, it can also be desirable to have real-time monitoring and treatment efficiency verification. A passive cavitation detector ("PCD") can be used to transcranially acquire the acoustic emissions stemming from the microbubble. The frequency analysis of backscattered signals can be relevant to characterize undesirable bubble-capillary interaction.

SUMMARY

Systems and techniques for transcranial monitoring of safe blood-brain barrier opening in real time are disclosed herein.

In one embodiment of the disclosed subject matter, an example system for real-time, transcranial monitoring of safe blood-brain barrier opening can include an ultrasound transducer and an ultrasound transducer; and a targeting component, coupled to the ultrasound transducer and configured to determine an approach angle for targeted blood-brain barrier opening proximate a predetermined region in a brain of a patient, and position the ultrasound transducer to generate a focused ultrasound signal at the determined approach angle to the predetermined region in the brain.

In some embodiments, for example and without limitation, the system can include the ultrasound transducer can operate at an intermediate frequency of 500 kHz. The ultrasound transducer can be configured to operate without use of a magnetic resonance image monitoring and can include a stereotactic manipulator for performing targeting of the predetermined region in the brain.

In some embodiments, the system can also include a real-time monitoring component for monitoring opening of the brain-blood barrier by the ultrasound transducer. The monitoring component can perform monitoring using a frequency of a backscattered acoustic signal generated in response to the targeting by the ultrasound transducer. The real-time monitoring component can include passive cavitation detector.

In some embodiments, computer program products are provided that comprise non-transitory computer readable media storing instructions, which when executed by at least one data processor of one or more computing systems, cause at least one data processor to perform operations disclosed herein. Similarly, computer systems are also described that can include, for example, one or more data processors and a memory coupled to the one or more data processors. The memory can temporarily or permanently store instructions that cause at least one processor to perform one or more of the operations disclosed herein. In addition, methods can be implemented by one or more data processors either within a single computing system or distributed among two or more computing systems.

Certain variations of the subject matter disclosed herein are set forth in the accompanying drawings and further description below. Other features and advantages of the subject matter described herein will be apparent from the description and drawings, and from the claims.

BRIEF DESCRIPTION OF THE DRAWINGS

FIG. 9 is two exemplary magnetic resonance ("MR") images illustrating T2-weighted (left) and SWI (right) MR images corresponding to the technique of FIG. 2.

FIGS. 15A-15I are diagrams illustrating additional characteristics according to the disclosed subject matter of (a) $SCD_h$, (b) $SCD_u$, and (c) ICD for the macaque skull examples using 100-cycle pulses. (d) $SCD_h$, (e) $SCD_u$, and (I) ICD for the human skull examples using 100-cycle pulses. (g) $SCD_h$, (h) $SCD_u$, and (i) ICD without the skull in place using 100- and 5000-cycle pulses. The error bar shows the standard deviation. *: p<0.05. Green *: comparison made in the cases without the skull in place. Red *: comparison made in the cases with the skull in place.

DETAILED DESCRIPTION

According to aspects of the disclosed subject matter, systems and techniques for real-time, transcranial monitoring of safe blood-brain barrier opening include an ultrasound transducer and a targeting component configured to target the ultrasound transducer for targeted blood-brain barrier opening by targeting a predetermined region in a brain of a patient from a predetermined approach angle.

Figure 1:
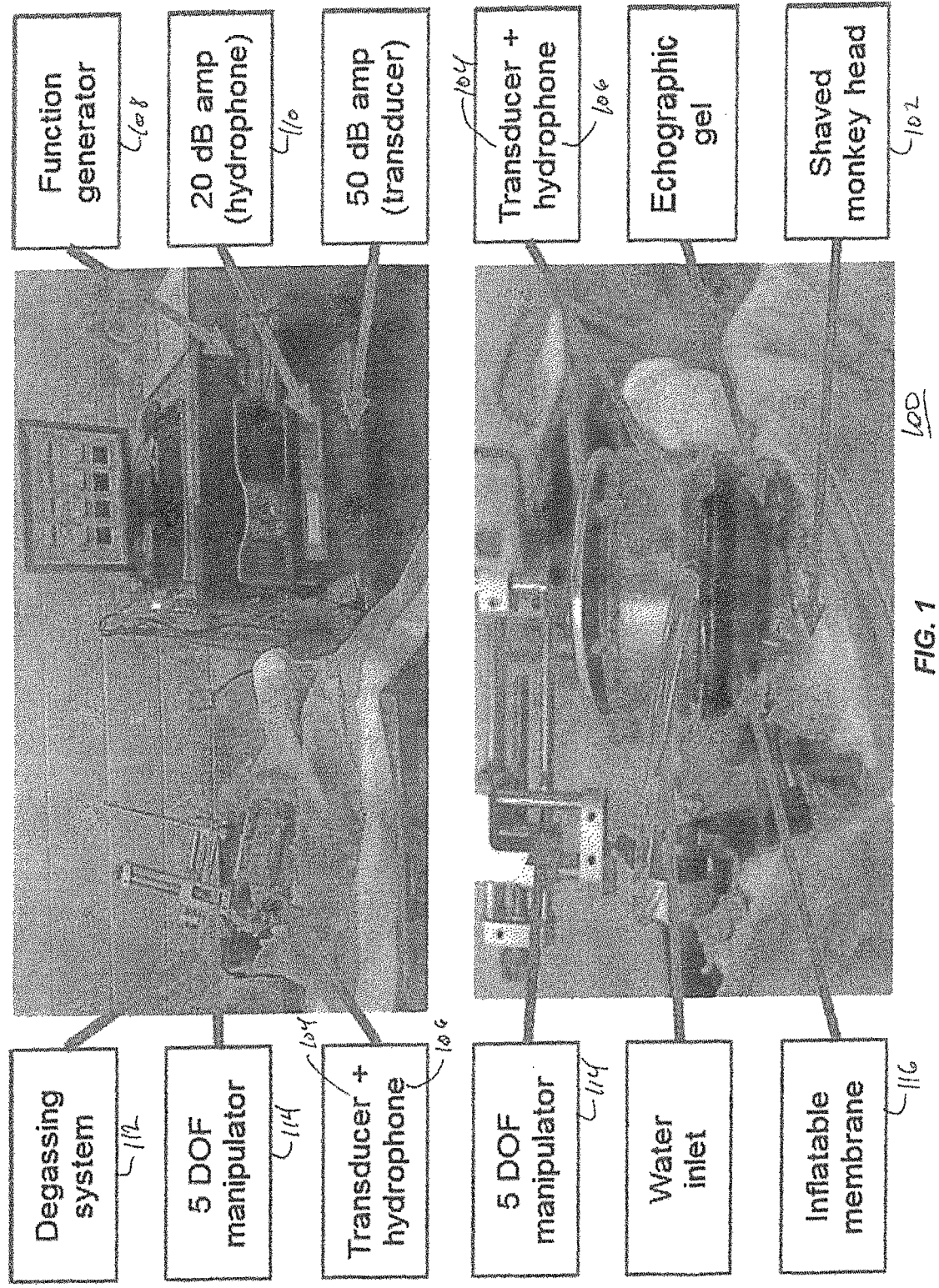
FIG. 1 illustrates an exemplary system for real-time, transcranial monitoring of safe blood-brain barrier opening, according to the disclosed subject matter.
Figure 2:
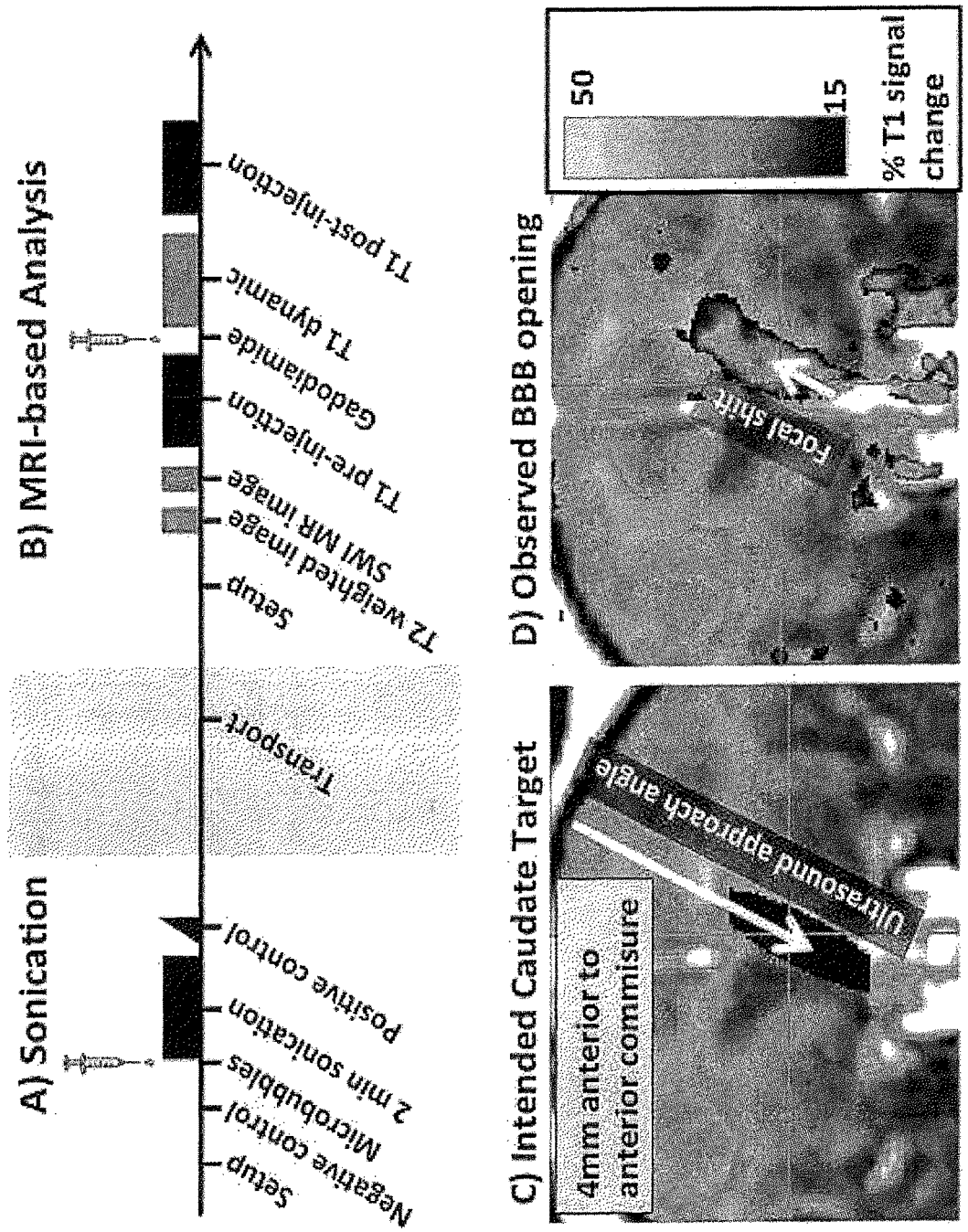
FIGS. 2A and 2B are diagrams illustrating an exemplary technique for sonication with subsequent MRI-based verification according to the disclosed subject matter.
FIGS. 2C and 2D are cranial ultrasound scans for purpose of illustration and confirmation of the disclosed subject matter.

With reference to FIG. 1, an exemplary system 100 for real-time, transcranial monitoring of safe blood-brain barrier opening is illustrated. A subject 102 can be positioned in a stereotaxic frame under general anesthesia. For example and not limitation, a 500-kHz ultrasound transducer 104 can be attached to a Kopf stereotaxic manipulator 114 to enable targeting of the ultrasound focus in stereotactic coordinates, as described herein. Negative control sonications can be performed in the absence of microbubbles, as illustrated in FIG. 2 and discussed further herein. For example and not limitation, monodisperse 4-5 11 m microbubbles can be IV injected and size-isolated using differential centrifugation. The subject 102 can be sonicated for about 2 minutes with focal maximum pressures ranging between about 0.20 and about 0.30 MPa. Post-sonication controls in the presence of microbubbles can be performed, and the location of the BBB opening can be determined, for example using contrast-enhanced T1images, as discussed herein.

With continued reference to FIG. 1, the attenuation in the subject 102 scalp can be considered around −0.9 dB/em and the thickness can be about 0.5 em. Attenuation in the subject 102 brain tissue can be determined to be about −0.5 dB/em and the thickness can be about to 2 em. As such, the emission amplitude can be raised by 7.15 dB (approximately a factor 2.28) compared to the calibration measurements in water to compensate for the energy loss along the path. For example and without limitation, a Hatband, spherically focused hydrophone 106 (Y-107, Sonic Concepts, WA, USA) can be positioned through the center hole of the FUS transducer 102. The two transducers 104, 106 can be aligned so that their focal regions overlapped within the confocal volume. The hydrophone 106, which can be connected for example and without limitation to a digitizer 108 (Gage Applied Technologies, Inc., Lachine, QC, Canada) through a 20-dB amplification 110 (5800, Olympus NDT, Waltham, Mass., USA), can monitor real-time acoustic emissions from microbubbles (referred to herein as passive cavitation detection or PCD).

Still referring to FIG. 1, the top image illustrates a large view of the operating room. As embodied herein, the PC and amplifiers can be used to drive the transducer-hydrophone assembly. The degassing system 112 (vacuum pump+water circulation pump) can provide a constant flow of degassed water for acoustic coupling. As embodied herein, the transducer-hydrophone assembly can be mounted on a manipulator with 5 degrees of freedom (x, y, and z position of the focus, as well as two approach angles: azimuth and elevation). The bottom image illustrates an enlarged view. The membrane 116 can be inflated to regulate the water flow using the degassing system 112, which can provide a maximal acoustic transmission in the subject 102.

Individualized targeting of the ultrasound focus to a particular brain region can be performed. The targeting can include T1 weighted stereotactically aligned structural images acquired for all animals (Tt sequence as discussed further herein). For targeting in stereotactic coordinate frames, an R-based (R Development Core Team 2009) software package (stereotax.R) can be utilized to convert a particular setting of the stereotactic manipulator (Kopf) into stereotactic coordinates. The setting of the stereotactic manipulator can be determined by one or more of the following free parameters: the setting of the media-lateral drive (ml), the position of the manipulator on the stereotactic arm along the anterior-posterior direction (ap), the setting of the dorso-ventral drive (dv), the rotation of the manipulator around the z-axis (azimuth), the tilt of the manipulator (elevation angle) that can occur either around the ml- or ap-axis (elevation setting), the position of the manipulator on the left or right stereotactic arm (arm), the relative alignment of the ml and dv stereotax drives, i.e., the ml drive positioned anterior or posterior to the dv drive (stereo), and a degree of freedom that determined the attachment of the ultrasound transducer on the stereotactic manipulator (finger). Based at least in part on the setting of the stereotactic manipulator, the software can determine the focal point and the axis from the focal point to the ultrasound transducer (angle of approach). For visualization purposes, the predicted region of BBB opening around the ultrasound focus can then be projected onto an individual stereotactically aligned T1 image, as illustrated for example in FIG. 2. The software can also invert this procedure, that is, for any desired sonication target (including a desired approach angle) that can be specified in stereotactic coordinates, the software can determine up to eight different settings of the stereotactic manipulator to target this neural structure from the specified approach angle, and an optimal approach angle can then be determined. As embodied herein, the approach angle can be set to provide a close to perpendicular incidence angle between ultrasound beam and skull.

The BBB opening can be verified, for example and as embodied herein, with contrast-enhanced MRI. T2 and T2 FLAIR images can be taken of the subject 102 to detect any potential damage caused by the sonication. The integrity of the BBB can be tested using a T1 contrast agent gadodiamide (Omniscan™) that can be used to visualize the break-down of the BBB in neurological disease. A high-resolution structural T1 image can be recorded prior to the injection of gadodimide (T1 Pre; 3D Spoiled Gradient-Echo, TRITE=20/1.4 ms; flip angle: 30°; NEX=2; in-plane resolution: 1×1 mm2; slice thickness: 1 mm with no interslice gap). 30 min after injection of 0.15 ml/kg gadodiamide IV, another T1 image can be acquired using similar scanning parameters (T1 Post). As gadodiamide typically not cross the intact BBB, increased T1 signal strength can be found in vessels or regions with increased BBB permeability. As embodied herein, a 3D T2-weighted sequence (TRITE=3000/80 ms; flip angle: 90°; NEX=3; spatial resolution: 400×400 mm2; slice thickness: 2 mm with no interslice gap) and a 3D Susceptibility-Weighted Image (SW) sequence can be applied (TRITE=19/27 ms; flip angle: 15°; NEX=1; spatial resolution: 400×400 mm2; slice thickness: 1 mm with no interslice gap).

T1 pre and T1 post images can be registered to the individual stereotactically aligned T1 image using FSL's FLIRT routine. To estimate gadodiamide concentration [Gd]c, the post T1 image can be divided by the pre T1 image to obtain a post/pre image. The post/pre image can highlight regions of increased T1 contrast following the injection of gadodiamide. This can include regions of interest where the BBB was opened, but also can include vessels or other regions with high blood volume such as the pial surface. The post/pre image can be flipped such that the left hemisphere overlaid the right hemisphere. The un-flipped image can be divided by the flipped image. This procedure can reduce or remove activations due to high [Gd]c in voxels with high blood-volume, in symmetric regions between the hemispheres. The resulting image can highlight increased [Gd]c in the sonicated region, as well as some residual artificial activation, which can be due to asymmetric vasculature.

Figure 3:
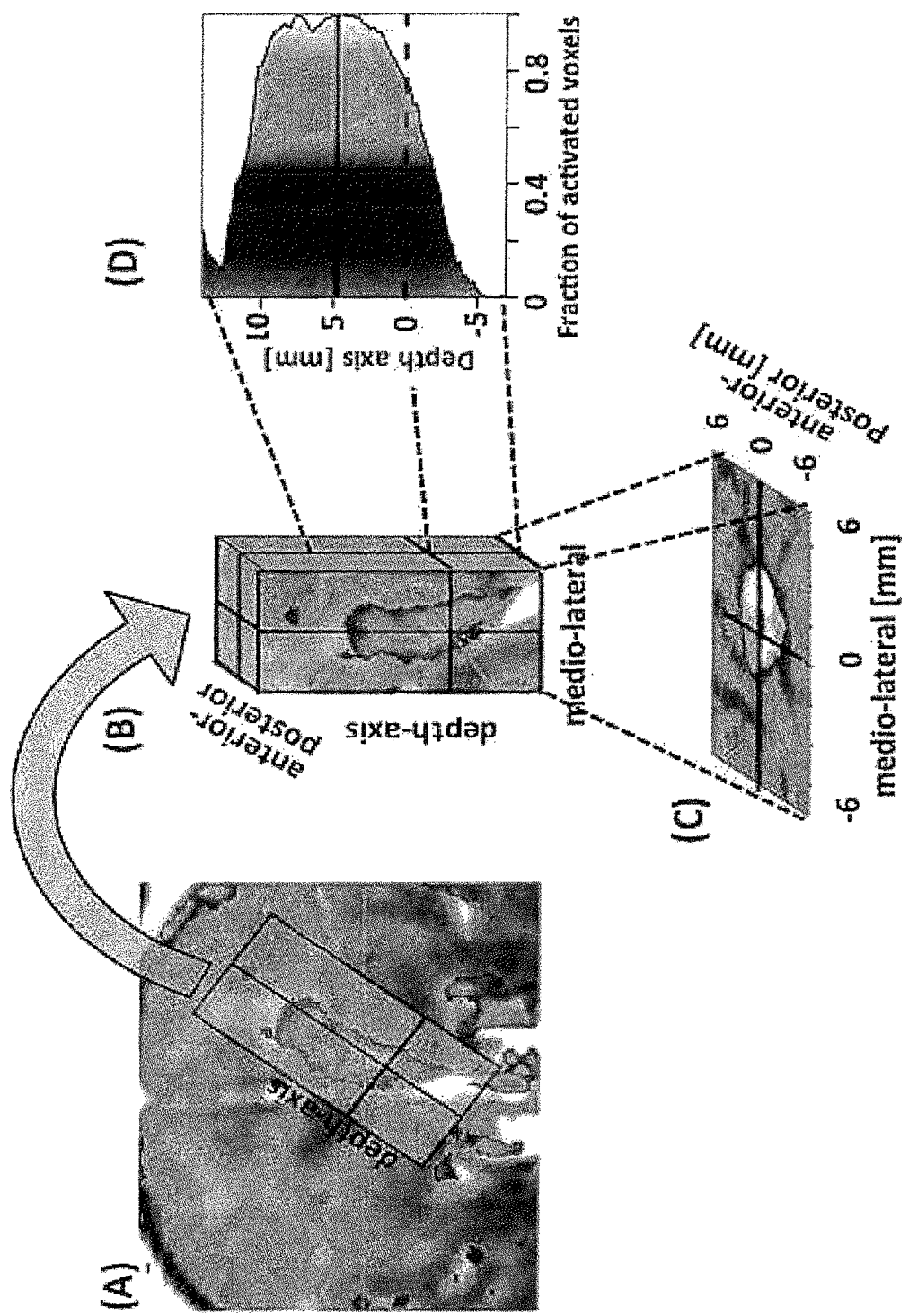
FIGS. 3A-3D together illustrate a quantification of targeting accuracy according to the disclosed subject matter.

To assess the targeting accuracy, the resulting image can be rotated and shifted into a new coordinate frame, where the origin can be defined as the predicted location of the ultrasound focus, and the z-axis can correspond to the approach angle, as shown for example in FIG. 3. FIGS. 3A-3D form a series of illustrations showing a quantification of targeting accuracy. After calculating the raw result image that provides a normalized estimate of the increase in T1 contrast (as shown in FIG. 3A), the image was shifted and rotated in to a new coordinate frame (as shown in FIG. 3B) whose origin was defined by the coordinates of the intended target, and the z-axis corresponded to the approach angle. A voxel was considered opened if its T1 value was enhanced by about 10%. The in-plane targeting accuracy was assessed by averaging the fraction of opened voxels across the z-axis (as shown in FIG. 3C). Targeting in the depth axis along the ultrasound beam was quantified by collapsing across the x and y-axis (as shown in FIG. 3D).

A region of interest around the origin was selected corresponding to ±7.5 mm in the x- and y-direction, and −5 to +12 mm along the z-axis. A voxel can be considered "opened" when the T1-enhancement exceeds a threshold of 10%. The total volume of the BBB opening can be quantified as the volume of the opened voxels in the region of interest around the sonication target. The fraction of opened voxels can be averaged across the z-axis. The region of the opening can be defined on the two-dimensional x-y map as pixels with more than an average of 35% of opened voxels (black contour line). The observed center of the sonication in the x-y-plane can be defined as the center of mass of the region of the opening (illustrated as a black dot in FIGS. 4-6). The targeting error in the x-y plane can be defined as the difference of the observed position of the opening from the theoretical position of the geometric focus. Similarly, targeting accuracy along the axis of propagation of the ultrasound can be assessed by averaging the fraction of opened voxels across the x- and y-axis. The averaging can be performed on voxels within a square region of ±2 mm around the observed xy-center of the sonication. The center of the sonication along the z-axis can be defined as the center of gravity of the bins with more than 35% opened voxels. The targeting error along the z-axis can be defined as the difference between the observed center of the sonication along the z-axis and the predicted focal depth. The predicted focal depth can be determined to be the geometric focal depth plus 5 mm due to the focal shift induced by the skull.

Figure 4:
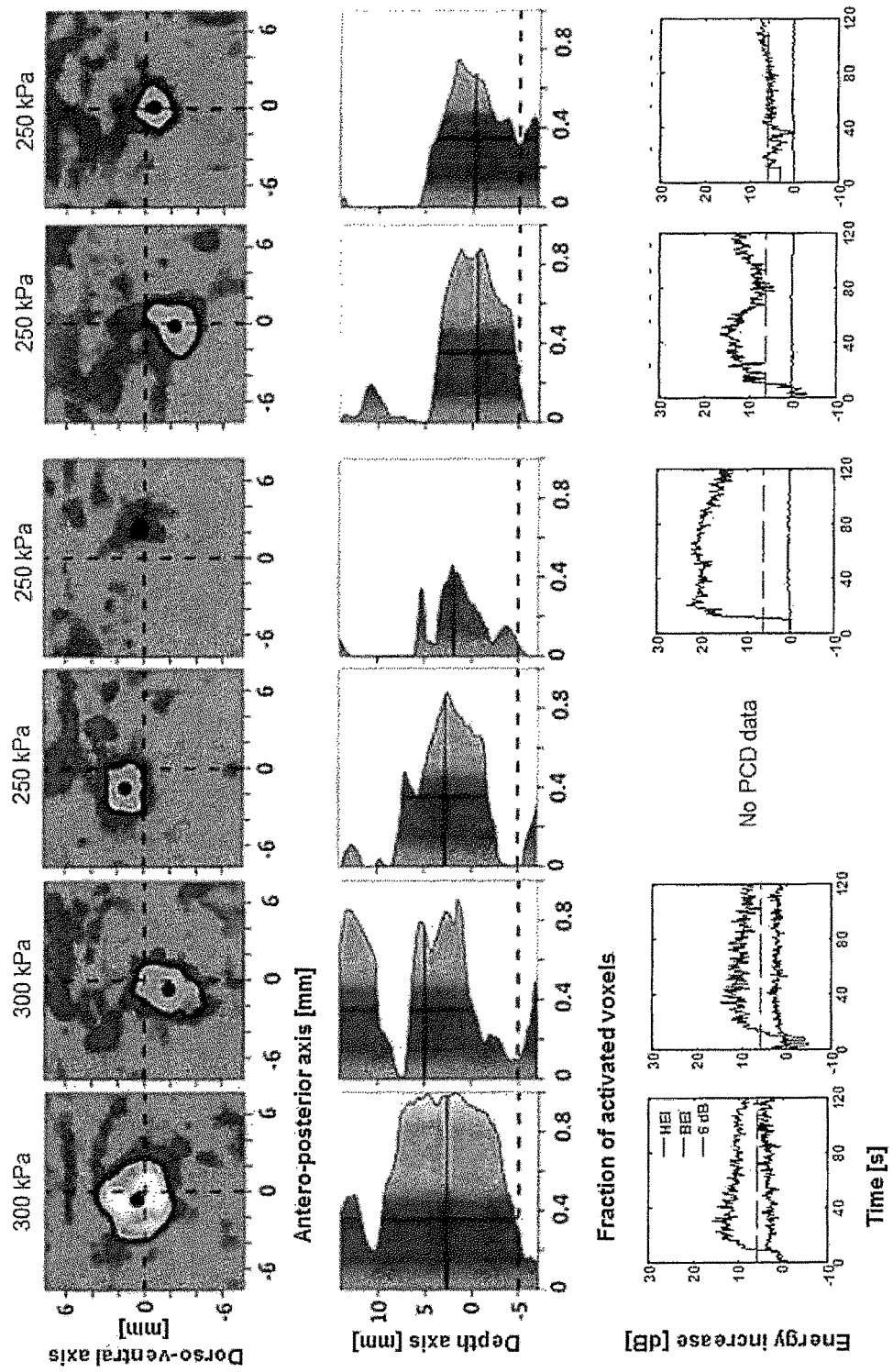
FIG. 4 is a series of diagrams illustrating targeting accuracy according to the disclosed subject matter.

FIG. 4 forms a series of plots illustrating targeting accuracy for 6 (4+2 for two monkeys 0 and N) sonications of caudate nucleus. The panels in the first row show the color-coded fraction of activated voxels (>10% enhancement of T1 signal) as a function of medio-lateral and anteroposterior deviation from the intended focal point in the x-y-plane. The panels collapsed across voxels that are between −5 mm and 10 mm in depth from the intended depth. In all instances, the opening of the BBB either overlapped with or was in immediate vicinity of the intended target. To quantify targeting accuracy along the direction of the ultrasound propagation, panels in the second row show the fraction of activated voxels collapsed around a 2 mm by 2 mm square region around the measured focal point (block dots in panels in A). The dotted horizontal line corresponds to the depth of the geometric ultrasound focus. The actual focal depth (solid horizontal line) shifted about 5 mm towards the ultrasound transducer. Panels in the third row depict the backscattered acoustic energy of the microbubbles excited in the ultrasound focus as a function of time from injection of the microbubbles. The blue line to the desired harmonic oscillations of the microbubbles (HEY) associated with safe BBB opening. The black line corresponds to inertial cavitation (BEI) that has been linked to extravasation of red blood cells and tissue damage. The red line corresponds to the BEI detection threshold.

Figure 5:
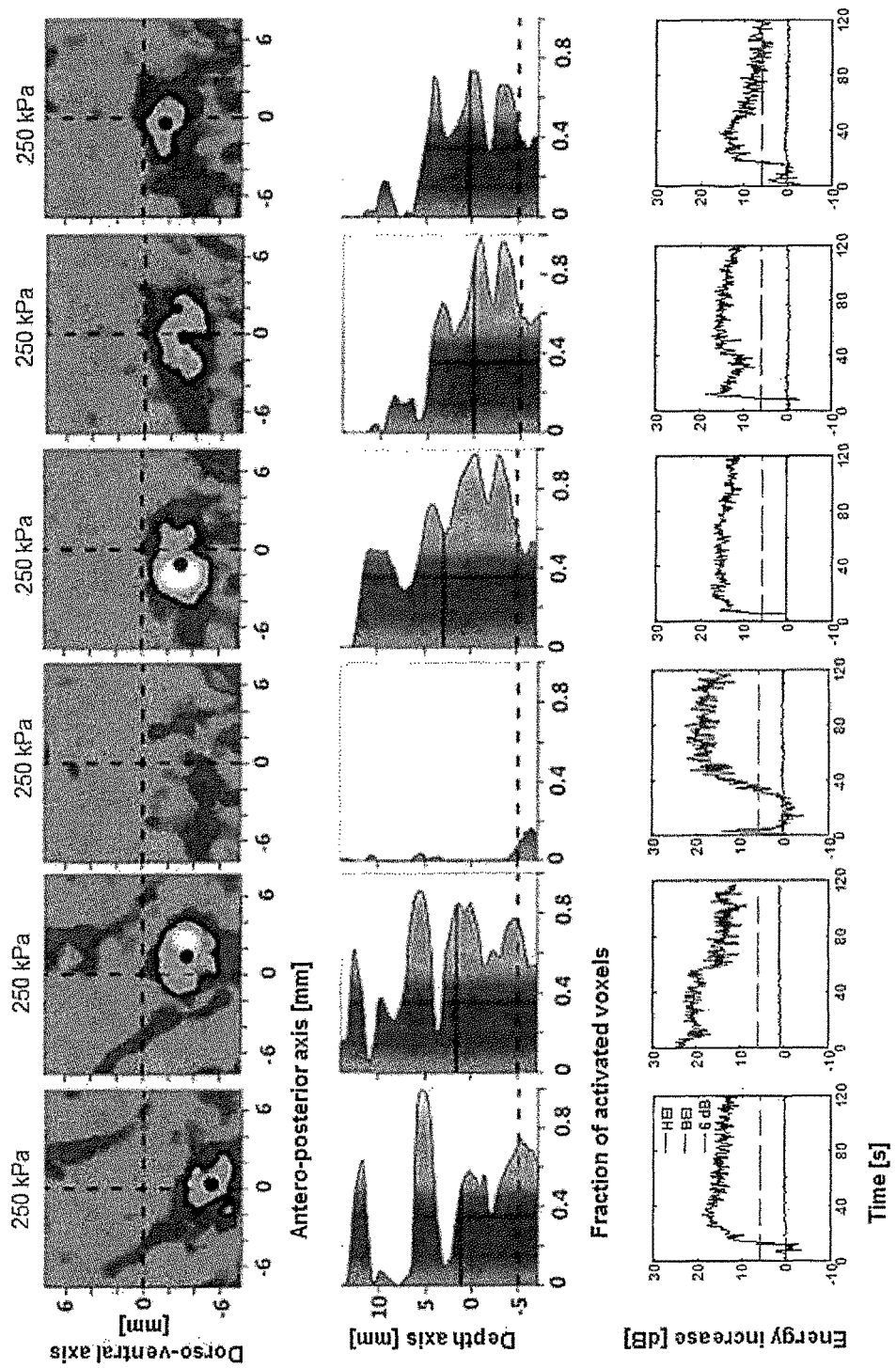
FIG. 5 is a series of diagrams illustrating targeting accuracy according to the disclosed subject matter.

FIG. 5 forms a series of plots illustrating targeting accuracy and PCD responses for 6 sonications of putamen in animal one. The PCD for sonication 12 06 23 shows immediately elevated HEI values because by accident, the microbubbles were injection before sonication onset.

Figure 6:
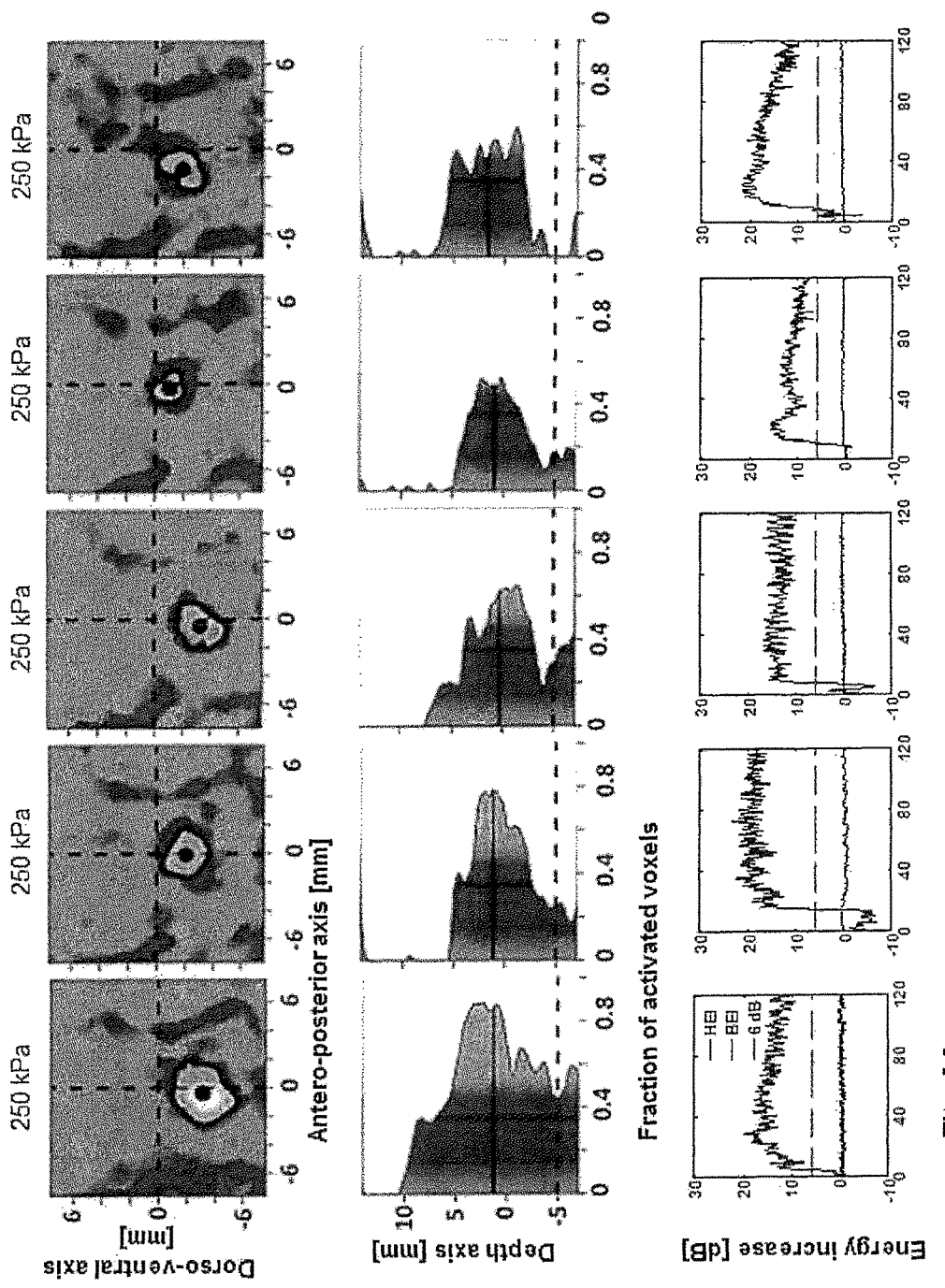
FIG. 6 is a series of diagrams illustrating targeting accuracy according to the disclosed subject matter.

FIG. 6 forms a series of plots illustration targeting accuracy and PCD responses for 5 sonications of putamen in the second animal.

As embodied herein, real-time monitoring can be performed using the evolution of the frequency content of the backscattered acoustic signal. Bubble oscillations along the acoustic excitation can be non-linear (stable cavitation), and the PCD can thus detect harmonic modes in the frequency spectrum. Bubble collapse and jet, more generally described herein as inertial cavitation, can induce broadband noise. As such, detection of broadband response can be considered a signature of inertial cavitation. Using 4-5-f, 1 m monodisperse microbubbles, the BBB can be opened without inertial cavitation. Additionally, stable cavitation alone has not been associated with any tissue damage. The frequency spectra of backscattered acoustic emissions can be used to infer the cavitation-behavior of the micro-bubbles in the focal region. To remove the harmonic (nf, n=1, 2, ..., 6), sub-harmonic (f/2) and ultra-harmonic (nf/2, n=3, 5, 7, 9) frequencies produced by stable cavitation, the response within a 300-kHz bandwidth around each harmonic and 100-kHz bandwidth of each sub- and ultra-harmonic frequency can be filtered out in order to obtain the broadband signal. This can be performed within the 0.6-5.2 MHz frequency band to reduce or inhibit perturbation induced by the fundamental frequency and to account for the growing attenuation of the signal along the frequency. From the sets of two spectra, both the broadband and total energies (respectively $\epsilon^{broadband}$ and $\epsilon^{total}$) can be determined by summing the spectral amplitudes (s) on the defined frequency range as follows:

$$\epsilon \propto \int_{f=0.6MHz}^{5.2MHz} s^{-2}(f)df \quad (1)$$

Two metrics can be represented as indications of inertial or stable cavitation by analyzing the differences between backscattered with and without bubbles. The broadband energy increase ("BEJ") from the negative control level (without microbubbles) can be monitored as an indication of inertial cavitation and can be represented as follows:

$$BEI = 10\log\left(\frac{\epsilon_{bubble}^{broadband}}{\epsilon_{control}^{broadband}}\right) \quad (2)$$

The harmonic energy can be obtained by subtracting the broadband energy to the total energy. The harmonic energy increase ("HEI") can be an indication of stable cavitation and can be represented as follows:

$$HEI = 10\log\left(\frac{\epsilon_{bubble}^{total} - \epsilon_{bubble}^{broadband}}{\epsilon_{control}^{total} - \epsilon_{control}^{broadband}}\right) \quad (3)$$

The energy increase of the control signals can be represented as the average value of the 2 second long negative control sonication taken before injecting the bubbles but otherwise used the same ultrasound parameters as the treatment sonication.

For purpose of illustration and not limitation, as embodied herein, immediately after the treatment sonication, a series of 2-sec positive control sonications can be performed while microbubbles are still in circulation. The positive controls can use pressures between 0.05 and 0.35 MPa. Except for the shorter duration and variable pressures, the same sonication settings can be applied for the treatment sonication. The positive controls can be used to describe the relationship between ultrasound pressure and the harmonic/broadband energy increase. As discussed further herein, for purpose of illustration and confirmation of the disclosed subject matter, 8 testing sets were performed. The mean HEI over the entire sonication can be calculated to relate stable cavitation to the observed size of the BBB opening.

EXAMPLE 1

For purpose of illustration and confirmation of the disclosed subject matter, exemplary experimental results were obtained according to the techniques disclosed herein. The experimental results included, for example, results of a series of 17 sonications targeting the caudate nucleus (6) and the putamen (11) in the left hemispheres of two macaque monkeys. The analyses are focused on targeting accuracy, the relationship between PCD response and BBB opening volume as well as safety of the procedure. In addition, one exploratory study examined the duration for which the BBB remains open after the sonication.

FIGS. 2A-2B together illustrate timelines of sonication experiment with subsequent MRI-based verification. Briefly, the animals were sonicated for two minutes using a 500 kHz focused ultrasound transducer following the systemic injection of microbubbles. The opening location was then analyzed using contrast-enhanced T1 images (as shown in FIG. 2D) for details. Additional clinical scans were performed to detect potential damage. FIG. 2C illustrates a geometric ultrasound focus overlaid on a T1 structural scan in stereotaxic coordinate frame. Due to the geometry of the ultrasound transducer, the focal region was elongated along the axis of ultrasound propagation. The ultrasound was applied at an angle of 26° from the upper right to provide a close to normal incidence angle of the ultrasound and skull. FIG. 2D illustrates a T1 structural scan in stereotaxic coordinate grame and illustrates increased blood-brain barrier (BBB) permeability for the T1 contrast agent gadodiamide following a single sonication of left caudate. Brighter colors indicate regions where gadodiamide was able to diffuse across the BBB into the brain tissue. The remaining regions of increased T1 signal indicate asymmetric vasculature. Note the close alignment between intended (as shown in FIG. 2 C) and actual location (as shown in FIG. 2D)) of the BBB opening. The axial shift in location of the BBB opening towards the transducer is close to the value predicted from in-vitro experiments.

FIGS. 2C-2D illustrates an exemplary result of BBB disruption using T1-weighted MR imaging and gadodiamide MR contrast agent. The image on the left depicts the theoretical position of the ultrasound focus. The image on the right renders regions where the T1 contrast agent gadodiamide was able to diffuse to the brain parenchyma as a result of BBB opening (as described herein). FIGS. 2C-2D thus highlight the good qualitative agreement between the intended target of the ultrasound focus and the actual region of increased BBB permeability.

To quantify the targeting accuracy of the method, the processing shown in FIG. 3 was performed for each experiment (as described herein). The individual plots for lateral and axial targeting accuracy are depicted in FIG. 4 for caudate targets of both animals. FIGS. 5 and 6 provide identical plots for the putamen sonications in the two animals, respectively. These results illustrate the reproducibility and targeting precision of the FUS technique. First, the targeting accuracy was quantified by averaging the relative focal position for all sonications and animals. The mean focal point was 0.2±1.0 mm posterior to the intended target (all results are reported as mean±standard deviation in mm). This difference did not reach significance (t-test, p>0.05). The observed focal point was significantly ventral to the intended target (1.9±1.7 mm; t-test p<0.05). Further, the mean focal point was shifted towards the ultrasound transducer (1.4±1.4 mm, t-test, p<0.05). Predicted focal depth was defined as the depth of the geometric ultrasound focus plus 5 mm (i.e., shifted towards the ultrasound transducer). The 5 mm shift was added to account for the shift of focal depth that was measured in vitro with immersed skull plates. Hence, the results demonstrate the correspondence between the in vitro and in vivo measurements. However, a stronger focal shift was observed in the in vivo experiments.

The reliability of the sonication procedure was assessed as the mean targeting error (absolute distance from intended target). The mean targeting error over all sonications in the lateral plane was 2.5±1.2 mm. Mean targeting error in the axial direction was 1.5±1.3 mm. Combined lateral and axial error averaged 3.1±1.3 mm.

During experiments, and according to some embodiments, the system was further configured to dissociate random errors due to day-to-day fluctuations from systematic targeting errors that could be specific to a particular animal and/or target. To quantify the systematic targeting error the location of the focal point for both targets and both animals were averaged separately. The mean systematic lateral targeting error was 1.8 mm. Mean systematic axial targeting error was 1.4 mm. Combining the lateral and axial error resulted in a mean systematic targeting error of 2.7 mm across all four targets (2 targets in 2 animals). An analysis of variance was utilized to test whether targeting accuracy differs as a function of the four different groups of sonications (two targets in two animals). Neither anterior-posterior nor axial position (relative to the intended target) differed as a function of the sonication group. However, dorso-ventral position depended on sonication group (ANOVA, p<O.OS). This can be due at least in part to the difference between the two caudate and the two putamen targets. In both animals, the sonications to putamen exhibited a systematic targeting error in the along the dorso-ventral axis. No such systematic targeting error was found in the caudate sonications.

Random error was further quantified, i.e., the absolute distance of the observed focus from the mean focal point over all repetitions with the same target in the same animal. The mean random lateral error was 1.2±0.6 mm. The mean random axial error was 0.6±0.6 mm. Combining lateral and axial error, a mean random error of 1.5±0.7 mm was found.

The size of the region in which the permeability of the BBB was increased was quantified. Averaged over all sonications, the volume of the BBB opening was estimated at 115±44 mm3. Larger openings were observed at higher sonication pressures (e.g., 0.30 MPa). Moderate openings were observed at lower pressures (0.20 or 0.25 MPa). One sonication at 0.25 MPa failed to elicit any opening (as shown in FIG. 5). Another sonication at 0.20 MPa only elicited a minimal opening (as shown in FIG. 4).

HEI and BEI monitoring were performed for each experiment in real time. The lower rows in FIGS. 5-7 render the recorded real-time monitoring for the corresponding sonications. In all but one of the sonications, HEI increased by at least 15 dB during the sonication. This was indicative of stable cavitation of the bubbles in the focal region. The lack of an increase in broadband energy indicated the absence of potentially harmful inertial cavitation. A 6 dB threshold, corresponding approximately to two times average of the negative controls, had been set as a limit of potential damage and was never surpassed.

Figure 7:
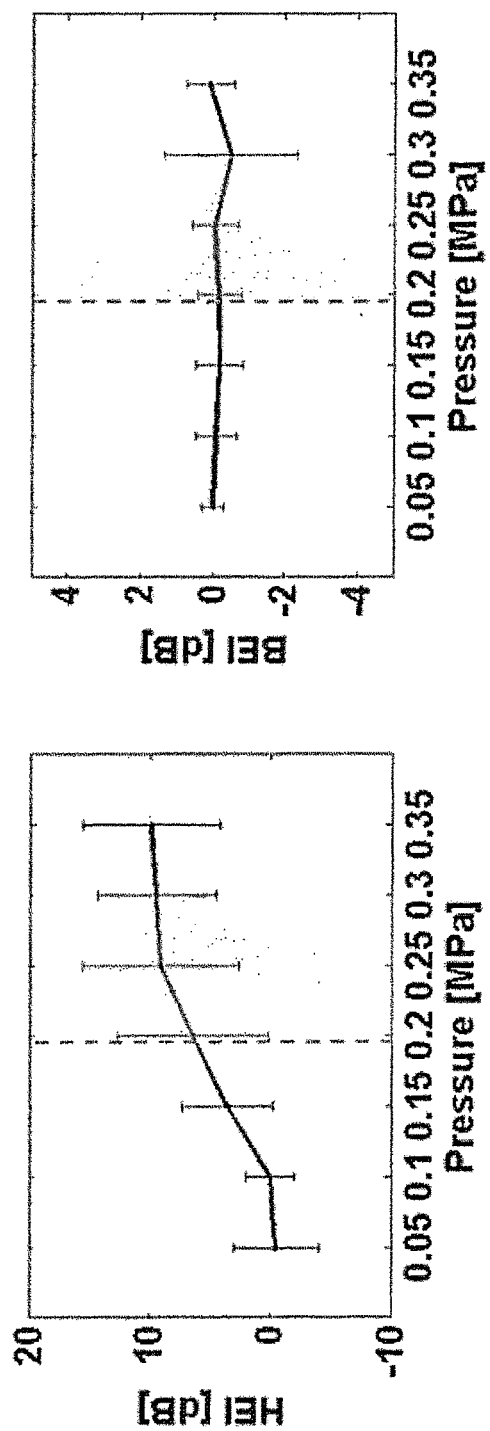
FIG. 7 is an exemplary series of diagrams illustrating harmonic ("HEI") and broadband ("BEI") energy increase according to the disclosed subject matter.

To characterize the dynamic range of the HEI and BEI responses, acoustic emissions as a function of ultrasound pressure were measured using a series of brief ultrasound pulses of a wide range of pressures (as described herein). FIG. 7 illustrates HEI and BEI as a function of ultrasound pressure. As expected, the HEI starts increasing for lower pressures (0.15 MPa). In contrast, the BEI remains unchanged at 0 dB for pressures up to 0.35 MPa. The HEI seems to reach an asymptote of approximately 10 dB for pressures at and above 0.25 MPa. It is lower than what is shown in the real-time PCD monitoring since this PCD testing was done after the treatment sonication and part of the circulating bubbles were degraded. This analysis defines a window between 0.15 and 0.35 MPa that leads to a reliable increase of harmonic energy while avoiding potentially harmful broad-band energy increase. In this study, pressures were well within this window and ranged between 0.20 and 0.30 MPa.

FIG. 7 forms a series of graphs illustration harmonic (HEI) and broadband (BEI) energy increase plotted as a function of ultrasound pressure. Data was acquired using a series of brief pulses of ultrasound after the main sonication while micro-bubbles were still circulating. The blue dash line corresponds to the lowest pressure at which BBB opening was achieved, and the. The light blue area highlights the pressure range used in this study. The red line corresponds to the ultrasound pressure that would cause BEI to rise above levels that were found to be safe in the current set of sonications.

Online PCD monitoring was tested to determine suitability to predict the success of the sonication and the size of the ensuing BBB opening. To that aim, size of the BBB opening as a function of the mean HEI during the 2-minute sonication period were plotted (e.g., FIG. 8B). The results showed that stronger HEI responses are not indicative of larger BBB opening volume. However, in all but two cases, the presence of HEI went along with a successful BBB opening.

Figure 8B:
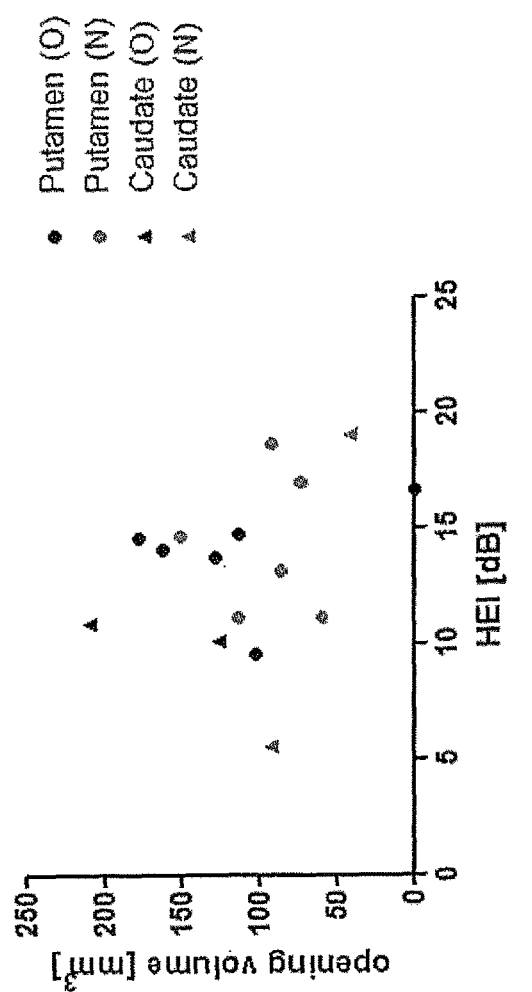
FIGS. 8A and 8B are exemplary diagrams illustrating BBB opening volume as a function of pressure and the average harmonic energy increase according to the disclosed subject matter.
Figure 8A:
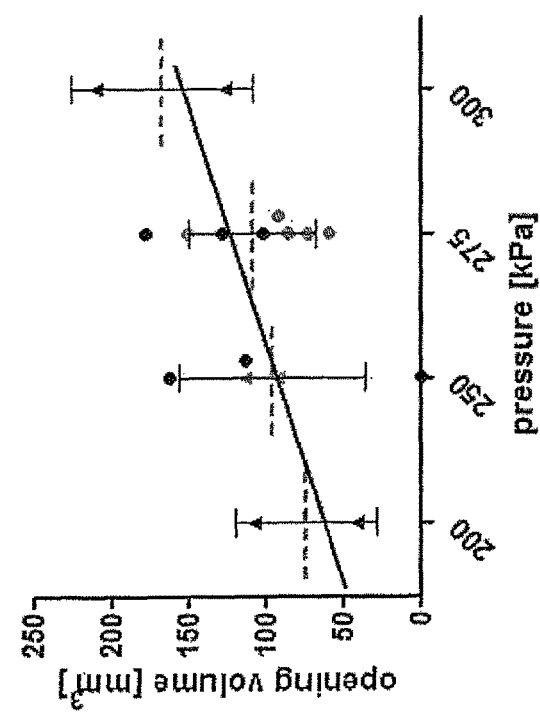

FIGS. 8A and 8B are graphs illustrating BBB opening volume as a function of pressure (as shown in FIG. 8A) and the average harmonic energy increase, HEI (as shown in FIG. 8B). Two targets in the putamen and the caudate for two animal subjects (0 and N) were marked separately. FIG. 8A illustrates the relationship between ultrasound pressure and opening size (r=0.41). Due to the narrow range of pressures and low number of sonications, this effect does not reach significance. The dashed line shows the mean value with standard deviation. As shown in FIG. 8B, there is no apparent relationship between average HEI and opening volume.

Additional MR imaging sequences (T2-weighted and SWI, as described herein) were used to assess potential brain damage after the ultrasound procedure. In line with the observed stable cavitation indicative of safe in situ ultrasound pressures, neither T2 nor SWI images detected any damage such as edema or hemorrhage in all experiments described herein. FIG. 9 illustrated coronal slices of T2-weighted and SWI images corresponding to the T1-weighted coronal slices rendered in FIG. 2.

FIG. 9 illustrates two MR images illustrating an example of T2-weighted (left) and SWI (right) MR images corresponding to the experiment from FIG. 2. Edemas appear brighter in T2-weighted images; hemorrhages, as well as large vessels appear in black in SWI images. No damage was detected on any of the experiments performed.

Figure 10:
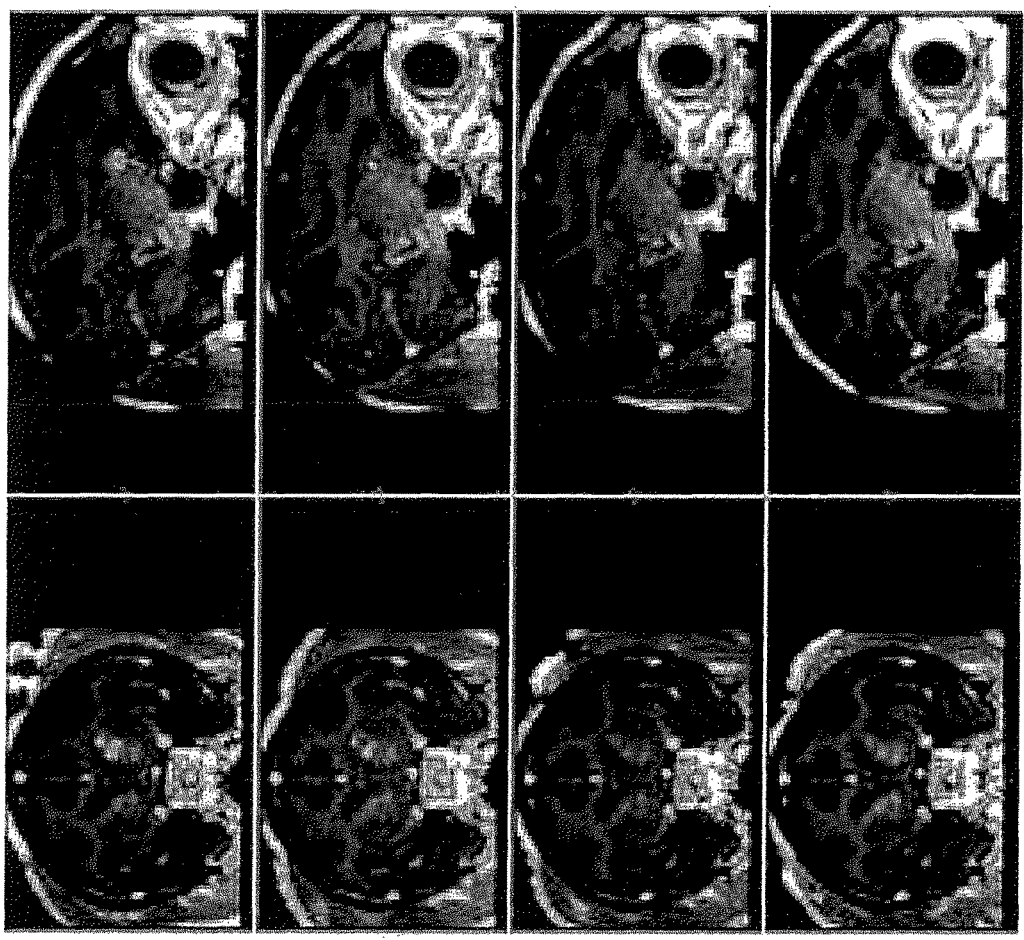
FIG. 10 is an exemplary series of coronal (left row) and sagittal (right row) T1-weighted MR slices illustrating BBB opening volume over time according to the disclosed subject matter.
Figure 11:
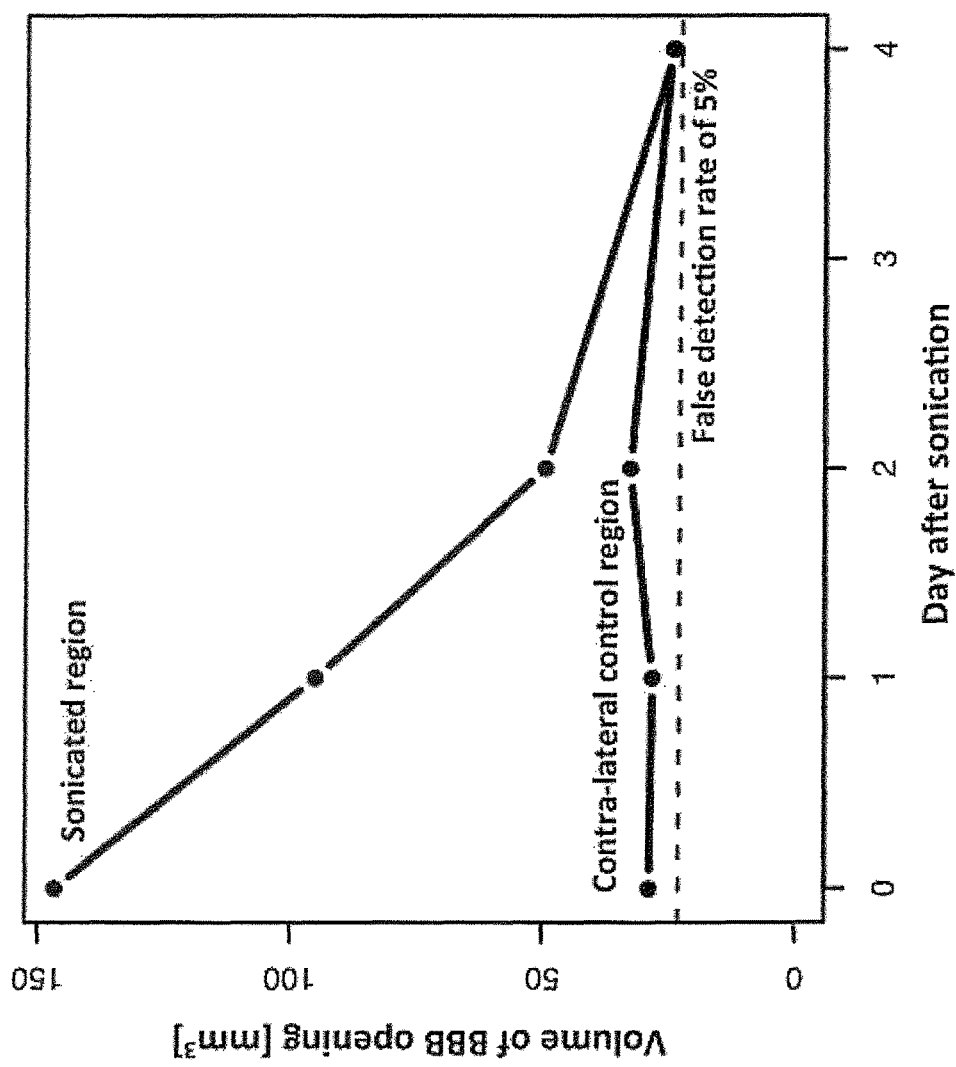
FIG. 11 is an exemplary diagram illustrating BBB closing over time for a single low-pressure sonication illustrated in FIG. 10.

A preliminary experiment to investigate the closing timeline was also performed. Gadodiamide IV injections along with pre- and post-T1-weighted MR sequences were repeated 1, 2, and 4 days after the initial ultrasound treatment. Coronal and sagittal slices of these experiments are illustrated in FIG. 10. Standard T1 contrast enhanced imaging and subsequent analyses indicate a clearly visible, average-sized (126 mm3) BBB opening. FIG. 11 illustrates the opening volume decreased with time. The BBB was almost completely restored two days after sonication. Experiments in mice have shown that the duration of the BBB opening depends on acoustic and microbubble parameters.

FIG. 10 illustrates a series of coronal (left row) and sagittal (right row) T1-weighted MR slices showing the evolution of the BBB opening volume along time. The area with contrast agent diffusion is overlaid in blue. The BBB is restored between day 2 and 4.

FIG. 11 illustrates a timeline of BBB closing for a single low-pressure sonication depicted in FIG. 10. Voxels with a normalized pre-post enhancement of more than 10% were classified as "opened." The total volume of opened voxels decreases as a function of time from the sonication. The opened volume in the contra-lateral control region is constant and close to the one predicted by a false detection rate of 5%.

Some of the above discussed experiments were aimed at testing whether a single spherical transducer at an intermediate frequency of 500 kHz can be used for accurate, repeatable and localized blood-brain barrier disruption in deep subcortical structures. The observed targeting error was sufficiently small (as embodied herein, 2.5±1.2 mm laterally, 1.5±1.3 mm along depth-axis, 3.1±1.3 total) to enable the specific targeting of substructures of the basal ganglia such as the associative or oculomotor caudate.

To further reduce the targeting error potential sources of the error were analyzed. Three potential factors for error include: errors due to deviation of the geometric focus from the intended target (geometric errors), errors due to the analysis of the focal position (analysis errors), and errors due to deviation of actual ultrasound focus from the geometric focus (ultrasound aberration errors).

Over the course of the experiments, the stereotactic manipulator and the targeting routine were repeatedly calibrated. For these calibrations, a metal rod was used that was attached to the stereotaxic manipulator in the same way as the ultrasound transducer. The length of the rod was chosen to match the focal length of the transducer and hence its tip corresponded to the location of geometric ultrasound focus (assuming there were no ultrasound aberrations). This setup enabled targeting of various known positions, such as the interaural point of the stereotax. These measurements routinely found deviations from the intended target about 1-2 mm. Geometric error arises when the setting on the stereotactic manipulator that determines geometric focus is off. The position of the geometric focus can be determined by the 9 degrees of freedom of the stereotactic manipulator. Some of these settings are continuous and prone to error. The ml, ap, and dv settings have 1 mm scales in combination with a vernier scale to enable accuracy on the order of a tenth of a millimeter. The azimuth and elevation scales, however, are divided in steps of 5 and 2 degrees, respectively, without an additional vernier scale. This can enable accuracy of about 1 to 2 degrees. Even small angular deviations can have a big effect on the final position of the geometric focus.

The elevation setting should be correct for an additional reason: If the approach angle deviates from vertical, gravitational forces perpendicular to the approach angle will grow stronger. These gravitational forces can introduce systematic errors for angled approach vectors. The mislocalization in the dorso-ventral direction was strongest for the putamen target, and this target utilized a more angled approach. The ventral mislocalization decreases over time (as shown for example in FIGS. 7 and 8). As such, over the time-course of the experiments described herein, more force was used to fasten the set-screws to maintain the elevation angle against gravitational pull.

Further, the analysis pipeline used to infer the observed focal point can induce additional small errors. The analysis depends on alignment of pre- and post-contrast-enhanced T1 images to a stereotactically aligned reference image. Small errors can arise during the registration process of the pre- and post-images to the reference. Similarly, the alignment of the reference image can fail to perfectly match the intended stereotactic alignment. In addition, the actual position of the animal in the stereotax can vary slightly on a day-by-day basis. Together these factors can contribute up to 1 mm of the random and/or systematic targeting error. Further, the fractional enhancement of the post-relative to the pre-image can be based on noisy T1 MRI images, which can contribute to the overall targeting error.

Mislocalization in the axial direction can occur due to ultrasound aberrations based on in vitro measurements with immersed skull plates. The results herein correspond to the in vitro findings. On average, a 6.5 mm focal shift was observed, compared to the predicted 5 mm focal shift. The additional 1.5 mm can be due at least in part to different ultrasound aberrations in vivo or can be due to geometric and analysis error.

Real-time monitoring based on the frequency content of the backscattered signal was performed to classify the cavitation behavior and hence establish the success and safety of the sonication. Measuring the cavitation spectrum can verify that the microbubbles are correctly excited in situ, i.e., non-linear resonance along the ultrasonic frequency without broadband noise signature of bubbles collapsing or micro-jet streaming (inertial cavitation). This can correspond to a significant HEI (between 15 dB and 25 dB) and no BET. During all experiments performed, (pressures at or below 0.3 MPa) only stable cavitation was observed. Therefore, the PCD monitoring indicated that the procedure can be considered safe and successful. In addition, the HEI can be indicator of the success of the BBB opening in these initial findings. For the cases with an average HEI higher than 5 dB, there was 94% (15/16) of success. The correlation between the HEI and the opening volume in FIG. 8B was not high since the focus was on a small range of pressures (0.20-0.30 MPa).

Focused ultrasound can be used to temporarily disrupt the integrity of the blood brain-barrier in specifically targeted brain regions of rodents and monkeys. Focused ultrasound can also allow clinicians to deliver drugs to specific neural targets. However, certain clinical ultrasound setups can include multiphased ultrasound transducer arrays located inside an MR scanner. This can restrict the use of ultrasound to highly specialized clinical settings. Here, a low-tech single-element 500 kHz spherical transducer ultrasound setup was used that can overcome this challenge. The system is portable, and can use a stereotactic targeting technique independent of MR guided targeting. The systems and techniques of the disclosed subject matter can thus use independent of an MR scanner. The stereotactic targeting procedure is accurate and reliable, and for purpose of illustration and confirmation, the success of the sonication can reliably be inferred using real-time passive cavitation spectral analysis. While successful sonications were usually accompanied by a 10-15 dB HEI, no correlation was found between HEI and opening volume.

As such, the systems and techniques according to the disclosed subject matter can be used to open the BBB in specific brain regions of a subject, largely independent of MRI-guided targeting and/or verification. Hence, in operation, the systems and techniques can provide noninvasive targeted brain-drug delivery to a subject in less specialized clinical settings (e.g., outpatient clinics; community hospitals). Targeting accuracy can be increased by using an individual stereotactically aligned T1 image. However, subsequent sonications can be performed completely independent of MRI.

The results and analyses outlined described herein illustrate that the single-element FUS systems and techniques can be used to accurately and reliably target sub-structures of the basal ganglia. Additionally, it can be desirable to know how long the BBB will stay open before it regenerates and prevents the passage of molecules from the blood to the brain. This can be desirable for at least the following two reasons: the window of opportunity during which drugs can be delivered can be determined and, how long the brain region in question will be exposed to other substances that usually would not cross the intact BBB can also be determined. The duration of the BBB opening can depend at least in part on the precise sonication parameters such as ultrasound pressure and microbubble size. The duration of the BBB opening can range between 12 hours and 5 days. First, the time course of the BBB closing for a single sonication in one of the macaque subjects was measured. Due to the closer similarity between brain structures of the macaque and human species, these measurements can correspond to a time course expected in the human brain. The results from a single exploratory analysis indicated that an average-sized BBB opening (~126 mm$^3$) with moderate in situ ultrasound pressures (0.30 MPa) and 4-5 μm monodisperse microbubbles takes between 2 and 4 days to close.

EXAMPLE 2

For purpose of further illustration and confirmation of the disclosed subject matter, additional exemplary experimental results were obtained according to the techniques disclosed herein. The experimental results included, for example, results of a series of 17 sonications targeting the caudate nucleus (6) and the putamen (11) in the left hemispheres of two macaque monkeys. The analyses are focused on targeting accuracy, the relationship between PCD response and BBB opening volume as well as safety of the procedure. In addition, one exploratory study examined the duration for which the BBB remains open after the sonication.

Both in vitro macaque and human skull techniques as well as in vivo skull effects and realtime monitoring in BBB opening of macaques were performed in this example. Three types of cavitation doses and the cavitation SNR were quantified and used to address the characteristics of cavitation, skull attenuation, and detection threshold. The stable cavitation dose (SCD) representing the overall extent of stable cavitation can be represented as the cumulative harmonic or ultraharmonic emission. The inertial cavitation dose (ICD) can represent the overall extent of inertial cavitation, and can be represented as the cumulative broadband acoustic emission. The cavitation SNR can be represented as the ratio of post- to pre-microbubble administration cavitation doses.

Figure 12:
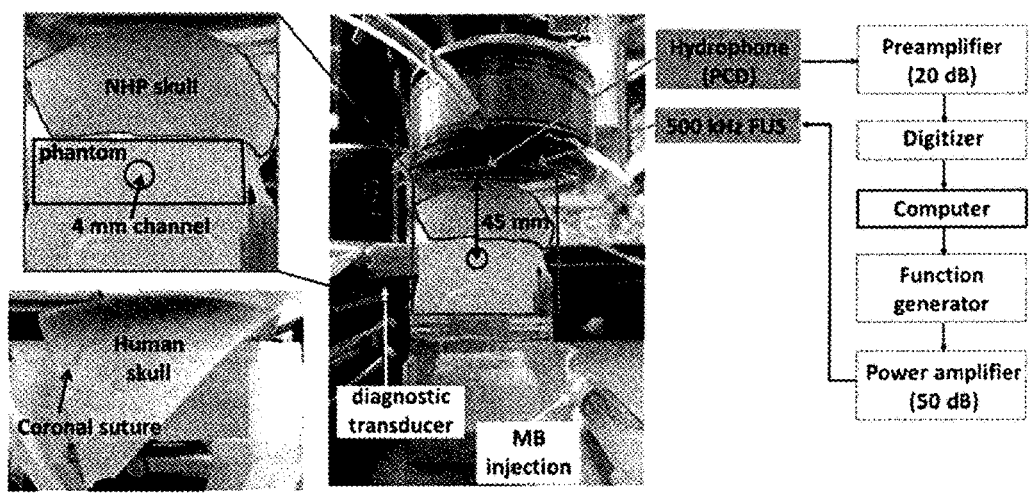
FIG. 12 illustrates another embodiment of a system for real-time, transcranial monitoring of safe blood-brain barrier opening, according to the disclosed subject matter.
Figure 13:
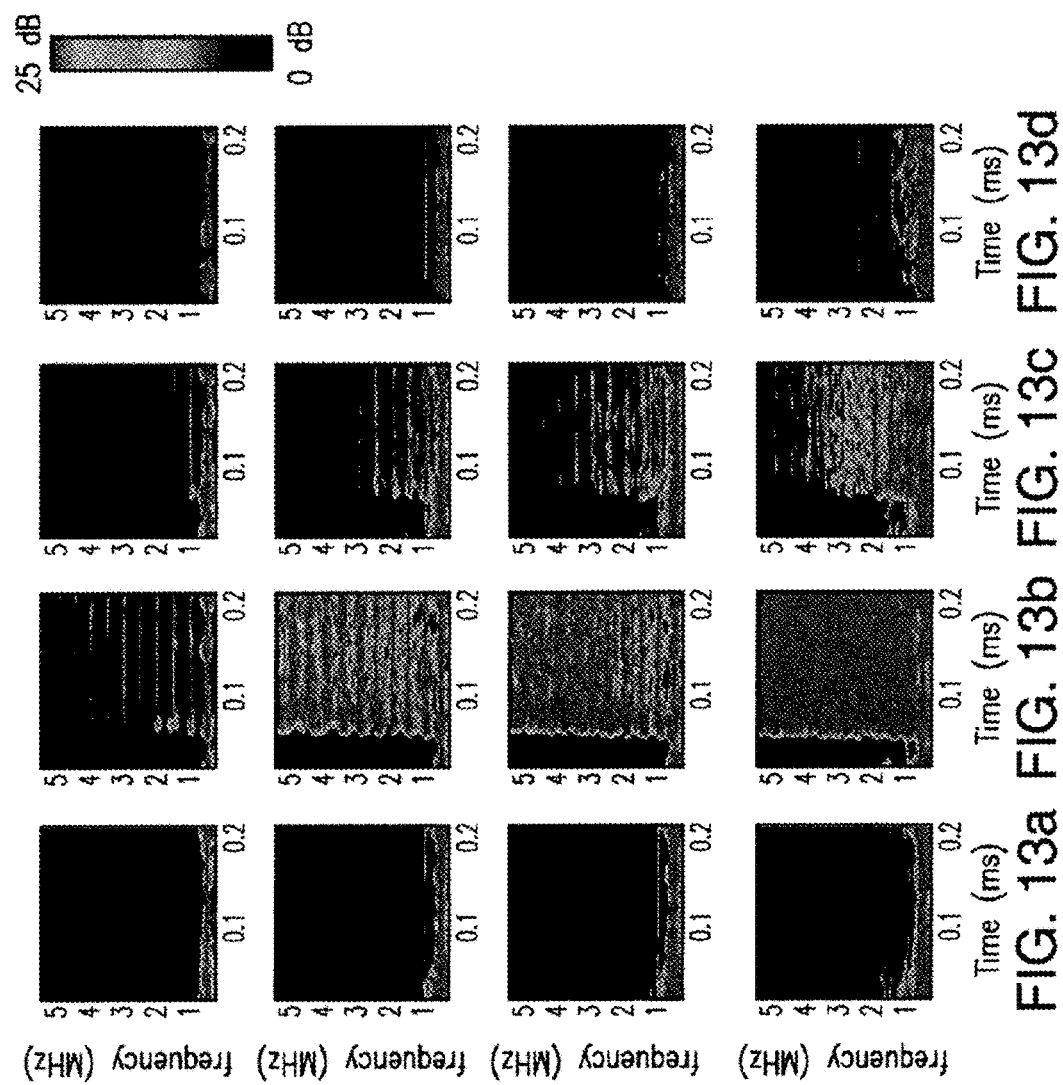
FIGS. 13A-13D are diagrams illustrating in vitro cavitation monitoring: spectrograms. (a) Sonicating water without the skull in place. (b) Sonicating microbubbles without the skull in place. (c) Sonicating microbubbles with the macaque skull in place. (d) Sonicating microbubbles with the human skull in place. (i), (ii), (iii), and (iv) represents 50 kPa, 150 kPa, 200 kPa, and 450 kPa, respectively. The colorbar illustrates the intensity of the spectra, with a dynamic range of 25 dB and 15 dB for macaque and human skull examples, respectively, from the preamplification (macaque: 20 dB, human: 10 dB).

FIG. 12 illustrates an alternative embodiment of a system 200 for real-time, transcranial monitoring of safe blood-brain barrier opening. A single-element FUS transducer (H-107, Sonic Concepts, WA, USA) operated at 0.5 MHz with a −6-dB focal width by length equals to 5.85 mm by 34 mm and a geometric focal depth of 62.6 mm was used for sonication. A spherically focused, flatband hydrophone (Y-107, Sonic Concepts, WA, USA; −6-dB sensitivity: 10 kHz-15 MHz) was coaxially and confocally aligned with the transducer and served as the passive cavitation detector. A PC work station (model T7600, Dell) with a customized program in MATLAB® (Mathworks, MA, USA) was developed to automatically control the sonication through a function generator (model 33220A, Agilent Technologies, CA, USA) followed by a 50-dB amplifier (A075, ENI, NY, USA). The PCD signal acquisition was performed at a 14-bit analog-to-digital converter (Gage Applied Technologies, QC, Canada) (sampling rate: 100 MHz and 50 MHz in vitro and in vivo, respectively). A 20-dB amplification was applied throughout the macaque experiments, while 10 dB was applied for the human skull, due at least in part to increased reflection. All PCD signals in vivo including the frequency spectra and cavitation doses were monitored in real time.

The desiccated macaque skull was obtained from Skull Unlimited (Macaca mulatta, OK, USA) and sectioned to keep the cranial part (including frontal bone, parietal bones, and occipital bone), as shown for example in FIG. 12. The averaged thickness in the ultrasound beam path was 3.09 mm using a caliper at five points of the skull lined in a cross below the transducer, and was degassed for 24 hours prior to use. The desiccated human skull was obtained from The Bone Room (CA, USA), and sectioned, as shown for example in FIG. 12, to keep the frontal and the parietal bones with an averaged thickness of 4.65 mm using the same measuring method described above. The skull was degassed for 48 hours prior to use. The pressures at the focus of the FUS transducer with and without the skulls were calibrated using a bullet hydrophone.

For purpose of illustration an not limitation, a number of sonications performed was summarized in Table 1. In-house, lipid-shell, monodisperse microbubbles (median diameter: 4-5 μm) were diluted to 2×105 bubbles/mL and injected to the 4-mm-in-diameter channel in the acrylamide phantom before and after placing the skull. The channel was roughly 45 mm and 25 mm below the macaque and the human skull, respectively. The PCD with the hydrophone and the diagnostic B-mode imaging system (Terason, MA, USA) were separately used to monitor the sonication (peak negative pressure (PNP): 50-450 kPa, pulse length: 100 cycles (0.2 ms) and 5000 cycles (10 ms), pulse repetition frequency (PRF): 10 Hz, duration: 2 s) in order not to interfere with the PCD. B-mode images of bubble disruption were acquired to ensure the FUS focusing at the channel, which was performed through a linear array transducer (10L5, Terason, MA, USA; center frequency: 5.1 MHz) placed transversely to the FUS beam.

TABLE 1

Number of in vitro sonications.

| | | | Without microbubbles | With microbubbles |
|---|---|---|---|---|
| Skull effect (100 cycles) | Macaque | No skull | 41 | 49 |
| | | Skull | 33 | 46 |
| | Human | No skull | 60 | 60 |
| | | Skull | 70 | 81 |
| Pulse length effect (5000 cycles) | | No skull | 20 | 20 |

The in vitro configuration was implemented similarly to the in vivo conditions in terms of targeting through the skull. That is, FUS was applied through the parietal bone next to the sagittal suture, corresponding to the position for targeting the thalamus, putamen, and caudate nucleus. The 4-mm channel was chosen to accommodate the area of bubble disruption at the highest pressure (450 kPa). The low microbubble concentration was chosen in order to reduce or minimize the bubble-bubble interaction (the mean distance between bubbles is 58.5 mm) while being captured for B-mode visualization. Sonication using 5000-cycle pulses without the skull in place was also performed.

Four male rhesus macaques (Macaca mulatta) weighing between 6-11 kg were used to perform in vivo techniques according to the disclosed subject matter. Two separate sets of experiments, i.e., one set for the in vivo skull effect and another for BBB opening in non-human primates were performed, and the number of sonications was summarized in Table 2. Microbubbles were intravenously injected, and the total number of microbubbles administered was determined based on the animal's weight. For the purpose of BBB opening, a bolus of microbubbles ($2.5 \times 10^8$ bubbles/kg) was injected and the sonication (PNP: 250-600 kPa, pulse length: 10 ms, PRF: 2 Hz, duration: 2 min) started at the beginning of injection. To study the in vivo skull effect, a bolus of microbubbles ($1.25 \times 10^8$ bubbles/kg) were injected after the BBB opening sonication. Ten seconds after the injection when the microbubbles perfused to the brain, a consecutive sonication at ramp-up pressures was started (PNP: 50-700 kPa, pulse length: 100 cycles (0.2 ms) or 5000 cycles (10 ms), PRF: 2 Hz, duration: 10 s). The targeted regions were thalamus and putamen.

TABLE 2

Number of in vivo sonications.

| | Pulse length | Without microbubbles | With microbubbles |
|---|---|---|---|
| Skull effect | 100 cycles | 8* | 8* |
| | 5000 cycles | 14** | 14** |
| BBB opening | 5000 cycles | 40 | 40 |

*6 at 700 kPa.

TABLE 2-continued

Number of in vivo sonications.

| | Without | With |
| Pulse length | microbubbles | microbubbles |

**12 at 700 kPa.

Magnetic Resonance Imaging (3T, Philips Medical Systems, MA, USA) was performed 0.5 h after the sonication to confirm BBB opening and assess safety. Spoiled Gradient-Echo T1-weighted sequence (TR/TE=20/1.4 ms; flip angle=30°; NEX=2; spatial resolution: 500×500 µm2, slice thickness: 1 mm with no interslice gap) before and 40 min after intravenously injecting the contrast agent gadodiamide (Omniscan®, GE Healthcare, NJ, USA; dosage: 0.2 mL/kg), was used to visualize the opening, with the analysis described in the following paragraph. T2-weighted sequence (TR/TE=3000/80 ms; flip angle=90°; NEX=3; spatial resolution: 400×400 µm2, slice thickness: 2 mm with no interslice gap) was performed for detecting edema. Susceptibility-weighted imaging (SWI, TR/TE=19/27 ms; flip angle=15°; NEX=1; spatial resolution: 400×400 µm2, slice thickness: 1 mm with no interslice gap) was performed for detecting hemorrhage.

Analysis for the opening volume across the experiments included image re-alignment, enhancement evaluation, and volume calculation. The pre-contrast and post-contrast images were aligned to the individual stereotactically aligned T1-weighted images acquired using FSL's FLIRT to ensure the alignment of the pre- to post-contrast images. The ratio of the post- to the pre-contrast images was taken and normalized by setting 0 and 1 to the mean of the contralateral region oppose to the sonicated region (a circle of 6.25 mm in diameter in the horizontal slice) and the anterior cerebral artery (a circle of 1.75 mm in diameter in the horizontal slice), respectively, and the opening region was thresholded by three times standard deviation of the contralateral (unsonicated) region. The volume was represented as the accumulated voxels over the threshold in the sonicated region times the voxel size.

The PCD signals, frequency spectra, and spectrograms (8-cycle Chebyshev window, 98% overlap, 4096-point Fast Fourier Transform) were used to monitor the cavitation using MATLAB®. To quantify the cavitation level-time derivative of the cavitation dose, the harmonic, ultraharmonic, and the broadband signals in the spectra for each pulse were separately filtered. The stable cavitation level based on harmonics only (dSCDh) was represented as the root-mean squared amplitude of the harmonic signals in a single pulse, with the harmonic signals defined as the maxima in the 20-kHz (−6-dB width) range around the harmonic frequency (0.5f*n) in the frequency spectrum. The stable cavitation level from ultraharmonics only (dSCDu) was represented as the root-mean squared amplitude of the ultraharmonic signals in a single pulse, with the ultraharmonic signals defined as the maxima in 20 kHz around the ultraharmonic frequency (0.5f*n+0.25f) in the frequency spectrum. The inertial cavitation level (dICD) was represented as the root-mean squared amplitude of the frequency spectrum after excluding the harmonics (360 kHz around the harmonic frequency) and ultraharmonics (100 kHz around the ultraharmonic frequency).

The cavitation dose for each sonication was represented as the cumulative sum of the cavitation level in 1.25-5.00 MHz for every pulse; the cavitation SNR, the ratio of post- to pre-microbubble administration cavitation doses.

$$\text{Cavitation dose (CD)} = \Sigma\_(t=0-T) [\![ dCD ]\!] \_t = \Sigma\_(t=0-T) [\![ \sqrt{((S\hat{}2)^-)} ]\!] \_t \quad (4)$$

$$\text{Cavitation SNR} = 20\log([\![ CD ]\!] \_\text{post} / [\![ CD ]\!] \_\text{pre}) \quad (5)$$

where t can represent the time for each pulse; T, the sonication duration; CD, the cavitation dose (SCDh, SCDu, and ICD for harmonics, ultraharmonics, and broadband emissions, respectively); $[\![ dCD ]\!] \_t$, the cavitation level for the pulse at time t (dSCDh, dSCDu, and dICD for harmonics, ultraharmonics, and broadband emissions, respectively); $[\![ \sqrt{((S\hat{}2)^-)} ]\!] \_t$ the root-mean squared amplitude of the harmonic/ultraharmonic/broadband signals in the frequency spectrum for the pulse at time t; $[\![ CD ]\!] \_\text{post}$, the post-microbubble administration cavitation dose; $[\![ CD ]\!] \_\text{pre}$, the pre-microbubble administration cavitation dose.

The frequency range used to quantify the cavitation level was 1.25-5.00 MHz to cover the strong harmonics, ultraharmonics, and broadband emission, while reducing the linear and nonlinear scattering from the tissue and the skull. The quantification of the SCDh and the SCDu was based at least in part on the acoustic emissions generated by the stable cavitation, including harmonics and ultraharmonics. The harmonics and ultraharmonics were quantified separately due at least in part to a difference of the spectral amplitudes. Furthermore, the harmonics can be considered a result of volumetric oscillation, and the ultraharmonics and subharmonics can relate to nonspherical bubble oscillation. To quantify the ICD, the width of the spectral window for the broadband signals was chosen in order to reduce or minimize both the electronic noise and the increase due to the harmonic peaks (i.e., the window width is large enough to reduce or minimize the electronic noise by averaging and not to cover the broadening part of harmonic peaks).

In the in vitro techniques, for purpose of illustration and confirmation of the disclosed subject matter, an unpaired two-tailed Student's t-test was used to determine if the treatment (post-microbubble administration) was significantly higher than the control (pre-microbubble administration) for each pressure. In the in vivo skull effect techniques, for purpose of illustration and confirmation of the disclosed subject matter, a paired two-tailed Student's t-test was used to determine if the treatment (post-microbubble administration) was significantly higher than the control (pre-microbubble administration) for each pressure in each animal.

FIGS. 13A-13D illustrate exemplary PCD spectrograms before and after placing the skull. Before placing the skull, the amplitude of harmonics, ultraharmonics as well as the broadband signals increased significantly with pressure after microbubble administration (FIG. 13B) when compared to the control (FIG. 13A), in which the second harmonic became significant at and above 150 kPa. The broadband signals increased mostly within the range of 3-5 MHz according to the results at 150 kPa and 200 kPa in FIG. 13B. After placing the macaque skull (FIG. 13C), the high frequency components were attenuated, while the signals remained detectable at the lowest pressure (50 kPa). After placing the human skull (FIG. 13D), the frequency components below 3 MHz were detected only at and above 100 kPa.

B-mode cine-loops were also used to monitor the cavitation separately. FIGS. 14A-14D shows the images of the microbubbles in the channel phantom after sonication. The microbubbles were found to collapse at and above 200 kPa evidenced by the loss of echogenicity in the focal region in cases without the skull (FIG. 14A), with the macaque skull (FIG. 14B), with the human skull (FIG. 14C), and using longer pulses without the skull (5000 cycles in FIG. 14D). The mean diameter of the hypoechogenic area at 200 kPa and 450 kPa was 1.3 mm and 4 mm, respectively.

FIGS. 15A-15I are diagrams illustrating cavitation doses with and without the skull in place using 100-cycle pulses. In the macaque skull examples (FIGS. 14A-14C), the SCDh, the SCDu, and the ICD without placing the skull were significantly higher (p<0.05) than the control at and above 50 kPa, which also increased monotonically with pressure. After placing the macaque skull, the SCDh was detectable (p<0.05) at all pressures, whereas the detection pressure threshold for both the SCDu and the ICD increased to 150 kPa. In the human skull examples (FIGS. 15D-15F), the SCDh was detectable at and above 100 kPa after placing the skull. For the SCDu, the detection pressure threshold increased to 250 kPa. For the ICD, it became 350 kPa. The SCDh at and above 400 kPa was undetected at least in part because the control signal with the human skull was strong. While the detection pressure threshold changed slightly after placing the macaque and the human skull, the sensitivity of cavitation doses to pressure changes remained the same.

Figure 15G:
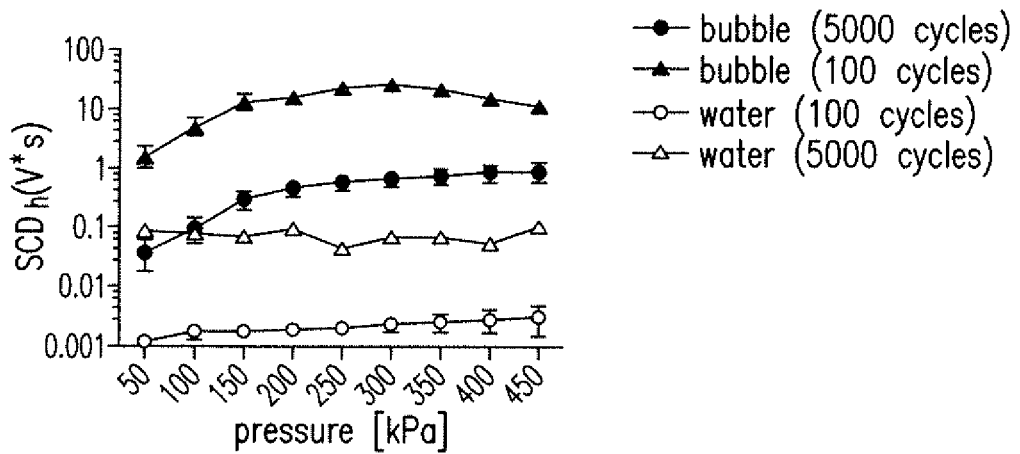
Figure 15H:
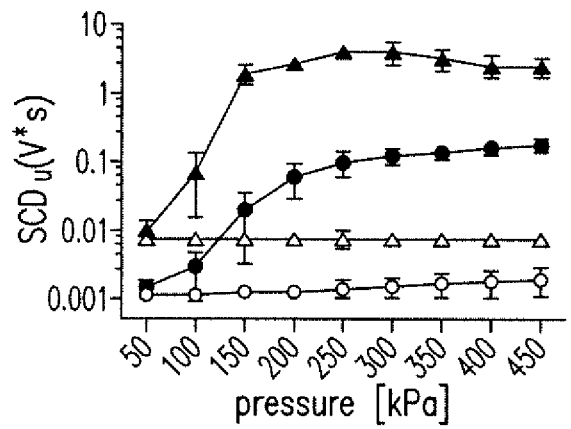
Figure 15I:
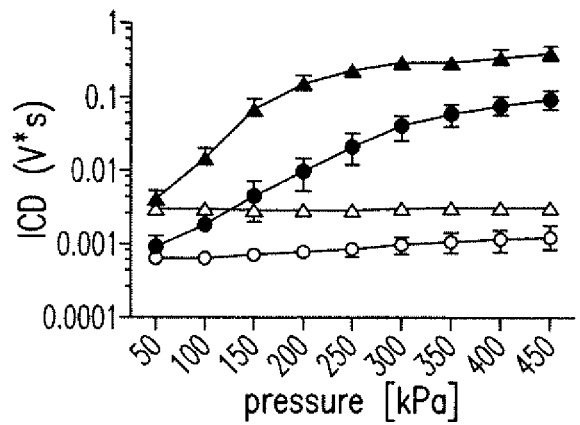

The pulse length effect on the cavitation dose was also examined. FIGS. 15G-15I illustrate the cavitation doses with 100-cycles and 5000-cycle pulse lengths. The SCDh using 100-cycle pulses increased monotonically with pressure increase, whereas the SCDh with 5000-cycle pulses reached a maximum at 300 kPa and started to decrease at pressures above 300 kPa. The SCDu using 100-cycle pulses increased monotonically with pressure, while the SCDu using 5000-cycle pulses reached a plateau at 250 kPa and started to decrease at higher pressures. The ICD using 100-cycle and 5000-cycle pulses both increased monotonically with pressure increase, and the latter increased at a faster rate. All of the cavitation doses of 5000-cycle pulses were higher than that of 100-cycle pulses.

FIGS. 16A-16D are diagrams illustrating the cavitation SNR, illustrating the sensitivity of PCD using pulse lengths, the detection limit, and skull attenuation. Before placing the skull, the cavitation SNR for the SCDh, SCDu, and ICD using 100-cycle pulses (FIG. 16A) ranged within 28.6-49.1 dB, 2.1-38.9 dB, and 3.1-37.0 dB, respectively. Followed by the SCDu and the ICD, the cavitation SNR for the SCDh was the highest. The cavitation SNR for the SCDh, SCDu, and ICD using 5000-cycle pulses (FIG. 16B) ranged within 24.8-54.6 dB, 2.2-54.8 dB, and 2.9-41.9 dB, respectively. Both the cavitation SNR for the SCDh, SCDu reached a plateau at 250 kPa, while it increased monotonically for the ICD.

Figure 16A:
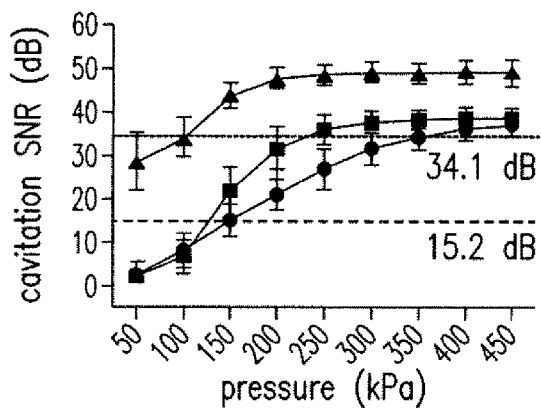
FIGS. 16A-16D are diagrams illustrating additional characteristics according to the disclosed subject matter (a) without the skull in place using 100-cycle pulses, (b) without the skull in place using 5000-cycle pulses, (c) with the macaque skull in place using 100 cycles, and (d) with the human skull in place using 100 cycles. The error bar shows the standard deviation. The dash lines in (a) represent the transcranial detection threshold (macaque: 15.2 dB, human: 34.1 dB).
Figure 16B:
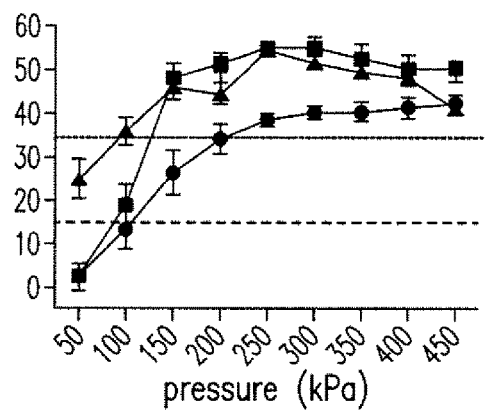
Figure 16C:
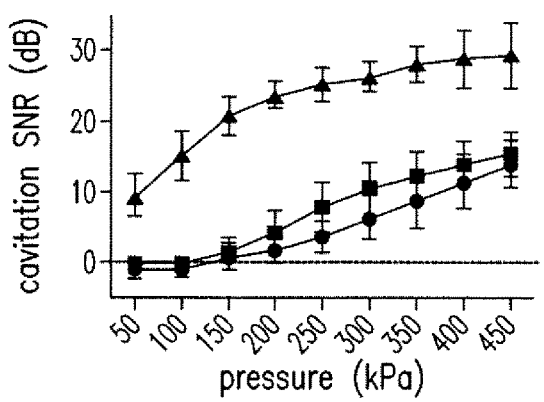
Figure 16D:
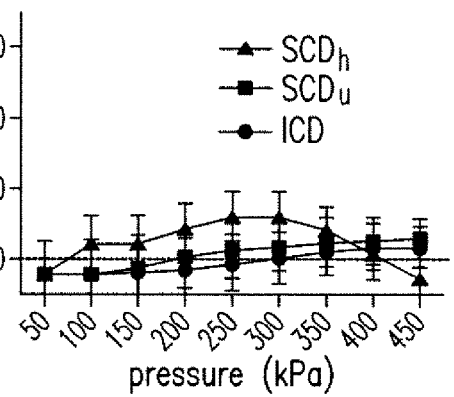

FIGS. 16C-16D illustrate the cavitation SNR using 100-cycle pulses through the skull. The cavitation SNR through the macaque skull (FIG. 16C) corresponding to the statistically significant SCDh, SCDu, and ICD through the macaque skull (FIGS. 15A-15C) ranged within 9.7-29.4 dB, 1.6-15.6 dB, and 1.1-14.1 dB, respectively. The cavitation SNR through the human skull (FIG. 16D) corresponding to the statistically significant SCDh, SCDu, and ICD through the human skull (FIGS. 15D-15F) ranged within 2.4-6.2 dB, 1.4-3.0 dB, and 1.2-1.9 dB, respectively. For the cavitation SNR with the skull lower than 1 dB, the corresponding cavitation doses were lower. As such, 1 dB can be represented as the detection threshold (or SNR threshold), meaning that the PCD signals were more reliable when the cavitation SNR exceeded 1 dB.

Figure 14:
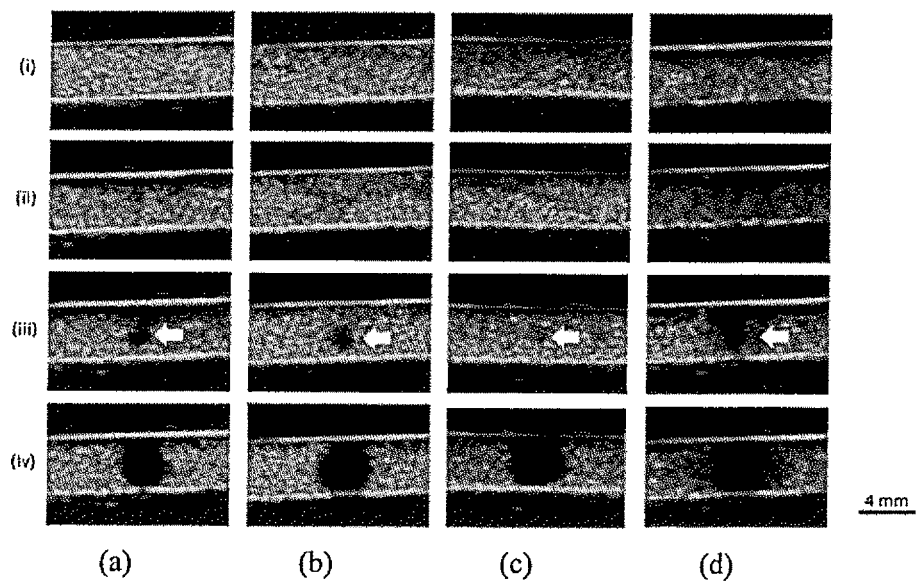
FIGS. 14A-14D are exemplary B-mode images in transverse plane after the sonication. (a) Without the skull in place using 100 cycles. (b) With the macaque skull in place using 100 cycles. (c) With the human skull in place using 100 cycles. (d) Without the skull in place using 5000 cycles. (i), (ii), (iii), and (iv) represents 50 kPa, 150 kPa, 200 kPa, and 450 kPa, respectively. The arrows indicate the spot losing echogenicity.

As described above, by correlating the cavitation SNR with the skull (FIGS. 16C-16D) to the cavitation doses with the skull (FIGS. 15A-15F), when the cavitation SNR exceeded 1 dB—defined as the detection threshold for PCD—the transcranially acquired cavitation doses were statistically significant. In order to assess the skull attenuation, the cavitation SNR without the skull (FIG. 14A) was then compared with the cases with the skull surpassing the 1-dB SNR limit (FIGS. 14C-14D). The SNR without the skull was above 15.2 dB and 34.1 dB in order to be detected through the macaque and the human skull, respectively. The skull attenuation was determined by dividing by the skull thickness: 4.92 dB/mm and 7.33 dB/mm for the macaque and human, respectively.

Figure 17A:
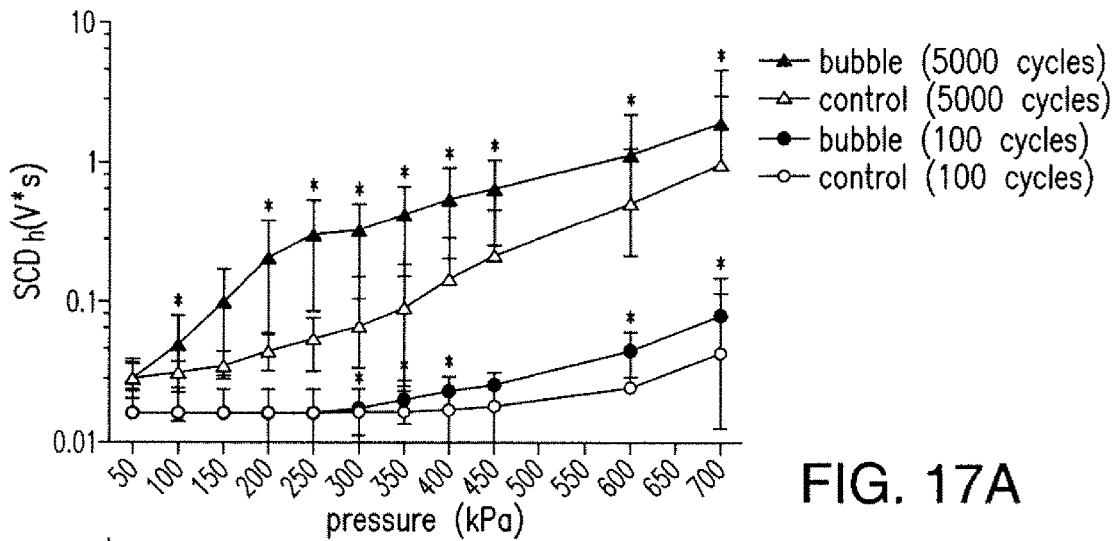
FIGS. 17A-17C are diagrams illustrating additional characteristics according to the disclosed subject matter of in vivo cavitation doses using 100 and 5000 cycles. (a) $SCD_h$. (b) $SCD_u$. (c) ICD. *: p<0.05. The error bar shows the standard deviation.
Figure 17B:
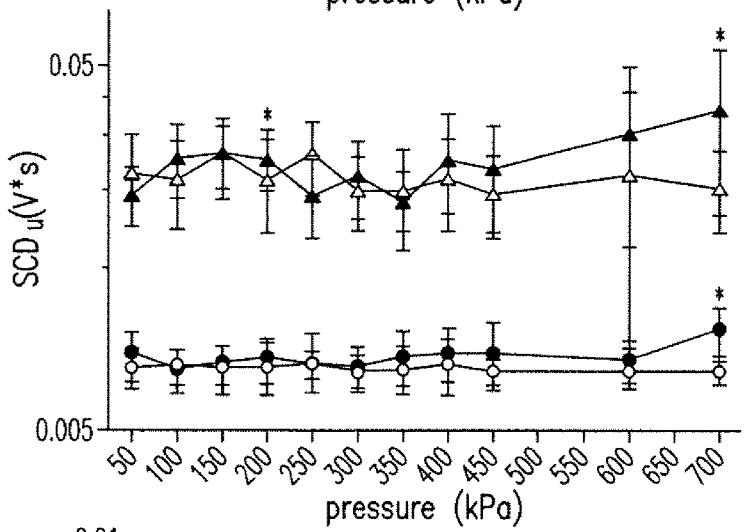
Figure 17C:
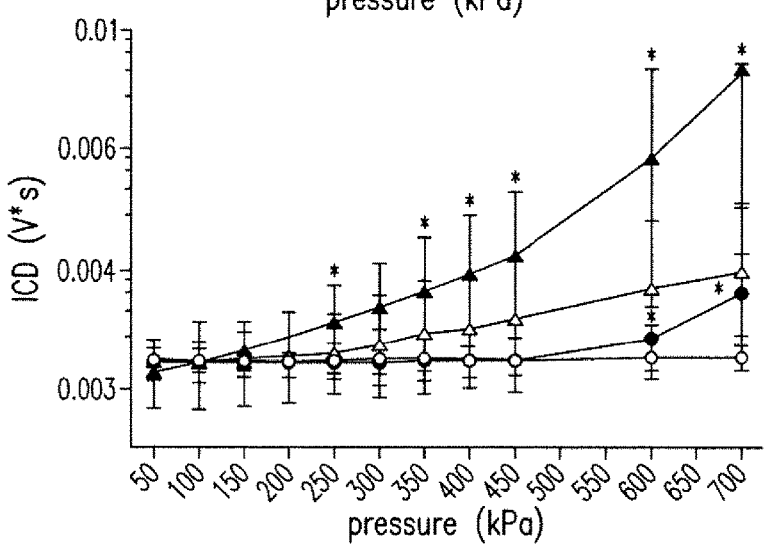

For purpose of illustration and confirmation of the disclosed subject matter, in vivo skull effects at different pressures and different pulse lengths were examined and compared with those of the in vitro techniques. FIGS. 17A-17C are diagrams illustrating the cavitation doses using 100- and 5000-cycle pulses. When applying 100-cycle pulses, the SCDh, SCDu, and ICD were significantly higher than the control at and/or above 300 kPa, 700 kPa, and 600 kPa, respectively. When applying 5000-cycle pulses, the SCDh, SCDu, and ICD were significant at pressure lower than that for the 100-cycle pulses: at and above 100 kPa, at 200 kPa and 700 kPa, and at and above 250 kPa, respectively. The cavitation dose when applying 5000-cycle pulses was higher than that with 100-cycle pulses. As such, the cavitation doses increased monotonically with pressure increase. The SCDh using 100-cycle pulses at 450 kPa, the SCDh using 5000-cycle pulses at 150 kPa, and the ICD using 5000-cycle pulses at 300 kPa ($0.05<p<0.06$) showed higher variability.

Figure 18A:
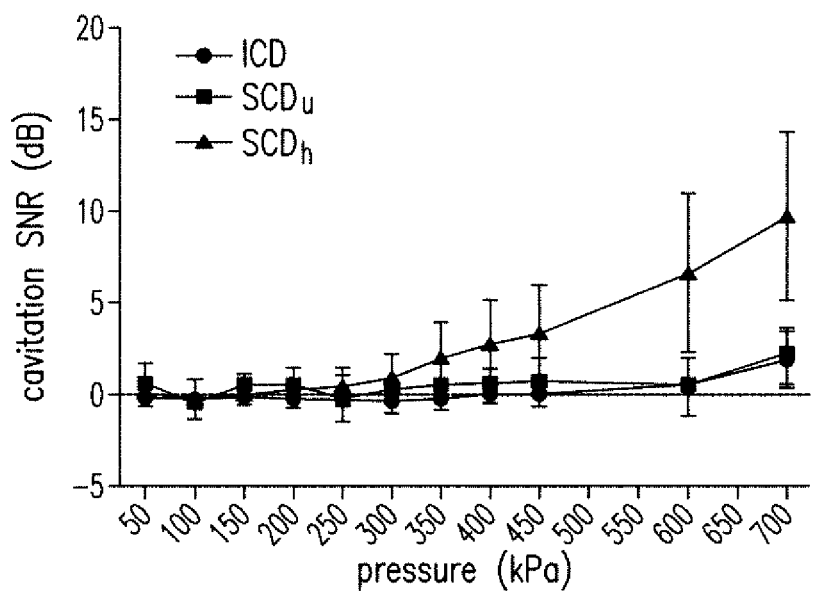
FIGS. 18A-18B are diagrams illustrating additional characteristics according to the disclosed subject matter of in vivo cavitation SNR using (a) 100-cycle and (b) 5000-cycle pulses. The error bar shows the standard deviation.
Figure 18B:
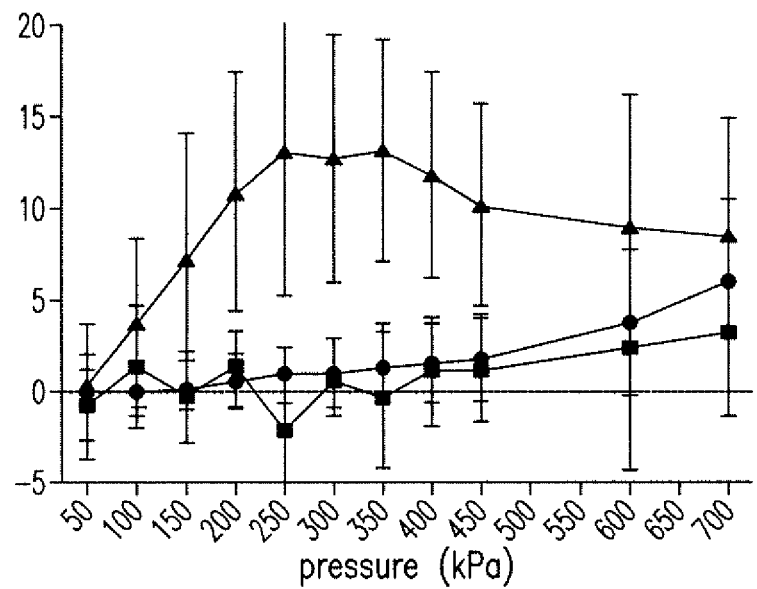

FIGS. 18A-18B are diagrams illustrating the cavitation SNR for the skull effect using 100- and 5000-cycle pulses. When applying 100-cycle pulses (FIG. 18A), the cavitation SNR for SCDh, SCDu, and ICD ranged within 1.2-9.8 dB, 2.3 dB, and 0.7-2.1 dB, respectively. The cavitation SNR increased monotonically for the SCDh and ICD, and fluctuated for the SCDu. When applying 5000-cycle pulses (FIG. 18B), the cavitation SNR for the SCDh, SCDu, and ICD ranged within 3.8-13.3 dB, 1.4-3.5 dB, and 1.0-6.1 dB, respectively, reached a plateau for the SCDh at 250 kPa, and started to decrease at 400 kPa. For the SCDh, the cavitation SNR fluctuated at low pressures and increased monotonically at and above 400 kPa. For the ICD, the cavitation SNR increased monotonically without fluctuating or reaching a plateau. The cavitation SNRs for pressures where significant cavitation signals were detected were all above the 1-dB SNR threshold, with the exception for SCDu (57% of the measurements passing the detection threshold were statistically insignificant).

Realtime PCD monitoring during BBB opening according to the disclosed subject matter was performed. FIGS. 19A-19D illustrate four cases of PCD monitoring and the corresponding opening results in MRI at different pressures. The MRI showed BBB opening in two macaques in the thalamus and the putamen at pressures ranging from 250 kPa to 600 kPa, with the opening volume of 338.6, 223.8, 213.4, and 262.5 mm3, respectively. The volume increased with pressures in the same macaque (FIGS. 19B-19D) in general, and the range varied across animals. The dSCDh reached a plateau in 10-30 seconds after injecting microbubbles and was kept at the same level for the rest of sonication duration. The dSCDu remained generally undetected. The dICD increased by 3.18 dB at 350 kPa and 0.19 dB at 450 kPa from the end of the sonication to the beginning, and remained unchanged at 275 kPa and 600 kPa.

For purpose of illustration, FIGS. 20A-20D illustrate an exemplary safety assessment technique using T2-weighted MRI and SWI corresponding to the four BBB opening cases in FIGS. 19A-19D. In each example, no edema or hemorrhage was detected, corresponding to the PCD monitoring results for which little or no ICD increase was seen during sonication.

For purpose of illustration and confirmation of the disclosed subject matter, as embodied herein, to investigate the sensitivity, reliability, and the transcranial cavitation detection limit in macaques and humans, both in vitro macaque and human skull techniques as well as in vivo techniques for the skull effect and BBB opening in macaques were performed. The transcranial PCD was found sensitive to detect cavitation signals at pressures as low as 50 kPa. The transcranial detection threshold (1-dB SNR threshold) served as a guide to determine reliable detection. Realtime PCD monitoring was performed during BBB opening, in which safe opening and reliable detection was achieved using long pulses.

B-mode imaging was used to visualize the cavitation, to ensure the focal alignment to the channel and the pressure in situ. The imaging visualized cavitation by the maintenance or loss of echogenicity, representing stable or inertial cavitation, respectively, and confirmed good focal alignment to the channel before and after placing the skull by detecting the bubble collapse at the center of the channel. The pressure in the channel was confirmed after placing the skull since the loss of echogenicity became detectable at 200 kPa.

The PCD was utilized as an indirect monitoring tool. The PCD was shown to be more sensitive than B-mode imaging at least in part because PCD detected inertial cavitation at 50 kPa, lower than the lowest pressure losing echogenicity (200 kPa). Detecting bubble destruction in B-mode imaging can be affected by its spatial and contrast resolution, which can be unable to detect a smaller amount of bubble destruction at pressures lower than 200 kPa. As such, B-mode imaging was used to supplement to the PCD results rather than to determine the inertial cavitation threshold. The inertial cavitation occurred at 50 kPa due at least in part to low excitation frequency, long pulse lengths, and low stiffness of the in-house microbubbles with a 4-5 μm diameter.

The pulse length affected the characteristics of the cavitation doses (FIGS. 15A-15I). Using 100-cycle pulses, the cavitation doses increased monotonically with pressure increase as the magnitude of bubble oscillation increased. Furthermore, using long pulses (5000 cycles) was found to generate higher cavitation doses. The ICD still increased monotonically with pressure increase, while the SCDh and the SCDu reached a plateau at 250 kPa. Under a long-pulse excitation, a larger number of microbubbles underwent stable and inertial cavitation, and stable cavitation reached a plateau and started to decrease when most microbubbles were undergoing inertial cavitation and collapse immediately without contributing to stable cavitation. The microbubbles undergoing stable cavitation diffused faster using longer pulses and failed to enhance the SCDh.

Through the skull the change of cavitation doses to pressure change remained the same, while the pressure threshold for the cavitation doses becoming detectable varied depending on the type of cavitation doses and the skull (FIGS. 15A-15I). The monotonical increase of cavitation doses to pressure increase remained the same after placing the macaque and the human skull for signals surpassed the skull attenuation. The pressure threshold to detect the SCDh through the macaque skull was unchanged, while it increased for the SCDh and ICD; for the human skull, the threshold increased for the three types of cavitation doses. For all types of cavitation doses, the pressure threshold for the SCDh was the lowest, followed by the SCDu and ICD.

The SCDh remained detectable through the skull at 50 kPa and 100 kPa for macaques and 100 kPa, respectively. For the SCDu and ICD, the pressure threshold increased to 150 kPa and 350 kPa for macaques and human respectively due at least in part to low signal intensity, and the ultraharmonics and the broadband emissions occurred at 50 kPa.

With respect to the in vivo techniques, using 100-cycle and 5000-cycle pulses, the SCDh as well as the ICD generally increased monotonically with pressure. The SCDh for the 5000-cycle pulse did not reach a plateau, which can be due at least in part to nonlinear scattering from the skull and/or air trapped between the transducer and the animal's skin. The SCDu from the less frequent ultraharmonics can be attributed to the biological environment such as blood, capillary, and blood vessel. The varying blood pressure can also contribute to variation in the SCDu. The inertial cavitation was detected at and above 250 kPa, though microbubble collapse can occur at lower pressures.

The cavitation SNR was determined and used to investigate the sensitivity and reliability of PCD under different conditions such as varied pressures and pulse lengths, and corresponding skull effects. In this manner, the transcranial detection threshold (1-dB SNR threshold), the skull attenuation, and other parameters can be determined. To achieve reliable PCD, the cavitation SNR can be increased in any or all of three ways: increasing the pressure, the pulse length, and/or the number of microbubble injected. Using long pulse lengths was found effective in increasing the cavitation SNR at low pressures, while the cavitation SNR for the SCDh decreased at high pressures due to the cavitation characteristics and nonlinear skull scattering. Increasing the number of microbubbles injected can also improve the cavitation SNR, at least in part because the inertial cavitation can be detected at low pressures (250 kPa) in the in vivo skull effect examples after a second bolus injection of microbubbles.

The cavitation signals can be considered reliable through the skull, particularly where the cavitation SNR was above 1 dB, such that the signals were strong enough to surpass skull attenuation. The 1-dB SNR threshold was determined in the in vitro study and confirmed in the in vivo study. As in both studies, the cavitation doses generally showed statistical significance when using this guide. The transcranial detection threshold can also provide an indication of inertial cavitation detected, and can indicate reliable PCD for all types of cavitation doses.

As described herein, the attenuation by the human skull was higher than that for macaque, which can be due at least in part to higher skull density, stronger nonlinear ultrasound transmission, stronger reflections and/or different extents of mode conversion. The cavitation SNR can be increased to surpass the detection threshold, for example and without limitation, by increasing the pressure, the pulse length, or the number of microbubbles injected as described herein. The in situ cavitation strength can be estimated by combining the transcranial PCD measurements exceeding the transcranial detection threshold with the skull attenuation acquired from simulation or ex viva measurement to assess the treatment outcome.

Nonlinear ultrasound scattering due at least in part to the skull can also affect the detection of harmonies. Nonlinear scattering from the human skull was appared above 450 kPa (FIG. 15D), affecting the detection of the harmonics (SCDh) generated by the microbubble cavitation. Higher pressure was applied in order to compensate for the 80% of pressure attenuation through the human skull, which can create or increase nonlinear scattering. The FUS focus was 25 mm below the human skull, can increase nonlinear effects compared to deeper focus. Trapped air can also be present. Nonlinear effects can affect the detection of the SCDh, which can lead to overtreatment based on the monitoring.

Realtime monitoring of the cavitation doses was performed during BBB opening using 5000-cycle pulses, providing the information of bubble perfusion and the cavitation level. Furthermore, the use of long pulses facilitated reliable PCD monitoring and opening at low pressures. By monitoring the SCDh, the time for microbubbles perfuse to the sonicated region as well as the microbubble persistence during the entire treatment can be monitored at pressures as low as 250 kPa. By monitoring the ICD, the safety of the treatment can be determined in real time at least in part because low or no inertial cavitation was detected in the cases of safe BBB opening. Low or no ICD obtained during BBB opening experiments (FIGS. 19A-19D) compared to the in vivo skull effect (FIG. 17A-17C) was due at least in part to lower number of microbubbles circulating during BBB opening, at least in part because increase of ICD was obtained in the same animal after a second bolus injection of microbubbles for in vivo skull effect.

Figures 19A, 19B:
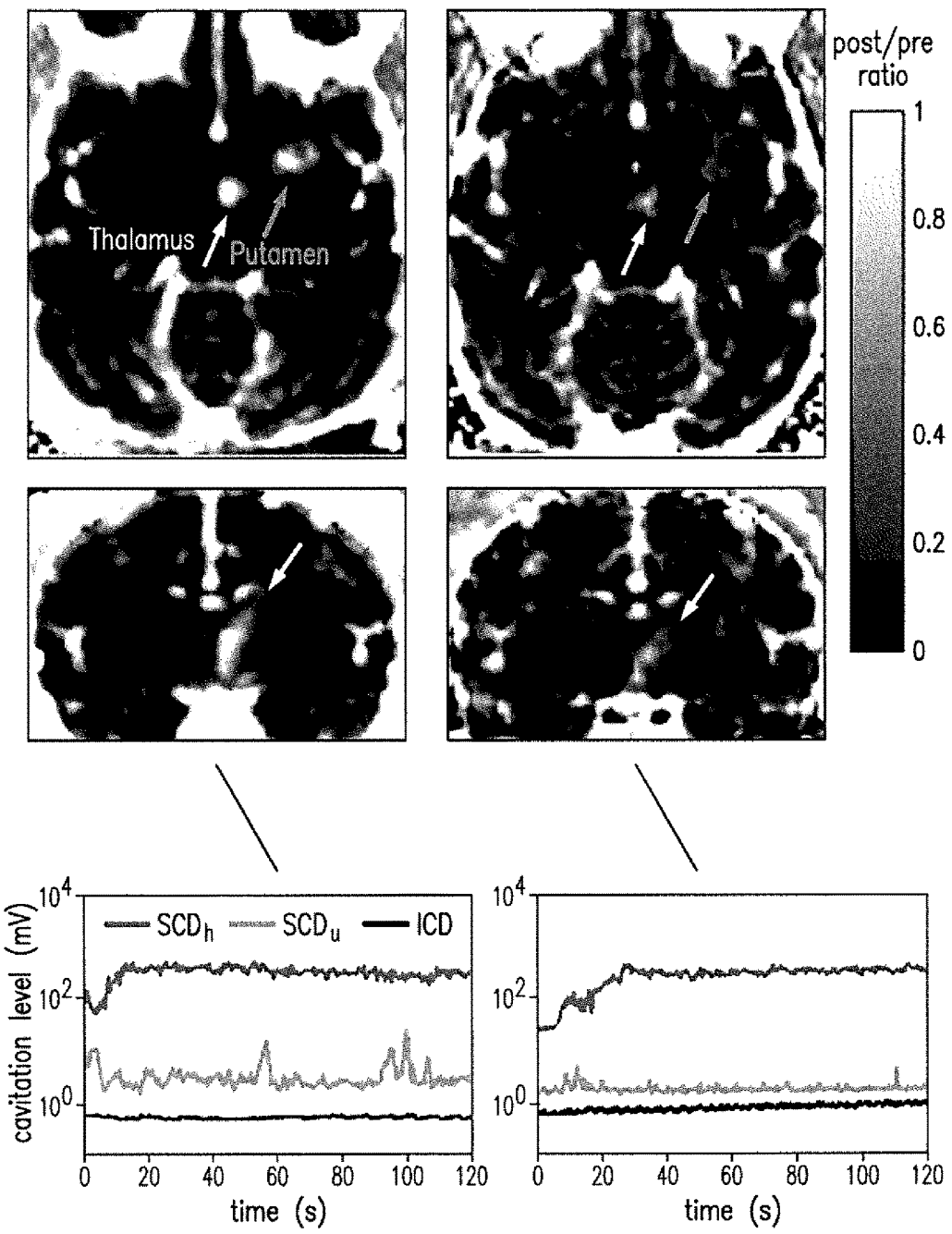
FIGS. 19A-19D are diagrams illustrating in vivo BBB opening according to the disclosed subject matter at (a) 275 kPa, (b) 350 kPa, (c) 450 kPa, and (d) 600 kPa in the thalamus (orange arrow) and the putamen* (green arrow). The upper and middle rows show the post-contrast T1-weighted images in axial and coronal view respectively, in which the colormap shows the enhancement ratio as compared to the pre-contrast images. The opening volume was 338.6, 223.8, 213.4, and 262.5 mm³, respectively. The bottom row shows the realtime monitoring of $SCD_h$, $SCD_u$, and ICD for sonicating the thalamus, and that for the putamen was similar and is not shown.
Figures 19C, 19D:
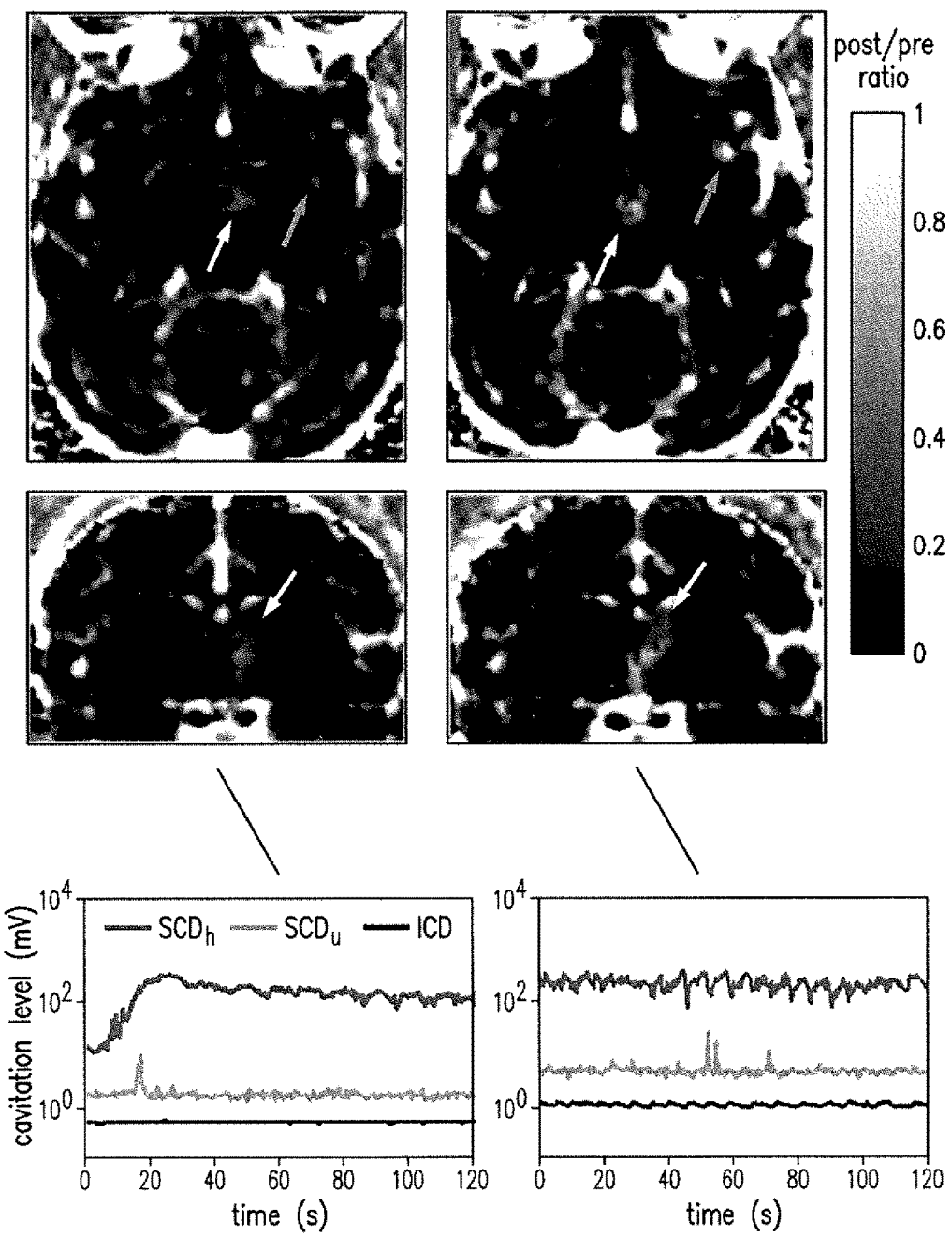
Figure 20:
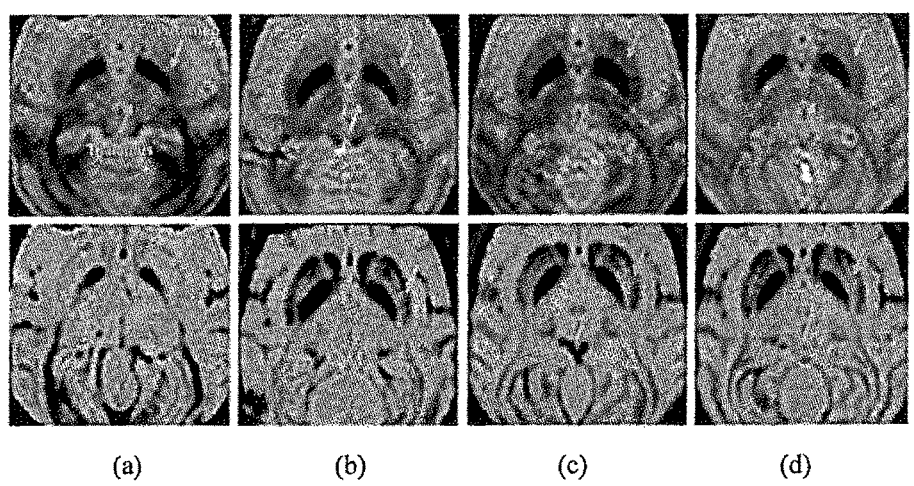
FIGS. 20A-20D are diagrams illustrating exemplary safety assessment using MRI according to the disclosed subject matter at (a) 275 kPa, (b) 350 kPa, (c) 450 kPa, and (d) 600 kPa. The upper row shows the T2-weighted images (coronal view) for detecting the edema, which is lighter if occurred. The lower row shows the SWI (coronal view) for detecting the hemorrhage, which is darker if occurred.

Safe BBB opening was achieved at low pressures (250-600 kPa) in both the putamen and the thalamus (FIGS. 19A-19D). No differences were observed in the putamen and the thalamus in terms of cavitation doses or opening threshold, as described herein. The opening volume varied across animals, and increased with pressure in the same macaque comparing the 350-kPa example (FIG. 19B) with the 600-kPa example (FIG. 19D). The 450-kPa case had a smaller opening volume than the 350-kPa case from the slightly decreasing SCDh, which can be due at least in part to the animal's physiological effect to the circulating microbubbles. The average SCDh at different pressures was at the same level, which can be due at least in part to the cavitation characteristics using long pulses and the high variation between examples, as illustrated for example in FIGS. 16A-16C.

For purpose of illustration, as embodied herein, the positive correlation of the ICD to pressure can be considered independent of the pulse length, which can affect cavitation characteristics. The ICD in the examples herein was not affected by the nonlinear ultrasound scattering due to the skull (as illustrated for example in the human skull results in FIGS. 15D-15F. The ICD can also provides a safety assessment. Improved ICD detection can be achieved by increasing the cavitation SNR. Additionally or alternatively, passive cavitation mapping, including spatial information of cavitation, can improve estimation of opening volume and safety assessment using both the SCDh and ICD.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. A system for real-time, transcranial monitoring of safe blood-brain barrier opening, comprising:
   an ultrasound transducer;
   a monitoring component configured to transcranially monitor opening of the blood-brain barrier by acquiring an emission from a microbubble; and
   a targeting component, coupled to the ultrasound transducer and configured to:

determine an approach angle for targeted blood-brain barrier opening proximate a predetermined region in a brain of a patient, and position the ultrasound transducer to generate a ultrasound signal at the determined approach angle to the predetermined region in the brain.

2. The system according to claim 1, wherein the ultrasound transducer operates at an intermediate frequency of 500 kHz.

3. The system according to claim 1, wherein the targeting component is configured to target the predetermined region of the brain without use of a magnetic resonance image monitoring.

4. The system according to claim 1, wherein the targeting component comprises a stereotactic manipulator to target the predetermined region in the brain.

5. The system according to claim 1, wherein the monitoring component monitors a frequency of a backscattered acoustic signal generated from the microbubble in response to the targeting by the ultrasound transducer.

6. The system according to claim 1, wherein the monitoring component comprises a passive cavitation detector.

7. The system of claim 1, wherein the approach angle for targeted blood-brain barrier opening transcends a skull of the patient.

8. The system according to claim 1, wherein the monitoring component is configured to perform a noninvasive real-time monitoring.

9. The system according to claim 1, wherein the ultrasound signal is a focused ultrasound signal.

10. A method for real-time, transcranial monitoring of safe blood-brain barrier opening, comprising:

providing an ultrasound transducer;

determining an approach angle for targeted blood-brain barrier opening proximate a predetermined region in a brain of a patient; and positioning the ultrasound transducer to generate a ultrasound signal at the determined approach angle to the predetermined region in the brain;

administering microbubbles to the patient;

generating the ultrasound signal at the determined approach angle to the predetermined region in the brain; and monitoring an occurrence of the blood-brain barrier opening by transcranially acquiring an emission from the microbubbles.

11. The method according to claim 10, further comprising operating the ultrasound transducer at an intermediate frequency of 500 kHz.

12. The method according to claim 10, further comprising targeting the predetermined region of the brain without use of a magnetic resonance image monitoring.

13. The method according to claim 10, further comprising targeting the predetermined region in the brain using a stereotactic manipulator.

14. The method according to claim 10, wherein the monitoring is performed by acquiring a frequency of a backscattered acoustic signal generated from the microbubbles in response to the targeting by the ultrasound transducer.

15. The method according to claim 10, wherein the monitoring is performed using a passive cavitation detector.

16. The method according to claim 10, wherein the patient is anesthetized during the blood-brain barrier opening.

17. The method according to claim 10, wherein the patient is awake during the blood-brain barrier opening.

18. The method of claim 10, wherein the approach angle for targeted blood-brain barrier opening transcends a skull of the patient.

19. The method according to claim 10, wherein the monitoring is noninvasive and real-time.

20. The method according to claim 10, wherein the ultrasound signal is a focused ultrasound signal.

* * * * *